(12) United States Patent
Beavers et al.

(10) Patent No.: US 7,314,937 B2
(45) Date of Patent: Jan. 1, 2008

(54) NON-IMIDAZOLE ARYL ALKYLAMINES COMPOUNDS AS HISTAMINE H3 RECEPTOR ANTAGONISTS, PREPARATION AND THERAPEUTIC USES

(75) Inventors: Lisa Selsam Beavers, Franklin, IN (US); Robert Alan Gadski, Indianapolis, IN (US); Philip Arthur Hipskind, New Palestine, IN (US); Craig William Lindsley, Schwenksville, PA (US); Karen Lynn Lobb, Indianapolis, IN (US); James Arthur Nixon, Indianapolis, IN (US); Richard Todd Pickard, Noblesville, IN (US); John Mehnert Schaus, Zionsville, IN (US); Takako Takakuwa, Indianapolis, IN (US); Brian Morgan Watson, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 528 days.

(21) Appl. No.: 10/472,675

(22) PCT Filed: Mar. 21, 2002

(86) PCT No.: PCT/US02/06644

§ 371 (c)(1),
(2), (4) Date: Sep. 18, 2003

(87) PCT Pub. No.: WO02/076925

PCT Pub. Date: Oct. 3, 2002

(65) Prior Publication Data

US 2004/0110748 A1 Jun. 10, 2004

(51) Int. Cl.
C07D 217/22 (2006.01)
A61K 31/47 (2006.01)
(52) U.S. Cl. .................... 546/141; 514/309
(58) Field of Classification Search ............ 514/309; 546/141
See application file for complete search history.

(56) References Cited

U.S. PATENT DOCUMENTS

| | | | |
|---|---|---|---|
| 2,810,719 A | 10/1957 | Moore et al. | |
| 4,963,563 A * | 10/1990 | DeBernardis et al. | 514/307 |
| 6,316,475 B1 | 11/2001 | Bennani et al. | |
| 6,610,721 B2 | 8/2003 | Andersen et al. | |
| 2001/0049367 A1 | 12/2001 | Bennani et al. | |
| 2002/0035103 A1 | 3/2002 | Bennani et al. | |
| 2002/0111340 A1 | 8/2002 | Bennani et al. | |
| 2002/0137931 A1 | 9/2002 | Bennani et al. | |
| 2002/0169188 A1 | 11/2002 | Cowart et al. | |

FOREIGN PATENT DOCUMENTS

| | | | |
|---|---|---|---|
| DE | 2635276 | * | 2/1977 |
| EP | 0114410 B1 | | 8/1984 |
| EP | 0237781 A1 | * | 9/1987 |
| EP | 0982300 A2 | | 3/2000 |
| EP | 1113007 A1 | * | 7/2001 |
| EP | 1283199 A1 | | 2/2003 |
| WO | WO-96/11192 | | 4/1996 |
| WO | WO-99/19293 | | 4/1999 |
| WO | WO-00/06254 | | 2/2000 |
| WO | WO-00/64884 | | 4/2000 |
| WO | WO00/42036 | * | 7/2000 |
| WO | WO-01/66534 A2 | | 9/2001 |
| WO | WO-02/06223 A1 | | 1/2002 |
| WO | WO-02/12190 A2 | | 2/2002 |
| WO | WO-02/40456 A1 | | 5/2002 |
| WO | WO-02/40461 A2 | | 5/2002 |
| WO | WO-02/074758 A2 | | 9/2002 |
| WO | WO-03/064411 A1 | | 8/2003 |

OTHER PUBLICATIONS

Wegner, CA 105:42726, Archiv der Pharmazie (Weinheim, German7), 1986, vol. 319(1), pp. 85-88, abstract only.*
Paul J. Gilligan et al., Novel Piperidine • Receptor Ligands as Potential Antipsychotic Drugs, J. Med. Chem., 1992, 4344-4361, vol. 35.
Von E. Rudinger-Adler et al., Synthese einiger Phenoxymethylphenyl-Derivate mit lokalanasthetischer Wirkung, Arzneim.-Forsch. /Drug Res, 1979, 591-594, vol. 29, No. 4.

(Continued)

Primary Examiner—D. Margaret Seaman
(74) Attorney, Agent, or Firm—Dan L. Wood

(57) ABSTRACT

The present invention discloses novel substituted aryl alkylamine compounds of Formula (I) or pharmaceutically acceptable salts thereof which have selective histamine-H3 receptor antagonist activity as well as methods for preparing such compounds. In another embodiment, the invention discloses pharmaceutical compositions comprising such cyclic amines as well as methods of using them to treat obesity and other histamine H3 receptor-related diseases

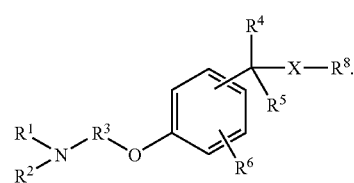

6 Claims, No Drawings

OTHER PUBLICATIONS

Severine Morisset et al., High constitutive activity of native $H_3$ receptors regulates histamine neurons in brain, Nature, 860-864, Dec. 14, 2000, vol. 408.

Ian D. Linney et al., Design, Synthesis, and Structure-Activity Relationships of Novel Non-Imidazole Histamine $H_3$ Receptor Antagonists, J. Med. Chem., 2362-2370, 2000, vol. 43.

Henk Van Der Goot et al., Selective ligands as tools to study histamine receptors, Eur. J. Med. Chem., 5-20, 2000, vol. 35.

Holger Stark et al., Analogues and Derivatives of Ciproxifan, a Novel Prototype for Generating Potent Histamine $H_3$-Receptor Antagonists, Bioorganic & Medicinal Chemistry Letters 2379-2382, 2000, vol. 10.

Albert D. Windhorst et al., Characterization of the Binding Site of the Histamine $H_3$ Receptr. 2. Synthesis, in Vitro Pharmacology, and QSAR of a Series of Monosubstituted Benzyl Analogues of Thioperamide, J. Med. Chem. 1754-1761, 2000, vol. 43.

Astrid Sasse et al., New Histamine $H_3$-Receptor Ligands of the proxifan Series: Imoproxifan and Other Sleective Antagonists with High Oral in Vivo Potency, J. Med. Chem., 3335-3343, 2000, vol. 43.

Holger Stark et al., Novel Histamine H3-Receptor Antagonists with Carbonyl-Substituted 4-(3- (Phenoxy)propyl)-1$H$-imidazole Structures like Ciproxifan and Related Compounds, J. Med. Chem., 3987-3994, 2000, vol. 43.

Astrid Sasse et al., (Partial) Agonist/Antagonist properties of Novel Diarylalkyl Carbamates on Histamine $H_3$ Receptors, Bioorganic & Medicinal Chemistry, 1139-1149, 2000, vol. 8.

Astrid Sasse et al., Benzophenone erivatives and Related Compounds as Potent Histamine $H_3$-Receptor Antagonists and Potential PET/SPECT Ligands, Arch. Pharm. Pharm. Med. Chem., 45-52, 2001, vol. 334.

Iwan J. P. De Esch et al., Development of a Pharmacophore Model for Histamine $H_3$ Receptor Antagonists, Using the Newly Developed Molecular Modeling Program SLATE, J. Med. Chem., 1666-1674, 2001, vol. 44.

Galina Meier et al., Influence of imidazole replacement in different structural classes of histamine $H_3$-receptor antagonists, European Journal of Pharmaceutical Sciences, 249-259, 2001, vol. 13.

Vijay K. Agrawal et al., QSAR Studies on Acylated Histamine Derivatives, Bioorganic & Medicinal Chemistry, 2787-2792, 2001, vol. 9.

Jean-Charles Schwartz et al., Application of genomics to drug design: the example of the histamine $H_3$ receptor, European Neuropsychopharmacology, 441-448, 2001, vol. 11.

Joachim Apelt et al., Development of a New Class of Nonimidazole Histamine $H_3$ Receptor Ligands with Combined Inhibitory Histamine $N$-Methyltransferase Activity, J. Med. Chem., 1128-1141, 2002, vol. 45.

Sven Grabmann et al., Progress in the Proxifan Class: Heterocyclic Congeners as Novel Potent and Selective Histamine $H_3$-Receptor Antagonists, European Journal of Pharmaceutical Sciences, 367-378, 2002, vol. 15.

Shigeki Habaue et al.; Anionic Polymerization of $o$-Substituted Styrene Derivatives: Control of Reactivity and Sterochemistry by Aminomethyl Group, Journal of Polymer Science: Part A: Polymer Chemistry, 2000, 4088-4094, vol. 38.

* cited by examiner

NON-IMIDAZOLE ARYL ALKYLAMINES COMPOUNDS AS HISTAMINE H3 RECEPTOR ANTAGONISTS, PREPARATION AND THERAPEUTIC USES

BACKGROUND OF THE INVENTION

The present invention relates to histamine H3 receptor antagonists, and as such are useful in the treatment of disorders responsive to the inactivation of histamine H3 receptors, such as obesity, cognitive disorders, attention deficient disorders and the like.

The histamine H3 receptor (H3R) is a presynaptic autoreceptor and heteroreceptor found in the peripheral and central nervous system and regulates the release of histamine and other neurotransmitters, such as serotonin and acetylcholine. The histamine H3 receptor is relatively neuron specific and inhibits the release of a number of monamines, including histamine. Selective antagonism of the histamine H3 receptor raises brain histamine levels and inhibits such activities as food consumption while minimizing non-specific peripheral consequences. Antagonists of the histamine H3 receptor increase synthesis and release of cerebral histamine and other monoamines. By this mechanism, they induce a prolonged wakefulness, improved cognitive function, reduction in food intake and normalization of vestibular reflexes. Accordingly, the histamine H3 receptor is an important target for new therapeutics in Alzheimer disease, mood and attention adjustments, cognitive deficiencies, obesity, dizziness, schizophrenia, epilepsy, sleeping disorders, narcolepsy and motion sickness.

The majority of histamine H3 receptor antagonists to date resemble histamine in possessing an imidazole ring generally substituted in the 4(5) position (Ganellin et al., Ars Pharmaceutica, 1995, 36:3, 455-468). A variety of patents and patent applications directed to antagonists and agonists having such structures include EP 197840, EP 494010, WO 97/29092, WO 96/38141, and WO96/38142. These imidazole-containing compounds have the disadvantage of poor blood-brain barrier penetration, interaction with cytochrome P-450 proteins, and hepatic and ocular toxicities.

Non-imidazole neuroactive compounds such as beta histamines (Arrang, Eur. J. Pharm. 1985, 111:72-84) demonstrated some histamine H3 receptor activity but with poor potency. EP 978512 published Mar. 1, 2000 discloses non-imidazole aryloxy alkylamines discloses histamine H3 receptor antagonists but does not disclose the affinity, if any, of these antagonists for recently identified histamine receptor GPRv53, described below. EP 0982300A2 (pub. Mar. 1, 2000) discloses non-imidazole alkyamines as histamine HS receptor ligand which are similar to the subject invention by having a phenoxy core structure although the subject invention is unique in the dissimilar substitutions at the ortho, meta or para positions of the central benzene ring, the exact substitutions of the non-oxygen benzene ring substituent, and in some cases the presence of a saturated, fused heterocyclic ring appended to the central benzene core. Furthermore the compounds of this invention are highly selective for the H3 receptor (vs. other histamine receptors), and possess remarkable drug disposition properties (pharmacokinetics).

Histamine mediates its activity via four receptor subtypes, H1R, H2R, H3R and a newly identified receptor designated GPRv53 [(Oda T., et al., J. Biol. Chem. 275 (47): 36781-6 (2000)]. Although relatively selective ligands have been developed for H1R, H2R and H3R, few specific ligands have been developed that can distinguish H3R from GPRv53. GPRv53 is a widely distributed receptor found at high levels in human leukocytes. Activation or inhibition of this receptor could result in undesirable side effects when targeting antagonism of the H3R receptor. Furthermore, the identification of this new receptor has fundamentally changed histamine biology and must be considered in the development of histamine H3 receptor antagonists.

Because of the unresolved deficiencies of the compounds described above, there is a continuing need for improved methods and compositions to treat disorders associated with histamine H3 receptors.

The present invention provides compounds that are useful as histamine H3 receptor antagonists. In another aspect, the present invention provides compounds that are useful as selective antagonists of the histamine H3 receptor but have little or no binding affinity of GPRv53. In yet another aspect, the present invention provides pharmaceutical compositions comprising antagonists of the histamine H3 receptor.

In yet another aspect, the present invention provides compounds, pharmaceutical compositions, and methods useful in the treatment of obesity, cognitive disorders, attention deficient disorders and other disorders associated with histamine H3 receptor.

SUMMARY OF THE INVENTION

The present invention is a compound structurally represented by Formula I

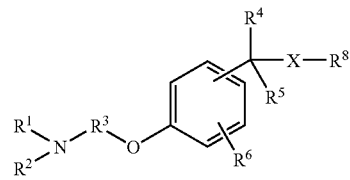

or pharmaceutically acceptable salts thereof wherein:

X is O, $NR^7$ or S;

$R^1$ is hydrogen, $C_1$-$C_8$ alkyl optionally substituted with 1 to 4 halogens, $(CHR^5)_n$—$C_3$-$C_7$ cycloalkyl, $(CHR^5)_n$ aryl, $(CHR^5)_n$ heteroaryl, or $(CHR^5)_n$—$O(CHR^5)_n$-aryl;

$R^2$ is independently $R^1$, or $COR^1$, or cyclized with the attached nitrogen atom at the $R^1$ position to form a 4, 5, or 6 member carbon ring, wherein one of said carbons is optionally replaced by one of O, S, $NR^1$ or CO, or wherein the ring formed by $R^1$ and $R^2$ is optionally substituted one to two times with $C_1$-$C_4$ alkyl;

$R^3$ is independently $C_3$-$C_7$ cycloalkylene, or $C_1$-$C_4$ alkylene optionally substituted;

$R^4$ is hydrogen, halogen, $C_1$-$C_4$ alkyl, $(CHR^5)_n$—$C_3$-$C_7$ cycloalkyl, $(CHR^5)_n$ aryl, $(CHR^5)_n$ heteroaryl, $(CHR^5)_n$—O $(CHR^5)_n$-aryl or CO or cyclized with $R^5$ to from a cyclopropyl ring;

$R^5$ is hydrogen, or $C_1$-$C_4$ alkyl;

$R^6$ is hydrogen, halo or cyclized with the attached carbon atom at the $R^5$ position to form a 5 to 6 member carbon ring, cyclized with the attached carbon atom at the $R^7$ position to form a 5 to 6 member heterocyclic ring or $R^7$ is hydrogen, $C_1$-$C_8$ alkyl optionally substituted with 1 to 4 halogens, $(CHR^5)_n$—$C_3$-$C_7$ cycloalkyl, $(CHR^5)_n$ aryl, $(CHR^5)_n$ heteroaryl, $(CHR^5)_n$—$O(CHR^5)_n$-aryl, $SO_2R^1$ or Cyclized with attached carbon on $R^8$ to from a 5, 6, or 7 membered carbon ring optionally substituted with $R^9$, $CF_3$, or CN, optionally one of the said carbons is replaced by N, $NR^1$, CO;

$R^8$ is hydrogen, a bond, $C_1$-$C_8$ alkyl —$SO_2$ $R^9$, —$CO_2$ $R^{10}$, —CO $R^9$, —$CONH$ $R^{10}$;

$R^9$ is hydrogen, halogen, $C_1$-$C_8$ alkyl optionally substituted with 1 to 4 halogens, $C_3$-$C_7$ cycloalkyl, aryl, $CH_2$ aryl, heteroaryl, heterocycle, —$O(CHR^5)_n$-aryl, —$COR^1$, —$CONR^1R^2$, —$SO_2R^1$, —$OR^1$, —$N(R^1)_2$, —$NR^1R^2$, —$CH_2NR^1$, $R^2$, —$CONR^1R^2$—$NHSO_2R^1$, —$NO_2$, —$CO_2R^1$, —$SO_2N(R^1)_2$, —$S(O)_nR^1$, —$OCF_3$, —$CH2SR^5$, $R^{10}$ is hydrogen, halogen, $C_1$-$C_8$ alkyl optionally substituted with 1 to 4 halogens, $C_3$-$C_7$ cycloalkyl, aryl, $CH_2$ aryl, heteroaryl, heterocycle, —$COR^1$, —$CONR^1$ $R^2$, —$SO_2R^1$, —$N(R^1)_2$, $NR^1R^2$, —$CH_2NR^1$, $R^2$, —$CONR^1R^2$, —$CO_2R^1$, —$SO_2N(R^1)_2$, —$S(O)_nR^1$, —$CH2SR^5$, and n is 0-4.

In preferred embodiments of Formula I the core phenoxy ring is an o, m, or p-disubstituted benzene, more preferably a p-disubstituted benzene. In alternative embodiments $R^6$ forms a bicyclic carbon ring at the $R^5$ position. Alternatively, $R^6$ may form a bicyclic heterocyclic ring at the $R^7$ position. Preferably, X is nitrogen, $R^4$ and $R^5$ are independently H or $CH_3$, R1 and R2 are independently a $C_1$-$C_8$ alkyl and R9 is a di-$C_1$ to $C_2$ alkyl-amino.

The present invention is a pharmaceutical composition which comprises a compound of Formula I and a pharmaceutically acceptable carrier. Pharmaceutical formulations of Formula I can provide a method of selectively increasing histamine levels in cells by contacting the cells with an antagonist of the histamine H3 receptor, the antagonists being a compound of Formula I.

The present invention further provides an antagonist of Formula I which is characterized by having little or no binding affinity for the histamine receptor GPRv53. Thus, a pharmaceutical preparation of Formula I can be useful in the treatment or prevention of obesity, cognitive disorders, attention deficient disorders and the like, which comprises administering to a subject in need of such treatment or prevention an effective amount of a compound of Formula I. In addition, a pharmaceutical preparation of Formula I can be useful in the treatment or prevention of a disorder or disease in which inhibition of the histamine H3 receptor has a beneficial effect or the treatment or prevention of eating disorders which comprises administering to a subject in need of such treatment or prevention an effective amount of a compound of Formula I.

DETAILED DESCRIPTION OF THE INVENTION

Throughout the instant application, the following terms have the indicated meanings:

The term "GPRv53" means a recently identified novel histamine receptor as described in Oda, et al., supra. Alternative names for this receptor are PORT3 or H4R.

The term "H3R" means to the histamine H3 receptor that inhibits the release of a number of monoamines, including histamine.

The term "H1R" means to the histamine H1 receptor subtype.

The term "H2R" means to the histamine H2 receptor subtype.

The term "selective H3R antagonists" is defined as the ability of a compound of the present invention to block forskolin-stimulated cAMP production in response to agonist R(−)α methylhistamine.

"Alkylene" are a saturated hydrocarbyldiyl radical of straight or branched configuration made up of from 1 to 4 carbon atoms. Included within the scope of this term are methylene, 1,2-ethane-diyl, 1,1-ethane-diyl, 1,3-propane diyl, 1,2-propane diyl, 1,3 butane-diyl, 1,4-butane diyl, and the like.

"$C_3$-$C_7$ cycloalkylene" are a saturated hydrocarbyldiyl radical of cyclic configuration, optionally branched, made up of from 3 to 7 carbon atoms. Included within the scope of this term are cyclopropyl, cyclobutyl, cyclopentyl and cyclohexyl, and the like.

"Alkyl" are one to four or one to eight carbon atoms such as methyl, ethyl, propyl, butyl, pentyl, hexyl, heptyl, octyl and isomeric forms thereof.

"Aryl" are six to twelve carbon atoms such as phenyl, alpha-naphthyl, beta-naphthyl, m-methylphenyl, p-trifluoromethylphenyl and the like. The aryl groups can also be substituted with one to 3 hydroxy, fluoro, chloro, or bromo groups.

"Cycloalkyl" are three to seven carbon atoms such as cyclopropyl, cyclobutyl, cyclopentyl and cyclohexyl.

"Heteroaryl" are six to twelve carbon atoms aryls, as described above, containing the heteroatoms nitrogen, sulfur or oxygen. Heteroaryls are pyridine, thiophene, furan, pyrimidine, 2-pyridyl, 3-pyridyl, 4-pyridyl, 2-pyrimidinyl, 4-pyrimidinyl, 5-pyrimidinyl, 3-pyridazinyl, 4-pryidazinyl, 3-pyrazinyl, 2-quinolyl, 3-quinolyl, 1-isoquinolyl, 3-isoquinolyl, 4-isoquinolyl, 2-quinazolinyl, 4-quinazolinyl, 2-quinoxalinyl, 1-phthalazinyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-indolyl, 3-indolyl, 3-indazolyl, 2-benzoxazolyl, 2-benzothiazolyl, 2-benzimidazolyl, 2-benzofuranyl, 3-benzofuranyl, 2-furanyl, 3-furanyl, 2-thienyl, 3-thienyl, 2-pyrrolyl, 3-pyrrolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,2,4-triazol-5-yl, 1,2,3,4-tetrazol-5-yl, 5-oxazolyl, 1-pyrrolyl, 1-pyrazolyl, 1,2,3-triazol-1-yl, 1,2,4-triazol-1-yl, 1-tetrazolyl, 1-indolyl, 1-indazolyl, 2-isoindolyl, 1-purinyl, 3-isothiazolyl, 4-isothiazolyl, 5-isothiazolyl.

"Heterocycle" are three to twelve carbon atom cyclic aliphatic rings, wherein one or more carbon atoms is replaced by a hetero-atom which is nitrogen, sulfur or oxygen.

"Halogen" or "halo" means fluoro, chloro, bromo and iodo.

"Composition" means a pharmaceutical composition and is intended to encompass a pharmaceutical product comprising the active ingredient(s), Formula I, and the inert ingredient(s) that make up the carrier. Accordingly, the pharmaceutical compositions of the present invention encompass any composition made by admixing a compound of the present invention and a pharmaceutically acceptable carrier.

The term "unit dosage form" means physically discrete units suitable as unitary dosages for human subjects and other non-human animals, each unit containing a predetermined quantity of active material calculated to produce the desired therapeutic effect, in association with a suitable pharmaceutical carrier.

The terms "treating" and "treat", as used herein, include their generally accepted meanings, i.e., preventing, prohibiting, restraining, alleviating, ameliorating, slowing, stopping, or reversing the progression or severity of a pathological condition, described herein.

In one embodiment, the present invention provides compounds of Formula I as described in detail above. Another embodiments are where the phenoxy core structure is an o, m, or p-disubstituted aryl. Another embodiment is a compound wherein $R^6$ is cyclized with the attached carbon atom at $R^7$ to form, including the fused benzene ring, a substituted tetrahydroisoquinoline ring. Another embodiment is a compound wherein X is nitrogen, and wherein $R^7$ and $R^8$ are cyclized to form, together with X, a pyrrolidine ring, and wherein $R^9$ is —CH2—N-pyrrolidinyl.

A preferred moiety for X is independently O or N.

A preferred moiety for $R^9$ is $C_1$-$C_8$ dialkylamino. A more preferred embodiment is where the dialkylamino is dimethylamino.

It will be understood that, as used herein, references to the compounds of Formula I are meant to also include the pharmaceutical salts, its enantiomers and racemic mixtures thereof.

Because certain compounds of the invention contain a basic moiety (e.g., amino), the compound of Formula I can exist as a pharmaceutical acid addition salt. Such salts include sulfate, pyrosulfate, bisulfate, sulfite, bisulfite, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4 dioate, 3-hexyne-2,5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, beta-hydroxybutyrate, glycollate, maleate, tartrate, methanesulfonate, propanesulfonate, naphthalene-1-sulfonate, naphthalene-2-sulfonate, mandelate and the like salts.

As stated earlier, the invention includes tautomers, enantiomers and other stereoisomers of the compounds also. Thus, as one skilled in the art knows, certain aryls may exist in tautomeric forms. Such variations are contemplated to be within the scope of the invention.

The compounds of Formula I may be prepared by several processes well known in the art. The compounds of the present invention are prepared by standard alkylation or Mitsunobu chemistries and reductive animations known to one skilled in the art, or by the methods provided herein, supplemented by methods known in the art. Generally, this reaction is conducted in an organic solvent such as, for example, halogenated hydrocarbons, toluene, acetonitrile and the like, preferably in the absence of moisture, at temperatures in the range about 0-100° C., by bringing together the ingredients in contact in the solvent medium and stirring for about 10 minutes to about 48 hours at such temperatures.

The compounds of Formula I, when existing as a diastereomeric mixture, may be separated into diastereomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent. Alternatively, any enantiomer of a compound of the formula may be obtained by stereospecific synthesis using optically pure starting materials or reagents of known configuration or through enantioselective synthesis.

The Examples shown in Table 1 below are being provided to further illustrate the present invention. They are for illustrative purposes only; the scope of the invention is not to be considered limited in any way thereby. The preparation of compounds of Formula I, are depicted in the schemes and procedures below.

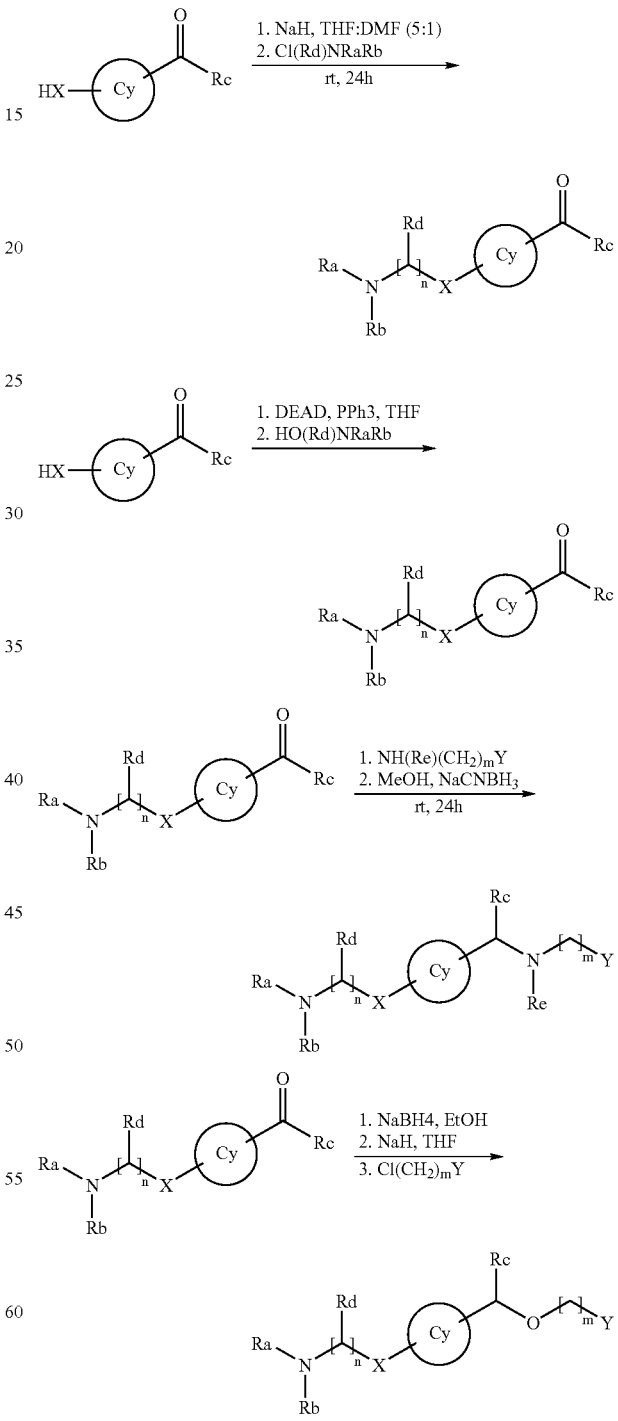

-continued

Scheme 2

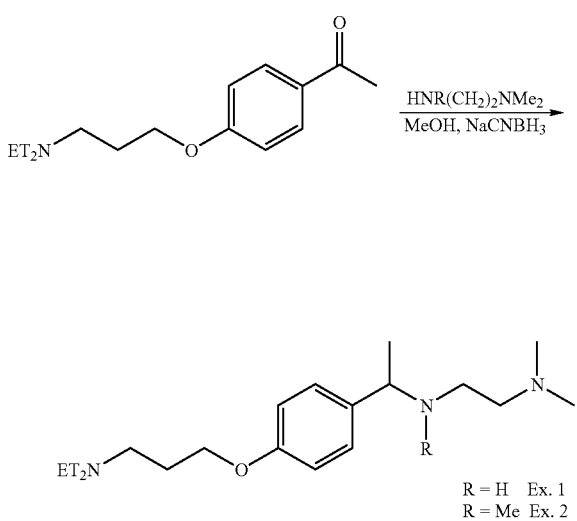

R = H Ex. 1
R = Me Ex. 2

Preparation of N-{1-[4-(3-Dimethylamino-propoxy)-phenyl-N',N'-dimethyl-ethane-1,2-diamine

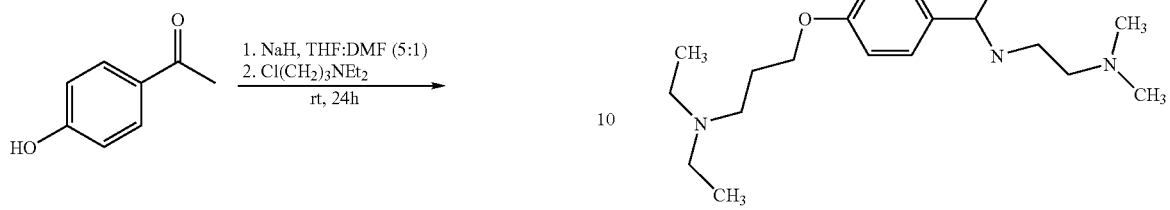

EXAMPLE 2

To a 100 mL round-bottom flask was placed NaH (60% dispersion, 38.4 mg, 1.0 mmol) and anhydrous THF (10 mL, 0.1 M) under an atmosphere of nitrogen. Then, a DMF solution of p-hydroxyacetophenone (62 mg, 0.5 mmol) was added at 0 C. After 15 minutes, a DMF solution of 3-chloro-N,N-diethyl-N-proplyamine (150 mg, 1.0 mmol) was added, and the reaction was allowed to slowly reach room temperature over 3 hours. The reaction was then quenched with water, diluted with ether and washed with water (3×20 mL) and brine (2×20 mL). Concentration in vacuo afforded 114 mg (92%) of an off-white solid. LCMS indicated a purity of 95% and hit the mass, 249.1. This material was then dissolved in ethanol (4 mL, 0.1M) and 1-N,N-dimethylamino-2-N-methylaminoethane (114 mg, 0.45 mmol) was added. After 15 minutes at room temperature, NaCNBH₃ (56 mg, 0.9 mmol) was added and the reaction was allowed to stir overnight at room temperature. The reaction was then with water, diluted with ether and washed with water (3×20 mL) and brine (2×20 mL). Concentration in vacuo afforded 134 mg (93%) of an orange oil. Column chromatography (9:1, CH₂Cl₂:MeOH) afforded an orange oil. LCMS indicated a purity of 99% and hit the mass, 321.2.

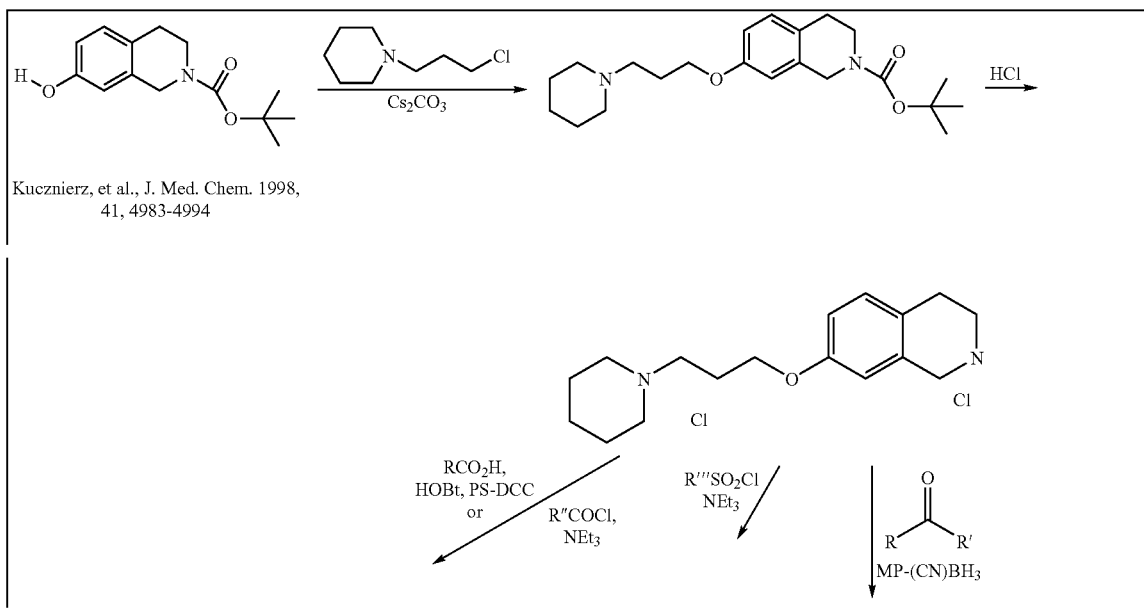

7-OH tetrahydroisoquinoline series

Kucznierz, et al., J. Med. Chem. 1998, 41, 4983-4994

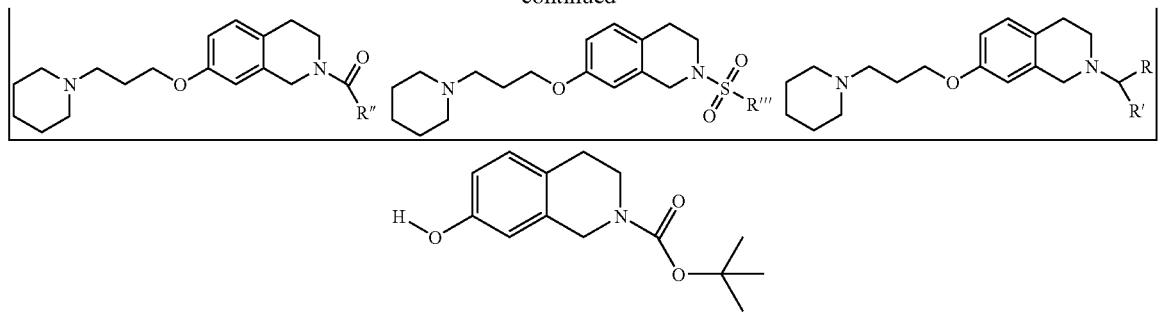

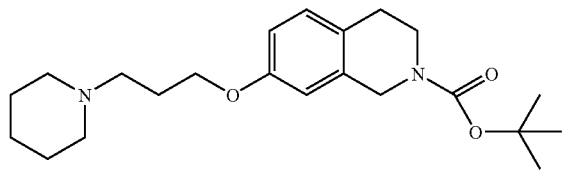

7-Hydroxy-3,4-dihydro-1-H-isoquinoline-2-carboxylic acid tert-butyl ester is prepared by the procedure described in Kucznierz, et.al., J. Med. Chem. 1998, 41, 4983-4994. MS(ES−) 248.1 (M−)⁻.

EXAMPLE 228

7-(3-Piperidin-1-yl-propoxy-3,4-dihydro-1-H-isoquinoline-2-carboxylic acid tert-butyl ester;

Procedure A: A 100 mL dioxane solution of 7-hydroxy-3,4-dihydro-1-H-isoquinoline-2-carboxylic acid tert-butyl ester (5.0 g, 20 mmol) is stirred under $N_2$ as $Cs_2CO_3$ (13.3 g, 43 mmol), KI (0.1 g, 0.6 mmol), then N-(3-chloropropyl) piperidine (3.9 g, 24 mmol) are added in succession. The reaction mixture is heated at 90° C. for 10 hours, cooled, filtered, and concentrated to give the crude product. Purification by chromatography ($SiO_2$; 0-10% MeOH/$CH_2Cl_2$/1% $NH_4OH$ gradient) gives the product as an amber oil (7.5 g, 100% yield). MS(ES+)375.3(M+H)⁺.

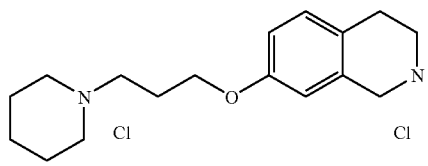

EXAMPLE 238

7-(3-Piperidin-1-yl-propoxy)-1,2,3,4-tetrahydro-isoquinoline dihydrochloride;

Procedure B: A 50 mL $CH_2Cl_2$ solution of 7-(3-Piperidin-1-yl-propoxy-3,4-dihydro-1-H-isoquinoline-2-carboxylic acid tert-butyl ester (5.1 g, 13.8 mmol) is stirred under $N_2$ at 0-10° C. as 4N HCl/dioxane (11.5 mL, 46 mmol) is added dropwise. After the addition is complete, reaction mixture is stirred at this temperature for 30-60 min, then allowed to warm to room temperature. A white precipitate forms and dry MeOH is added until clear solution is obtained. Additional 4N HCl/dioxane (11.0 mL, 44 mmol) is added dropwise. After the addition is complete, reaction mixture is stirred at room temperature. Reaction is followed by TLC ($SiO_2$ plate, $CH_3Cl$/MeOH/$NH_4OH$; 25/5/1) until starting material consumed (4-5 h). Reaction mixture is concentrated, dissolved in dry MeOH, concentrated, triturated in $Et_2O$, filtered, and dried in vacuo to give the di-HCl salt (4.5 g, 94% yield) as a white solid. MS(ES+)275.3(M+H)⁺ free base.

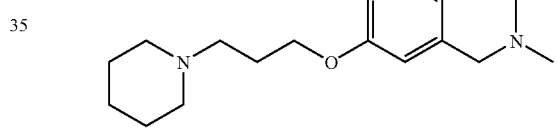

EXAMPLE 245

2-Methyl-7-(3-Piperidin-1-yl-propoxy)-1,2,3,4-tetrahydro-isoquinoline: A 10 mL THF suspension of LAH (150 mg, 4 mmol) is stirred under $N_2$ at 0-10° C. as a 10 mL THF solution of 7-(3-piperidin-1-yl-propoxy-3,4-dihydro-1-H-isoquinoline-2-carboxylic acid tert-butyl ester (200 mg, 0.53 mmol) is added dropwise. Reaction mixture is allowed to warm to room temperature, refluxed 90 minutes, cooled to 0-10° C., quenched with $H_2O$ and 15% aqueous NaOH, filtered, and the filtrate concentrated to give crude product. Material is purified by chromatography ($SiO_2$; 0-10% MeOH/$CH_2Cl_2$/1% $NH_4OH$ gradient) to give the product (82 mg, 54% yld). MS(ES+)289.1(M+H)⁺.

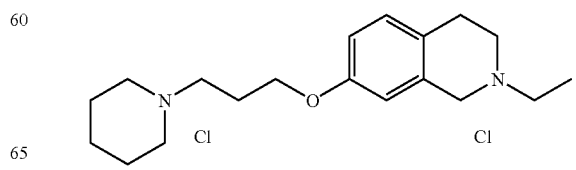

EXAMPLE 271

2-Ethyl-7-(3-Piperidin-1-yl-propoxy)-1,2,3,4-tetrahydro-isoquinoline dihydrochloride;

Procedure C: An 80 mL CH$_2$Cl$_2$/MeOH (9:1) solution of 7-(3-piperidin-1-yl-propoxy)-1,2,3,4-tetrahydro-isoquinoline dihydrochloride (658972)(2.95 g, 8.5 mmol) is stirred under N$_2$, the MP-CNBH$_3$ resin(15 g, 38 mmol) added, the acetaldehyde (5 mL, 89 mmol) added, the pH is adjusted to ~4 with glacial AcOH and reaction mixture stirred at room temperature for 18-20 hours. The reaction mixture is filtered and the resin beads washed twice alternately with MeOH, then CH$_2$Cl$_2$. The filtrate is concentrated and the residue is purified by chromatography (SCX-MeOH wash, elute 2M NH$_3$/MeOH; then (SiO$_2$; 0-10% MeOH/CH$_2$Cl$_2$/1% NH$_4$OH gradient) to give the pure free base.

Procedure D: A 50 mL THF/MeOH (1:1) solution of the free base (1.52 g, 5 mmol) is stirred under N$_2$ at 0-10° C. as 1N HCl/Et$_2$O (11.5 mL, 11.5 mmol) is added dropwise. After the addition is complete, reaction mixture is allowed to warm to room temperature, then reaction mixture is concentrated, dissolved in dry MeOH, concentrated, triturated in Et$_2$O, filtered, and dried in vacuo to give the di-HCl salt (4.5 g, 94% yld) as a white solid. MS(ES+)303.3(M+H)$^+$ free base.

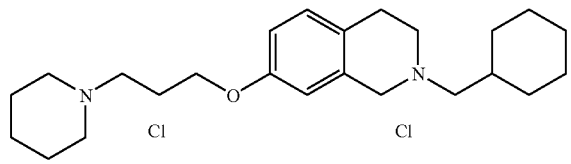

EXAMPLE 292 (di-HCL Salt)

EXAMPLE 273 (Free Base)

2-Cyclohexylmethyl-7-(3-piperidin-1-yl-propoxy)-1,2,3,4-tetrahydro-isoquinoline dihydrochloride: 2-Cyclohexylmethyl-7-(3-piperidin-1-yl-propoxy)-1,2,3,4-tetrahydro-isoquinoline is prepared from 7-(3-piperidin-1-yl-propoxy)-1,2,3,4-tetrahydro-isoquinoline dihydrochloride (6 g, 17 mmol), MP-CNBH$_3$ (30 g, 76.5 mmol), and cyclohexanecarboxaldehyde (12.4 mL, 102 mmol) via a procedure substantially analogous to Procedure C except that the SCX column is not used in purification. The di-HCl salt product (4.9 g, 65% yld) is isolated as a white solid via a procedure substantially analogous to Procedure D. MS(ES+)371.4(M+H)$^+$ free base.

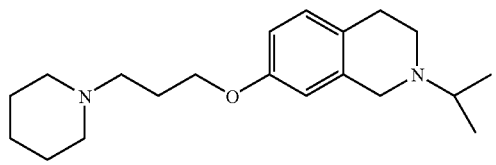

EXAMPLE 244

2-Isopropyl-7-(3-piperidin-1-yl-propoxy)-1,2,3,4-tetrahydro-isoquinoline: 2-Isopropyl-7-(3-piperidin-1-yl-propoxy)-1,2,3,4-tetrahydro-isoquinoline is prepared from 7-(3piperidin-1-yl-propoxy)-1,2,3,4-tetrahydro-isoquinoline dihydrochloride (520 mg, 1.5 mmol), MP-CNBH$_3$ (3.2 g, 7.5 mmol), and acetone (1.1 mL, 15 mmol) via a procedure substantially analogous to Procedure C except that the SCX column is not used in purification. The product (210 mg, 44% yld) is isolated as a clear oil. MS(ES+)317.2(M+H)$^+$.

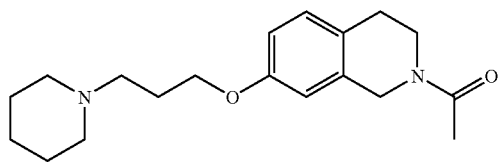

EXAMPLE 275

1-[7-(3-Piperidin-1-yl-propoxy)-3,4-dihydro-1H-isoquinolin-2-yl]-ethanone: A 5 mL CH$_2$Cl$_2$ solution of 7-(3-piperidin-1-yl-propoxy)-1,2,3,4-tetrahydro-isoquinoline dihydrochloride (175 mg, 0.5 mmol) and NEt$_3$ (0.25 mL, 1.7 mmol) is stirred under N$_2$, a 1 mL CH$_2$Cl$_2$ solution of acetyl chloride (0.043 mL, 0.6 mmol) is added, and reaction is stirred at room temp. for 5-6 hours. Reaction mixture is quenched with MeOH, concentrated and the residue is purified by chromatography (SCX-MeOH wash, elute 2M NH$_3$/MeOH; then (SiO$_2$; 0-10% MeOH/CH$_2$Cl$_2$/1% NH$_4$OH gradient) to give the product (90 mg, 58% yld). MS(ES+)317.1(M+H)$^+$

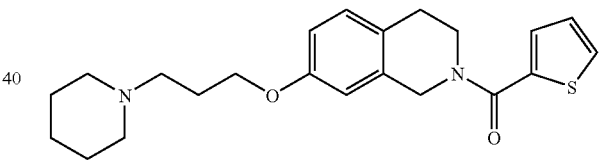

EXAMPLE 257

[7-(3-Piperidin-1-yl-propoxy)-3,4-dihydro-1H-isoquinolin-2-yl]-thiophen-2-yl-methanone;

Procedure E: A 7 mL CHCl$_3$/t-BuOH/MeCN (5:1:1) mixture of 7-(3-piperidin-1-yl-propoxy)-1,2,3,4-tetrahydro-isoquinoline dihydrochloride (256 mg, 0.74 mmol), resin bound DCC (1.1 g, 0.9 mmol), hydroxybenzotriazole (HOBt, 150 mg, 1.1 mmol), and thiophene-2-carboxylic acid (118 mg, 0.9 mmol) is shaken in a capped vial at room temperature for 48 hours. The reaction mixture is filtered and the resin beads washed twice alternately with MeOH, then CH$_2$Cl$_2$. The filtrate is concentrated and the residue is purified by chromatography (SCX-MeOH wash, elute 2M NH$_3$/MeOH; then SiO$_2$; 0-10% MeOH/CH$_2$Cl$_2$/1% NH$_4$OH gradient) to give the pure free base as a solid (180 mg, 63% yld). MS(ES+) 385.1(M+H)$^+$. A 3 mL dry MeOH solution of the free base (45 mg, 0.12 mmol) is stirred with 1N HCl/Et$_2$O (0.18 mL, 0.18 mmol) for 5 minutes, concentrated, triturated with Et$_2$O, filtered, and dried in vacuo to the HCl salt as an off-white solid (46 mg). MS(ES+) 385.1 (M+H)$^+$ free base.

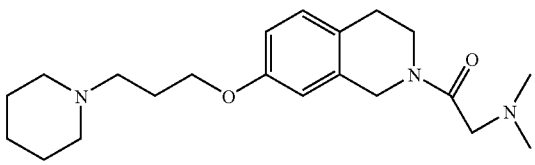

EXAMPLE 274

2-Dimethylamino-1-[7-(3-piperidin-1-yl-propoxy)-3,4-dihydro-1H-isoquinolin-2-yl]-ethanone: 2-Dimethylamino-1-[7-(3-piperidin-1-yl-propoxy)-3,4-dihydro-1H-isoquinolin-2-yl]-ethanone is prepared from 7-(3-piperidin-1-yl-propoxy)-1,2,3,4-tetrahydro-isoquinoline dihydrochloride (175 mg, 0.5 mmol), PS-DCC (800 mg, 1.1 mmol), HOBt (80 mg, 0.77 mmol), NEt$_3$ (0.21 mL, 1.5 mmol) and N,N-dimethylglycine (1.1 mL, 15 mmol) via a procedure substantially analogous to Procedure E except that PS-trisamine resin beads (700 mg, 2.6 mmol) is used in the work up to scavenge the excess HOBt and N,N-dimethylglycine. The free base product (35 mg, 19% yld) is isolated as an oil. MS(ES+)360.5(M+H)$^+$.

EXAMPLE 266

7-(3-Piperidin-1-yl-propoxy)-3,4-dihydro-1H-isoquinoline-2-carboxylic acid isopropylamide: A 10 mL CH$_2$Cl$_2$ solution of 7-(3-piperidin-1-yl-propoxy)-1,2,3,4-tetrahydro-isoquinoline dihydrochloride (254 mg, 0.73 mmol), NEt$_3$ (0.20 mL, 1.4 mmol), isopropyl isocyanate (192 mg, 2.2 mmol), and 4-dimethylaminopyridine (12 mg, 0.1 mmol) is stirred under N$_2$, at room temperature for 18 hours. The reaction mixture is concentrated and the residue is purified by chromatography (SCX-MeOH wash, elute 2M NH3/MeOH; then SiO$_2$; 0-10% MeOH/CH$_2$Cl$_2$/1% NH$_4$OH gradient) to give pure product (110 mg, 42% yld). MS(ES+) 360.2(M+H)$^+$.

EXAMPLE 249

2-Benzenesulfonyl-7-(3-piperidin-1-yl-propoxy)-1,2,3,4-tetrahydro-isoquinoline;

Procedure F: A 5 mL CH$_2$Cl$_2$ solution of 7-(3-piperidin-1-yl-propoxy)-1,2,3,4-tetrahydro-isoquinoline dihydrochloride (185 mg, 0.53 mmol) and NEt$_3$ (0.22 mL, 1.8 mmol) is stirred under N$_2$, benzenesulfonyl chloride (0.08 mL, 0.62 mmol) is added, and reaction is stirred at room temperature for 5-6 hours. Reaction mixture is diluted with EtOAc, washed with saturated aqueous Na$_2$CO$_3$, and the aqueous layer back-extracted with EtOAc. The EtOAc extracts are combined, dried (Na$_2$SO$_4$), and concentrated. The residue is purified by chromatography (SiO$_2$; 0-6% MeOH/CH$_2$Cl$_2$/1% NH$_4$OH gradient) to give the product (160 mg, 73% yld). MS(ES+) 415.1(M+H)$^+$.

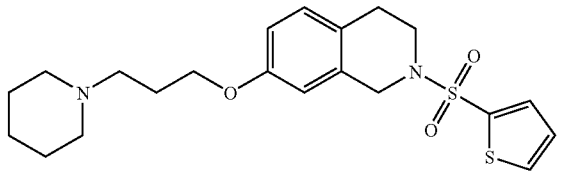

EXAMPLE 268

7-(3-Piperidin-1-yl-propoxy)-2-(thiophene-2-sulfonyl)-1,2,3,4-tetrahydro-isoquinoline: 7-(3-Piperidin-1-yl-propoxy)-2-(thiophene-2-sulfonyl)-1,2,3,4-tetrahydro-isoquinoline is prepared from 7-(3-piperidin-1-yl-propoxy)-1,2,3,4-tetrahydro-isoquinoline dihydrochloride (175 mg, 0.5 mmol), NEt$_3$ (0.25 mL, 1.8 mmol), and thiophene-2-sulfonyl chloride (114 mg, 0.63 mmol) via a procedure substantially analogous to Procedure F except that an additional SCX column purification step is performed to give the product (160 mg, 76% yld). MS(ES+)421.1(M+H)$^+$.

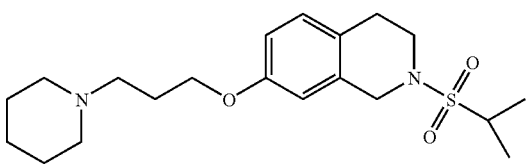

EXAMPLE 267

7-(3-Piperidin-1-yl-propoxy)-2-(propane-2-sulfonyl)-1,2,3,4-tetrahydro-isoquinoline: 7-(3-Piperidin-1-yl-propoxy)-2-(propane-2-sulfonyl)-1,2,3,4-tetrahydro-isoquinoline is prepared from 7-(3-piperidin-1-yl-propoxy)-1,2,3,4-tetrahydro-isoquinoline dihydrochloride (175 mg, 0.5 mmol), NEt$_3$ (0.25 mL, 1.8 mmol), and isopropylsulfonyl chloride (0.07 mL, 0.60 mmol) via a procedure substantially analogous to Procedure F except that an additional SCX column purifi-

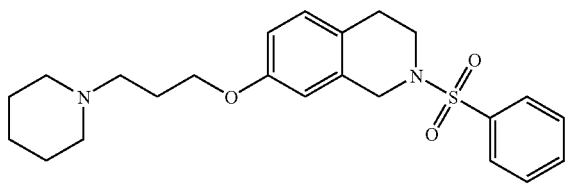

cation step is performed to give the product (93 mg, 49% yld). MS(ES+) 381.1(M+H)+.

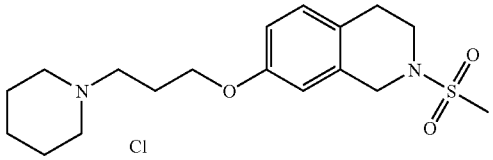

EXAMPLE 284

2-Methanesulfonyl-7-(3-piperidin-1-yl-propoxy)-1,2,3,4-tetrahydro-isoquinoline hydrochloride: 2-Methanesulfonyl-7-(3-piperidin-1-yl-propoxy)-1,2,3,4-tetrahydro-isoquinoline hydrochloride is prepared from 7-(3-piperidin-1-yl-propoxy)-1,2,3,4-tetrahydro-isoquinoline dihydrochloride (183 mg, 0.52 mmol), NEt$_3$ (0.25 mL, 1.8 mmol), and methanelsulfonyl chloride (0.05 mL, 0.66 mmol) via a procedure substantially analogous to Procedure F except that an additional SCX column purification step is performed to give the free base product. A 5 mL dry MeOH solution of the free base (110 mg, 0.31 mmol) is stirred with 1N HCl/Et$_2$O (0.50 mL, 0.5 mmol) for 5 minutes, concentrated, triturated with Et$_2$O, the Et$_2$O decanted, and the residue dried in vacuo to give the HCl salt as a glass (118 mg, 65% yld). MS(ES+) 353.2(M+H)+ free base.

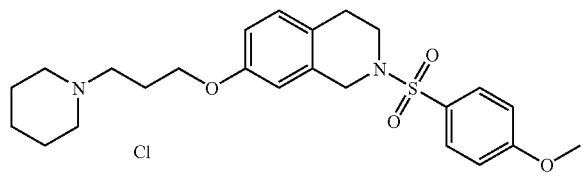

EXAMPLE 286

2-(4-Methoxy-benzenesulfonyl-7-(3-piperidin-1-yl-propoxy)-1,2,3,4-tetrahydro-isoquinoline hydrochloride: 2-(4-Methoxy-benzenesulfonyl-7-(3-piperidin-1-yl-propoxy)-1,2,3,4-tetrahydro-isoquinoline hydrochloride is prepared from 7-(3-piperidin-1-yl-propoxy)-1,2,3,4-tetrahydro-isoquinoline dihydrochloride (150 mg, 0.43 mmol), NEt$_3$ (0.21 mL, 1.5 mmol), and 4-methoxybenzenesulfonyl chloride (115 mg, 0.57 mmol) via a procedure substantially analogous to Procedure F except that an additional SCX column purification step is performed to give the free base product. A 5 mL dry MeOH solution of the free base (131 mg, 0.29 mmol) is stirred with 1N HCl/Et$_2$O (0.40 mL, 0.4 mmol) for 5 minutes, concentrated, triturated with Et$_2$O, filtered, and dried in vacuo to give the HCl salt (118 mg, 57% yld). MS(ES+) 445.2(M+H)+ free base.

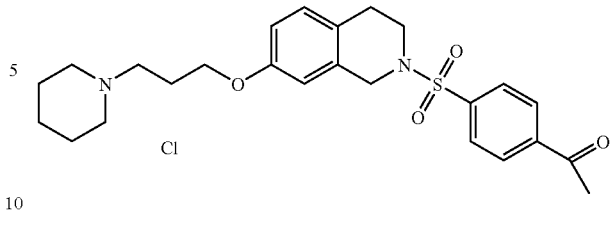

EXAMPLE 277

1-{4-[7-(3-Piperidin-1-yl-propoxy)-3,4-dihydro-1H-isoquinoline-2-sulfonyl]-phenyl}-ethanone: 1-{4-[7-(3-Piperidin-1-yl-propoxy)-3,4-dihydro-1H-isoquinoline-2-sulfonyl]-phenyl}-ethanone is prepared from 7-(3-piperidin-1-yl-propoxy)-1,2,3,4-tetrahydro-isoquinoline dihydrochloride (175 mg, 0.5 mmol), NEt$_3$ (0.25 mL, 1.8 mmol), and 4-acetylbenzenelsulfonyl chloride (131 mg, 0.60 mmol) via a procedure substantially analogous to Procedure F except that an additional SCX column purification step is performed to give the product (85 mg, 37% yld). MS(ES+) 457.1(M+H)+.

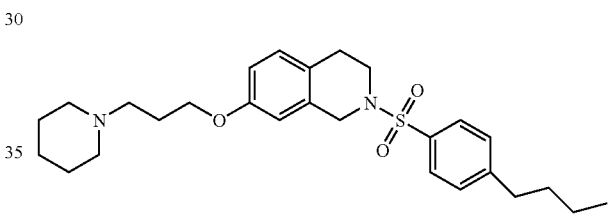

EXAMPLE 276

2-(4-n-Butyl-benzenesulfonyl)-7-(3-piperidin-1-yl-propoxy)-1,2,3,4-tetrahydro-isoquinoline: 2-(4-n-Butyl-benzenesulfonyl)-7-(3-piperidin-1-yl-propoxy)-1,2,3,4-tetrahydro-isoquinoline is prepared from 7-(3-piperidin-1-yl-propoxy)-1,2,3,4-tetrahydro-isoquinoline dihydrochloride (175 mg, 0.5 mmol), NEt$_3$ (0.25 mL, 1.8 mmol), and 4-(n-butyl)benzenesulfonyl chloride (140 mg, 0.60 mmol) via a procedure substantially analogous to Procedure F except that an additional SCX column purification step is performed to give the product (165 mg, 70% yld). MS(ES+) 471.1(M+H)+.

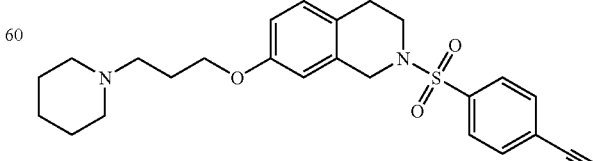

EXAMPLE 278

2-(4-Cyanobenzenesulfonyl)-7-(3-piperidin-1-yl-propoxy)-1,2,3,4-tetrahydro-isoquinoline: 2-(4-Cyanobenzenesulfonyl)-7-(3-piperidin-1-yl-propoxy)-1,2,3,4-tetrahydro-isoquinoline is prepared from 7-(3-piperidin-1-yl-propoxy)-1,2,3,4-tetrahydro-isoquinoline dihydrochloride (175 mg, 0.5 mmol), NEt$_3$ (0.25 mL, 1.8 mmol), and 4-cyanobenzenesulfonyl chloride (121 mg, 0.60 mmol) via a procedure substantially analogous to Procedure F except that an additional SCX column purification step is performed to give the product (157 mg, 71% yld). MS(ES+) 440.1(M+H)$^+$.

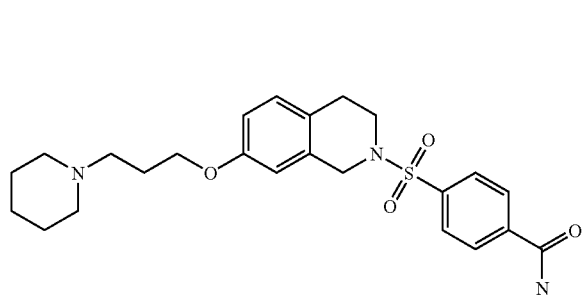

EXAMPLE 287

4-[7-(3-Piperidin-1-yl-propoxy)-3,4-dihydro-1H-isoquinoline-2-sulfonyl]-benzamide: A 1.4 mL DMSO mixture of K$_2$CO$_3$ is stirred under N$_2$, 2-(4-cyanobenzenesulfonyl)-7-(3-piperidin-1-yl-propoxy)-1,2,3,4-tetrahydro-isoquinoline (75 mg, 0.17 mmol) is added, 0.2 mL H$_2$O added, followed by 30% H$_2$O$_2$ (1.4 mL, 12 mmol) and reaction is stirred at room temperature for 4 hours. The reaction mixture is diluted with MeOH, filtered, and the solids washed twice with MeOH. The filtrate is concentrated and the residue is purified by chromatography (SCX-MeOH wash, elute 2M NH$_3$/MeOH; then SiO$_2$; 0-10% MeOH/CH$_2$Cl$_2$/1% NH$_4$OH gradient) to give the product as an off-white solid (26 mg, 26% yld). MS (ES+)458.2(M+H)$^+$.

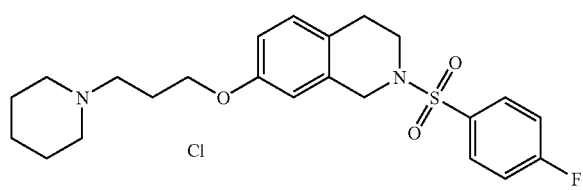

EXAMPLE 285

2-(4-Fluoro-benzenesulfonyl)-7-(3-piperidin-1-yl-propoxy)-1,2,3,4-tetrahydro-isoquinoline hydrochloride: 2-(4-Fluoro-benzenesulfonyl)-7-(3-piperidin-1-yl-propoxy)-1,2,3,4-tetrahydro-isoquinoline hydrochloride is prepared from 7-(3-piperidin-1-yl-propoxy)-1,2,3,4-tetrahydro-isoquinoline dihydrochloride (158 mg, 0.45 mmol), NEt$_3$ (0.21 mL, 1.5 mmol), and 4-fluorobenzenesulfonyl chloride (115 mg, 0.55 mmol) via a procedure substantially analogous to Procedure F except that an additional SCX column purification step is performed to give 140 mg of free base product. The free base is converted to the HCl salt (150 mg, 71% yld) via a procedure substantially analogous Procedure D. MS (ES+)433.2(M+H)$^+$ free base.

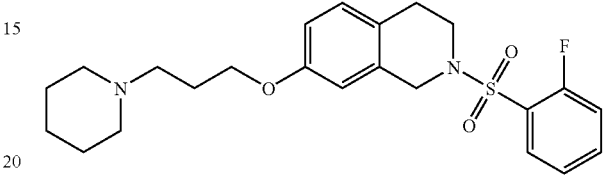

EXAMPLE 304

2-(2-Fluoro-benzenesulfonyl)-7-(3-piperidin-1-yl-propoxy)-1,2,3,4-tetrahydro-isoquinoline: 2-(2-Fluoro-benzenesulfonyl)-7-(3-piperidin-1-yl-propoxy)-1,2,3,4-tetrahydro-isoquinoline is prepared from 7-(3-piperidin-1-yl-propoxy)-1,2,3,4-tetrahydro-isoquinoline dihydrochloride (104 mg, 0.3 mmol), NEt$_3$ (0.14 mL, 1.1 mmol), and 2-fluorobenzenesulfonyl chloride (80 mg, 0.41 mmol) via a procedure substantially analogous to Procedure F except that an additional SCX column purification step is performed to give the free base product (85 mg, 66% yld) as an amber oil. MS (ES+) 433.2(M+H)$^+$.

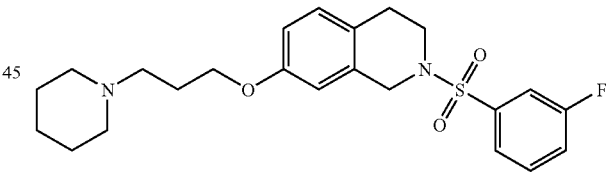

EXAMPLE 305

2-(3-Fluoro-benzenesulfonyl)-7-(3-piperidin-1-yl-propoxy)-1,2,3,4-tetrahydro-isoquinoline: 2-(3-Fluoro-benzenesulfonyl)-7-(3-piperidin-1-yl-propoxy)-1,2,3,4-tetrahydro-isoquinoline is prepared from 7-(3-piperidin-1-yl-propoxy)-1,2,3,4-tetrahydro-isoquinoline dihydrochloride (104 mg, 0.3 mmol), NEt$_3$ (0.14 mL, 1.1 mmol), and 3-fluorobenzenesulfonyl chloride (80 mg, 0.41 mmol) via a procedure substantially analogous to Procedure F except that an additional SCX column purification step is performed to give the free base product (90 mg, 70% yld) as an off-white solid. MS (ES+) 433.2(M+H)$^+$.

6-OH tetrahydroisoquinoline series

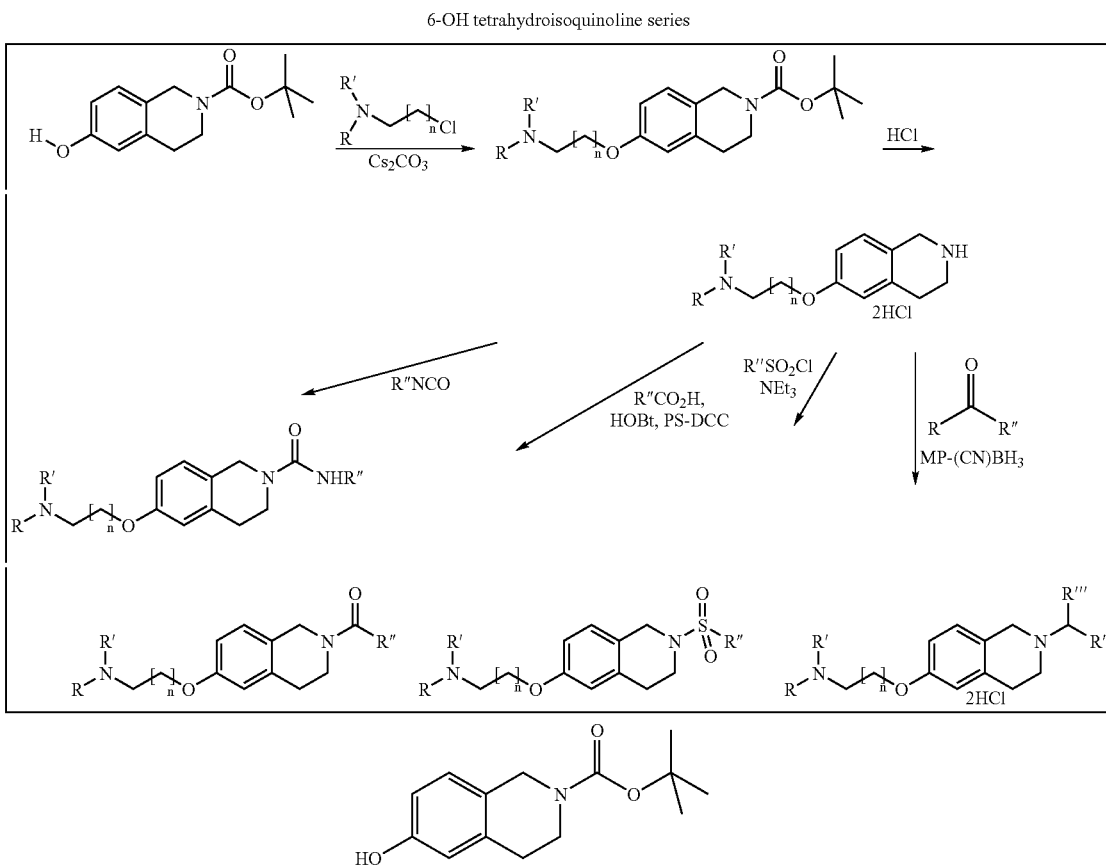

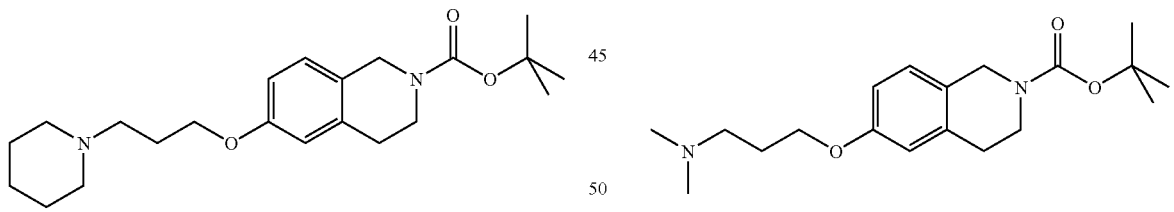

6-hydroxy-3,4-dihydro-1H-isoquinoline-2-carboxylic acid tert-butyl ester is prepared by the procedures similar to those described in Selnick, H. G.; Smith, G. R.; Tebben, A. J.; *Synth.Commun.* 1995, 25, 3255-3262.

EXAMPLE 127

6-(3-Piperidin-1-yl-propoxy)-3,4-dihydro-1H-isoquinoline-2-carboxylic acid tert-butyl ester: To a round-bottom flask, equipped with stir bar and septum, is placed 6-hydroxy-3,4-dihydro-1H-isoquinoline-2-carboxylic acid tert-butyl ester (1 g, 4.01 mmol), KI (599 mg, 4.01 mmol) and NaH (162 mg, 95% dry, 6.42 mmol). Then, dry DMF (20 mL, 0.5 M) is added via syringe followed by N-(3-chloropropyl)piperidine (0.85 mL, 5.2 mmol). The reaction is allowed to stir at 70 degrees overnight. In the morning, the reaction is quenched with water, extracted into EtOAc (3×20 mL) and dried over brine. Column chromatography in 9:1 DCM:MeOH affords 6-(3-piperidin-1-yl-propoxy)-3,4-dihydro-1H-isoquinoline-2-carboxylic acid tert-butyl ester an orange oil (1 g, 67%). Mass sec hit M+1, 375; LCMS>95% @230 nm and ELSD.

In a similar manner the Examples 35, 139, and 164 are prepared:

EXAMPLE 35

6-(3-Dimethylamino-propoxy)-3,4-dihydro-1H-isoquinoline-2-carboxylic acid tert-butyl ester; M+1 335

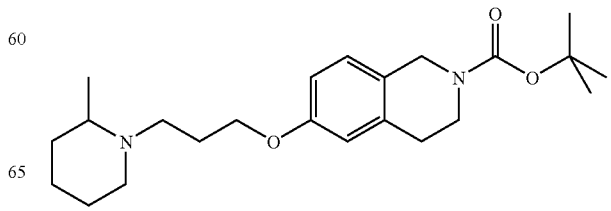

EXAMPLE 139

6-[3-(2-Methyl-piperidin-1-yl)-propoxy]-3,4-dihydro-1H-isoquinoline-2-carboxylic acid tert-butyl ester; M+1 389

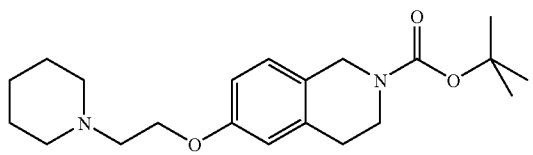

EXAMPLE 164

6-(2-Piperidin-1-yl-ethoxy)-3,4-dihydro-1H-isoquinoline-2-carboxylic acid tert-butyl ester; M+1 361.

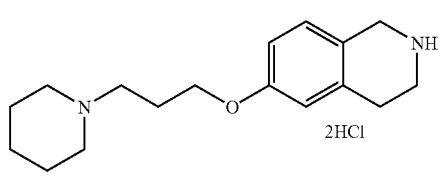

EXAMPLE 128

6-(3-Piperidin-1-yl-propoxy)-1,2,3,4-tetrahydro-isoquinoline dihydrochloride: To a round-bottom flask, equipped with stir bar and septum, is placed 6-(3-piperidin-1-yl-propoxy)-3,4-dihydro-1H-isoquinoline-2-carboxylic acid tert-butyl ester (1 g, 2.6 mmol), DCM (20 mL) and 4M HCl/dioxane (5 mL). The reaction is allowed to stir at room temperature for 3 h. After this time, the reaction is concentrated, dissolved in MeOH and concentrated again affording 6-(3-piperidin-1-yl-propoxy)-1,2,3,4-tetrahydro-isoquinoline dihydrochloride as a white solid (800 mg, 87%). Mass spec hit M+1, 275; LCMS>95% @ 230 nm and ELSD.

In a similar manner the Examples 40, 140, and 165 are prepared:

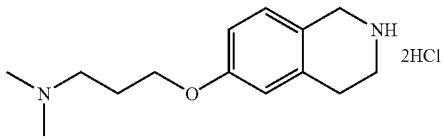

EXAMPLE 40

Dimethyl-[3-(1,2,3,4-tetrahydro-isoquinolin-6-yloxy)-propyl]-amine dihydrochloride; M+1 235.

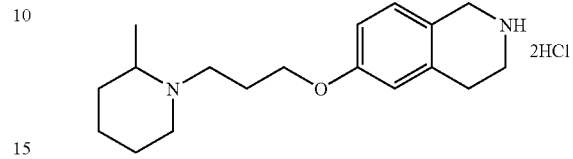

EXAMPLE 140

6-[3-(2-Methyl-piperidin-1-yl)-propoxy]-1,2,3,4-tetrahydro-isoquinoline dihydrochloride; M+1 289.

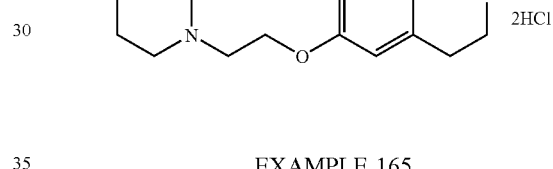

EXAMPLE 165

6-(2-Piperidin-1-yl-ethoxy)-1,2,3,4-tetrahydro-isoquinoline dihydrochloride; M+1 261.

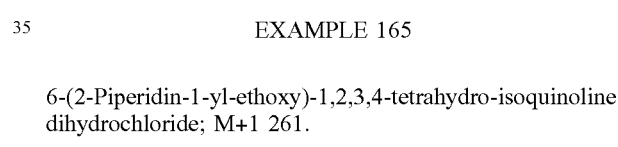

EXAMPLE 129

2-Ethyl-6-(3-piperidin-1-yl-propoxy)-1,2,3,4-tetrahydro-isoquinoline: To a 25 mL round-bottom flask is placed 6-(3-Piperidin-1-yl-propoxy)-1,2,3,4-tetrahydro-isoquinoline dihydrochloride (700 mg, 2.01 mol), MP-CNBH$_3$ (2.5 g, 6.05 mmol, 2.42 mmol/g) and DCM/MeOH (9 mL/1 mL). Then, acetaldehyde is added (0.7 mL, 12 mmol) and the reaction is allowed to stir overnight. The reaction is then filtered, washed with DCM/MeOH and concentrated. Column chromatography in 9:1 DCM:MeOH affords 2-ethyl-6-(3-piperidin-1-yl-propoxy)-1,2,3,4-tetrahydro-isoquinoline (493 mg, 71%) of a viscous oil. Mass spec hit M+1, 303; LCMS>95% @ 230 nm and ELSD. Array synthesis followed this general procedure in 4 mL vials to make the following compounds:

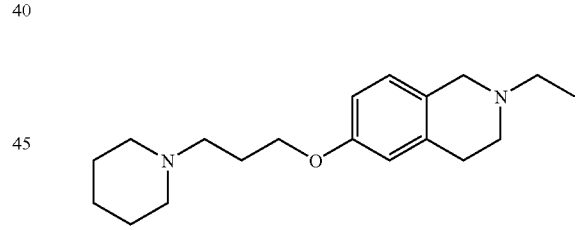

| Example | Name | MS |
|---|---|---|
| 76 | [3-(2-Ethyl-1,2,3,4-tetrahydro-isoquinolin-6-yloxy)-propyl]-dimethyl-amine | 263 |
| 77 | {3-[6-(3-Dimethylamino-propoxy)-3,4-dihydro-1H-isoquinolin-2-yl]-propyl}-dimethyl-amine | 320 |
| 80 | 2-[6-(3-Dimethylamino-propoxy)-3,4-dihydro-1H-isoquinolin-2-yl]-acetamide | 292 |
| 81 | Dimethyl-{3-[2-(2-piperidin-1-yl-ethyl)-1,2,3,4-tetrahydro-isoquinolin-6-yloxy]-propyl}-amine | 346 |
| 82 | Dimethyl-[3-(2-pyridin-3-ylmethyl-1,2,3,4-tetrahydro-isoquinolin-6-yloxy)-propyl]-amine | 326 |
| 83 | Dimethyl-[3-(2-pyridin-2-ylmethyl-1,2,3,4-tetrahydro-isoquinolin-6-yloxy)-propyl]-amine | 326 |
| 141 | 2-Ethyl-6-[3-(2-methyl-piperidin-1-yl)-propoxy]-1,2,3,4-tetrahydro-isoquinoline | 317 |
| 145 | 2-Cyclopropylmethyl-6-(3-piperidin-1-yl-propoxy)-1,2,3,4-tetrahydro-isoquinoline | 329 |
| 146 | 2-Cyclopentylmethyl-6-(3-piperidin-1-yl-propoxy)-1,2,3,4-tetrahydro-isoquinoline | 357 |
| 147 | 2-Cyclohexylmethyl-6-(3-piperidin-1-yl-propoxy)-1,2,3,4-tetrahydro-isoquinoline | 371 |
| 148 | 2-(2-Ethyl-butyl)-6-(3-piperidin-1-yl-propoxy)-1,2,3,4-tetrahydro-isoquinoline | 359 |
| 149 | 6-(3-Piperidin-1-yl-propoxy)-2-propyl-1,2,3,4-tetrahydro-isoquinoline | 317 |
| 166 | 2-Ethyl-6-(2-piperidin-1-yl-ethoxy)-1,2,3,4-tetrahydro-isoquinoline | 289 |
| 169 | 2-Cyclopropylmethyl-6-(2-piperidin-1-yl-ethoxy)-1,2,3,4-tetrahydro-isoquinoline | 315 |
| 170 | 2-Cyclopentylmethyl-6-(2-piperidin-1-yl-ethoxy)-1,2,3,4-tetrahydro-isoquinoline | 343 |
| 171 | 2-Cyclohexylmethyl-6-(2-piperidin-1-yl-ethoxy)-1,2,3,4-tetrahydro-isoquinoline | 357 |
| 172 | 2-(2-Ethyl-butyl)-6-(2-piperidin-1-yl-ethoxy)-1,2,3,4-tetrahydro-isoquinoline | 345 |
| 168 | 2-Isopropyl-6-(2-piperidin-1-yl-ethoxy)-1,2,3,4-tetrahydro-isoquinoline | 303 |

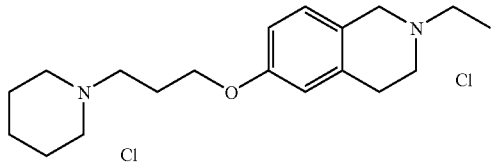

EXAMPLE 250

2-Ethyl-6-(3-piperidin-1-yl-propoxy)-1,2,3,4-tetrahydro-isoquinoline dihydrochloride: 2-Ethyl-6-(3-piperidin-1-yl-propoxy)-1,2,3,4-tetrahydro-isoquinoline (5.12 g, 16.9 mmol) is dissolved in MeOH (50 mL), and 1M HCl in ether is added dropwise (37.2 mL, 37.2 mmol) and the mixture is stirred for 10 minutes and concentrated to give the dihydrochloride salt as a white solid (6.0 g, 93%).

EXAMPLE 143

2-Isopropyl-6-[3-(2-methyl-piperidin-1-yl)-propoxy]-1,2,3,4-tetrahydro-isoquinoline: To a flask equipped with a stir bar is placed 6-[3-(2-Methyl-piperidin-1-yl)-propoxy]-1,2,3,4-tetrahydro-isoquinoline dihydrochloride (300 mg, 0.83 mmol), acetone (excess), NaCNBH$_3$ (155 mg, 2.5 mmol) in MeOH (8 mL) and the mixture stirred at room temperature for 2 h. The reaction mixture is diluted with water, and extracted with CH$_2$Cl$_2$. The organic phase is dried over Na$_2$SO$_4$ and concentrated. M+1 331, LCMS >98% @ 230 nm and ELSD.

In a similar manner Example 138 is prepared:

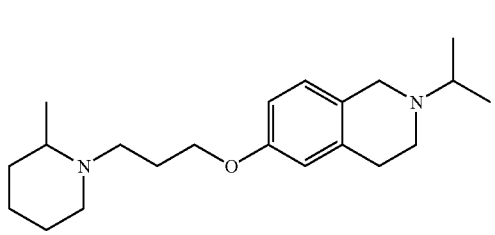

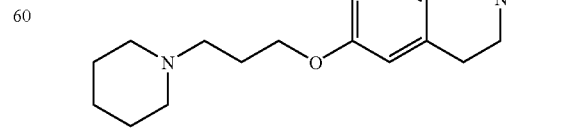

EXAMPLE 138

2-Isopropyl-6-(3-piperidin-1-yl-propoxy)-1,2,3,4-tetrahydro-isoquinoline; M+1 317, LCMS 100% @ 230 nm and ELSD.

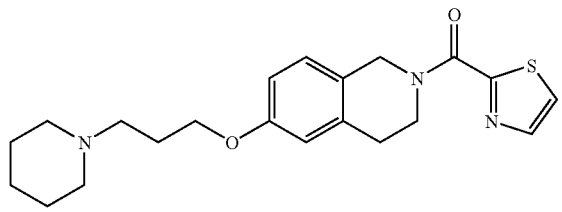

EXAMPLE 162

[6-(3-Piperidin-1-yl-propoxy)-3,4-dihydro-1H-isoquinolin-2-yl]-thiazol-2-yl-methanone: To a 4 mL vial is placed 6-(3-piperidin-1-yl-propoxy)-1,2,3,4-tetrahydro-isoquinoline dihydrochloride (28 mg, 0.08 mmol), resin-bound DCC (134 mg, 0.16 mmol, 1.2 mmol/g), HOBt (16 mg, 0.12 mmol), pyrazole carboxylic acid (13 mg, 0.1 mmol) and a 5:1:1 mixture of $CHCl_3:CH_3CN:tBuOH$. The vial is agitated by means of a lab quake shaker overnight. In the morning, PS-trisamine (134 mg, 0.4 mmol, 3.0 mmol/g) is added and the reaction is again allowed to rotate overnight to scavenge excess carboxylic acid and HOBt. Filtration, washing with DCM/MeOH and concentration affords a orange foam. Filtration through a short pipet column provides 24 mg (80%) of [6-(3-piperidin-1-yl-propoxy)-3,4-dihydro-1H-isoquinolin-2-yl]-thiazol-2-yl-methanone as an orange solid. Mass spec hit M+1, 386; LCMS>95% @ 230 nm and ELSD. Array synthesis follows this general procedure in 4 mL vials to make the following examples:

| Example | Name | MS |
|---|---|---|
| 78 | [6-(3-Dimethylamino-propoxy)-3,4-dihydro-1H-isoquinolin-2-yl]-(1-phenyl-5-trifluoromethyl-1H-pyrazol-4-yl)-methanone | 474 |
| 134 | 1-[6-(3-Piperidin-1-yl-propoxy)-3,4-dihydro-1H-isoquinolin-2-yl]-ethanone | 315 |
| 156 | [6-(3-Piperidin-1-yl-propoxy)-3,4-dihydro-1H-isoquinolin-2-yl]-(tetrahydro-furan-2-yl)-methanone | 386 |
| 157 | (5-Methyl-furan-2-yl)-[6-(3-piperidin-1-yl-propoxy)-3,4-dihydro-1H-isoquinolin-2-yl]-methanone | 383 |
| 158 | [6-(3-Piperidin-1-yl-propoxy)-3,4-dihydro-1H-isoquinolin-2-yl]-(1H-pyrrol-2-yl)-methanone | 368 |
| 159 | 2-Methylsulfanyl-1-[6-(3-piperidin-1-yl-propoxy)-3,4-dihydro-1H-isoquinolin-2-yl]-ethanone | 363 |
| 160 | [6-(3-Piperidin-1-yl-propoxy)-3,4-dihydro-1H-isoquinolin-2-yl]-thiophen-2-yl-methanone | 385 |
| 161 | N,N-Dimethyl-4-oxo-4-[6-(3-piperidin-1-yl-propoxy)-3,4-dihydro-1H-isoquinolin-2-yl]-butyramide | 402 |
| 162 | [6-(3-Piperidin-1-yl-propoxy)-3,4-dihydro-1H-isoquinolin-2-yl]-thiazol-2-yl-methanone | 386 |
| 163 | 5-[6-(3-Piperidin-1-yl-propoxy)-3,4-dihydro-1H-isoquinoline-2-carbonyl]-pyrrolidin-2-one | 386 |
| 175 | 2-Dimethylamino-1-[6-(3-piperidin-1-yl-propoxy)-3,4-dihydro-1H-isoquinolin-2-yl]-ethanone | 360 |
| 176 | (1-Methyl-pyrrolidin-2-yl)-[6-(3-piperidin-1-yl-propoxy)-3,4-dihydro-1H-isoquinolin-2-yl]-methanone | 386 |
| 177 | 2-Dimethylamino-1-[6-(2-piperidin-1-yl-ethoxy)-3,4-dihydro-1H-isoquinolin-2-yl]-ethanone | 346 |
| 182 | 1-[6-(3-Piperidin-1-yl-propoxy)-3,4-dihydro-1H-isoquinolin-2-yl]-propan-1-one | 332 |
| 183 | Cyclopropyl-[6-(3-piperidin-1-yl-propoxy)-3,4-dihydro-1H-isoquinolin-2-yl]-methanone | 344 |
| 184 | Cyclobutyl-[6-(3-piperidin-1-yl-propoxy)-3,4-dihydro-1H-isoquinolin-2-yl]-methanone | 358 |
| 185 | Cyclopentyl-[6-(3-piperidin-1-yl-propoxy)-3,4-dihydro-1H-isoquinolin-2-yl]-methanone | 372 |
| 186 | 2-Methyl-1-[6-(3-piperidin-1-yl-propoxy)-3,4-dihydro-1H-isoquinolin-2-yl]-propan-1-one | 346 |

| Example | Name | MS |
|---|---|---|
| 187 | Cyclohexyl-[6-(3-piperidin-1-yl-propoxy)-3,4-dihydro-1H-isoquinolin-2-yl]-methanone | 385 |
| 188 | 2-Ethyl-1-[6-(3-piperidin-1-yl-propoxy)-3,4-dihydro-1H-isoquinolin-2-yl]-butan-1-one | 373 |
| 193 | [6-(3-Piperidin-1-yl-propoxy)-3,4-dihydro-1H-isoquinolin-2-yl]-pyridin-4-yl-methanone | 381 |
| 194 | [6-(3-Piperidin-1-yl-propoxy)-3,4-dihydro-1H-isoquinolin-2-yl]-pyridin-3-yl-methanone | 381 |
| 195 | [6-(3-Piperidin-1-yl-propoxy)-3,4-dihydro-1H-isoquinolin-2-yl]-pyridin-2-yl-methanone | 381 |
| 196 | Isoxazol-5-yl-[6-(3-piperidin-1-yl-propoxy)-3,4-dihydro-1H-isoquinolin-2-yl]-methanone | 371 |

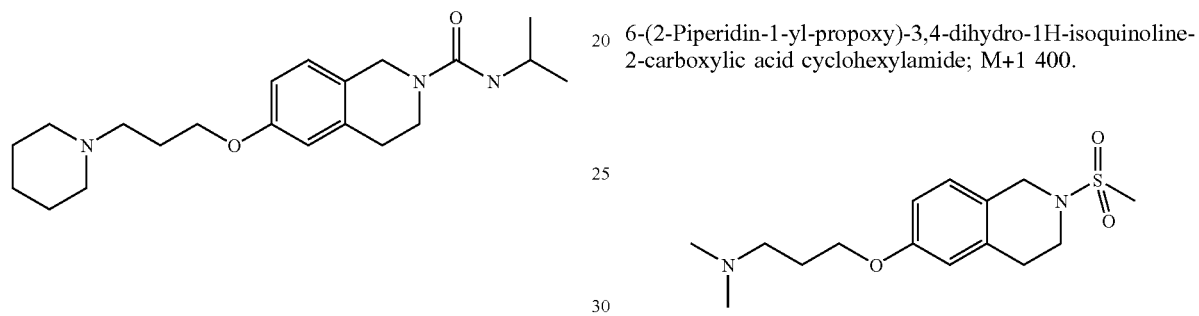

EXAMPLE 178

6-(2-Piperidin-1-yl-propoxy)-3,4-dihydro-1H-isoquinoline-2-carboxylic acid isopropylamide: To a 4 mL vial is placed 6-(3-piperidin-1-yl-propoxy)-1,2,3,4-tetrahydro-isoquinoline dihydrochloride (25.0 mg, 0.07 mmol), resin-bound Hunigs base (81 mg, 0.29 mmol, 3.54 mmol/g), resin bound DMAP (catalytic), and dry CH$_2$Cl$_2$ and isopropyl isocyanate (16 □L, 0.18 mmol). The vial is agitated by means of a lab quake shaker overnight. In the morning, PS-trisamine (120 mg, 0.36 mmol, 3.0 mmol/g) is added and the reaction again allowed to rotate for 4 hours to scavenge excess isocyanate., Filtration, washing with CH$_2$Cl$_2$ and concentration afforded the desired urea. M+1 360.

In a similar manner Examples 179 is prepared:

EXAMPLE 179

6-(2-Piperidin-1-yl-propoxy)-3,4-dihydro-1H-isoquinoline-2-carboxylic acid cyclohexylamide; M+1 400.

EXAMPLE 79

[3-(2-Methanesulfonyl-1,2,3,4-tetrahydro-isoquinolin-6-yloxy)-propyl]-dimethyl-amine: To a 4 mL vial is placed Dimethyl-[3-(1,2,3,4-tetrahydro-isoquinolin-6-yloxy)-propyl]-amine (24.0 mg, 0.1 mmol), resin-bound DIEA (58 mg, 0.2 mmol, 3.54 mmol/g), MsCl (12 □L, 0.15 mmol) and dry CH$_2$Cl$_2$ (2 mL). The vial is allowed to rotate overnight. In the morning, PS-trisamine (136 mg, 0.41 mmol, 3.0 mmol/g) is added and the reaction again allowed to rotate for 4 hours to scavenge excess MsCl. Filtration, washing with CH$_2$Cl$_2$ and concentration affords the desired urea LCMS>99% @ 230 nm and ELSD, M+1 360.

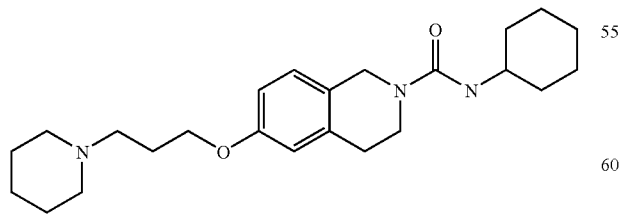

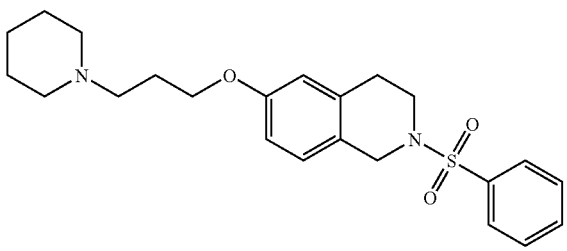

EXAMPLE 302

2-Benzenesulfonyl-6-(3-piperidin-1-yl-propoxy)-1,2,3,4-tetrahydro-isoquinoline: 2-Benzenesulfonyl-6-(3-piperidin-1-yl-propoxy)-1,2,3,4-tetrahydro-isoquinoline is prepared from 6-(3-piperidin-1-yl-propoxy)-1,2,3,4-tetrahydro-isoquinoline dihydrochloride (330 mg, 0.95 mmol), NEt$_3$ (0.48 mL, 3.5 mmol), and benzenesulfonyl chloride (0.15 mL, 1.17 mmol) via a procedure substantially analogous to Procedure F except that an additional SCX column purification step is performed to give the product as a white solid (250 mg, 63% yld). MS(ES+) 415.3(M+H)⁺.

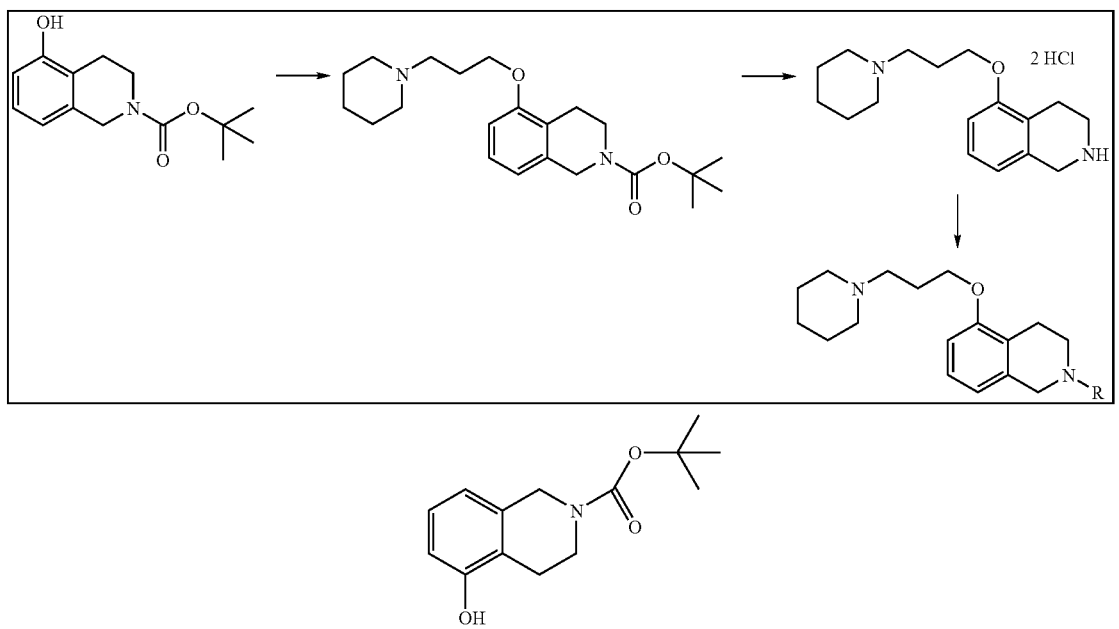

5-OH tetrahydroisoquinoline series

5-Hydroxy-3,4-dihydro-1-H-isoquinoline-2-carboxylic acid tert-butyl ester is prepared by the procedures similar to those described in Durand S.; Lusinchi, X.; Moreau, R. C. *Bull. Soc. Chim. France* 1961, 207, 270; and Georgian, V.; Harrison, R. J.; Skaletzky, L. L.; *J Org Chem* 1962, 27, 4571.

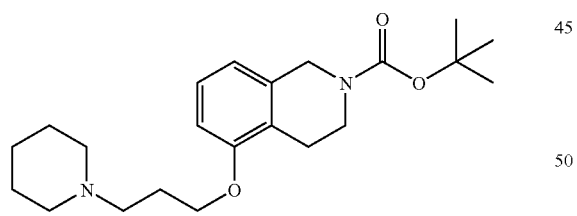

EXAMPLE 290

5-(3-Piperidin-1-yl-propoxy)-3,4-dihydro-1H-isoquinoline-2-carboxylic acid tert-butyl ester is prepared from 5-Hydroxy-3,4-dihydro-1-H-isoquinoline-2-carboxylic acid tert-butyl ester (5.69 g, 22.8 mmol) in a manner substantially analogous to Procedure A except DMF is used in place of dioxane. Following aqueous workup, the crude material is purified by flash chromatography [Biotage 65M SiO₂, elute 10% (25/5/1 CHCl₃/MeOH/NH₄OH)/90% (10% MeOH/CHCl₃)] to give the title compound (5.2 g, 61%). MS (ES+) 375.3

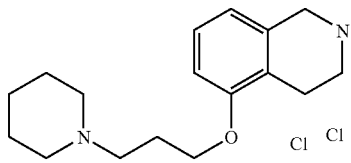

EXAMPLE 291

5-(3-Piperidin-1-yl-propoxy)-1,2,3,4-tetrahydro-isoquinoline dihydrochloride salt is prepared from 5-(3-Piperidin-1-yl-propoxy)-3,4-dihydro-1H-isoquinoline-2-carboxylic acid tert-butyl ester (4.0 g, 10.7 mmol) in a manner substantially analogous to Procedure B to give the title compound as an off-white solid (3.47 g, 93%). MS (ES+) 275.2

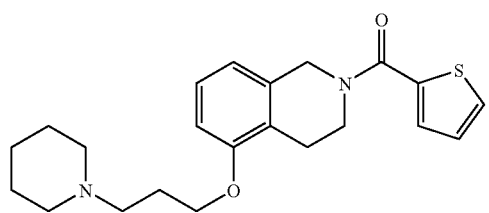

EXAMPLE 309

[5-(3-Piperidin-1-yl-propoxy)-3,4-dihydro-1H-isoquinolin-2-yl]-thiophen-2-yl-methanone is prepared from 5-(3-Piperidin-1-yl-propoxy)-1,2,3,4-tetrahydro-isoquinoline dihydrochloride salt (0.256 g, 0.74 mmol) in a manner substantially analogous to Procedure E to give the title compound as an off-white solid (0.109 g, 38%). MS (ES+) 415.2

EXAMPLE 306

2-Ethyl-5-(3-piperidin-1-yl-propoxy)-1,2,3,4-tetrahydro-isoquinoline is prepared from 5-(3-Piperidin-1-yl-propoxy)-1,2,3,4-tetrahydro-isoquinoline dihydrochloride salt (375 mg, 1.1 mmol) in a manner substantially analogous to Procedure C to give the title compound as a yellow oil (49 mg, 15%). MS (ES+) 303.3

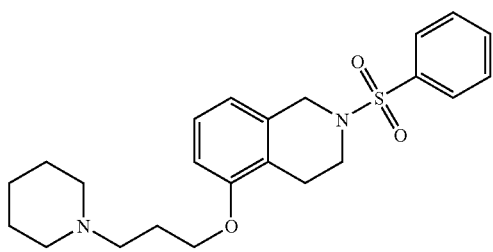

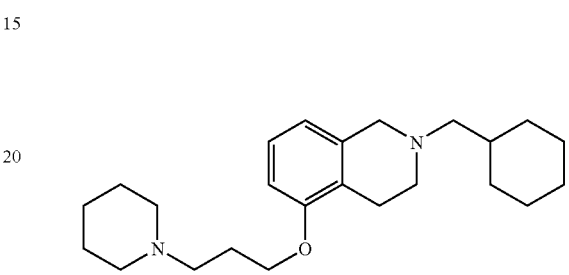

EXAMPLE 294

2-Benzenesulfonyl-5-(3-piperidin-1-yl-propoxy)-1,2,3,4-tetrahydro-isoquinoline is prepared from 5-(3-Piperidin-1-yl-propoxy)-1,2,3,4-tetrahydro-isoquinoline dihydrochloride salt (150 mg, 0.43 mmol) via a procedure substantially analogous to Procedure F to provide the title compound as an off-white solid (54 mg, 30%). MS (ES+) 385.2

EXAMPLE 313

2-Cyclohexylmethyl-5-(3-piperidin-1-yl-propoxy)-1,2,3,4-tetrahydro-isoquinoline is prepared from 5-(3-piperidin-1-yl-propoxy)-1,2,3,4-tetrahydro-isoquinoline dihydrochloride salt (350 mg, 1.0 mmol) in a manner substantially analogous to Procedure C to give the title compound as a yellow oil (0.142 mg, 38%). MS (ES+) 371.4

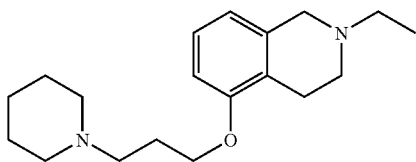

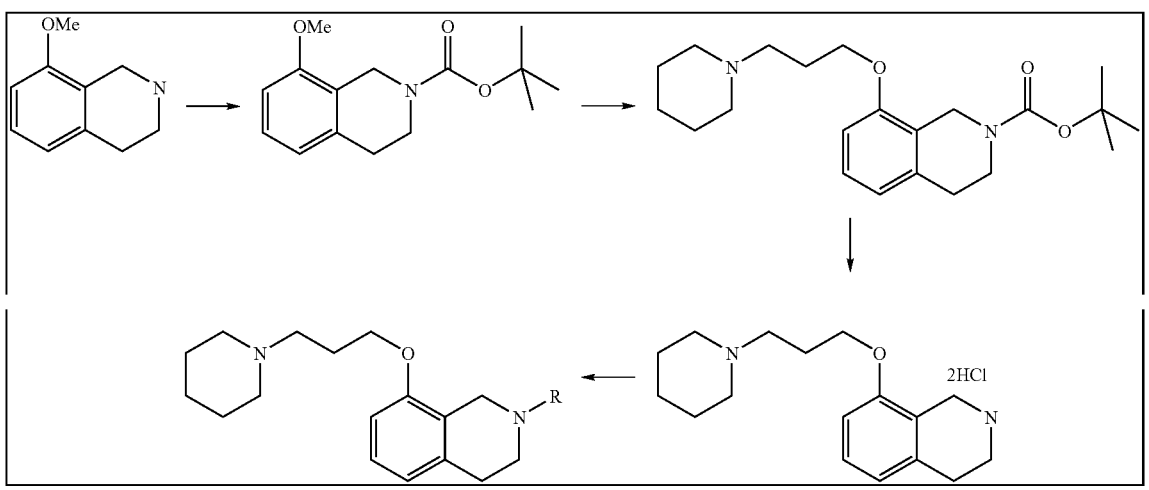

8-OH tetrahydroisoquinoline series

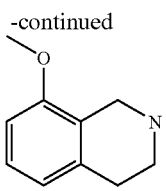

8-Methoxy-1,2,3,4-tetrahydro-isoquinoline is prepared according to Shanker, P. S.; Subba Rao, G. S. R. *Indian J. of Chemistry section B* 1993, 32B, 1209-1213.

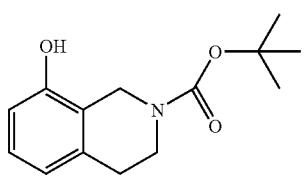

8-Hydroxy-3,4-dihydro-1H-isoquinoline-2-carboxylic acid tert-butyl ester: To a mixture of 8-methoxy-1,2,3,4-tetrahydro-isoquinoline (2.54 g, 15.6 mmol) in CH$_2$Cl$_2$ (60 mL) at −78° C. is added a solution of boron tribromide in CH$_2$Cl$_2$ (1 M, 52 mL, 52 mmol) dropwise over approximately 20 minutes. The cooling bath is removed, and the mixture is warmed to room temperature. After 4 h, the reaction is carefully quenched with ice. EtOAc and water is added, and the mixture is stirred overnight. The phases are separated, and 5 N NaOH solution is added to the aqueous phase until pH is basic. Dioxane (250 mL) and di-tert-butyl dicarbonate (6.78 g, 31 mmol) is added, and reaction mixture is stirred at room temperature overnight. EtOAc is added, and the phases are separated. The aqueous phase is extracted with EtOAc (1×), and the combined organic phase is washed with brine and dried (MgSO$_4$). After filtration, the solvent is removed in vacuo to provide the title compound (4.84 g) that is used without purification. MS (ES−) 248.2.

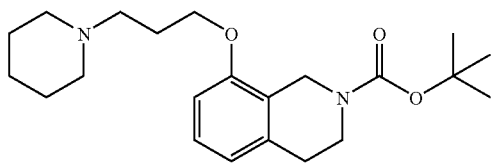

EXAMPLE 307

8-(3-Piperidin-1-yl-propoxy)-3,4-dihydro-1H-isoquinoline-2-carboxylic acid tert-butyl ester is prepared from 8-hydroxy-3,4-dihydro-1H-isoquinoline-2-carboxylic acid tert-butyl ester (0.84 g, 3.4 mmol) in a manner substantially analogous to Procedure A except DMF is used in place of dioxane. Following aqueous workup, the crude material is purified by chromatography [SCX-MeOH wash, elute 2M NH$_3$/MeOH then Biotage 40s SiO$_2$, elute 10% (25/5/1 CHCl$_3$/MeOH/NH$_4$OH)/90% (10% MeOH/CHCl$_3$)] to give the title compound (0.61 g, 48%). MS (ES+) 375.3.

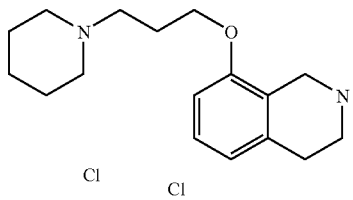

EXAMPLE 308

8-(3-Piperidin-1-yl-propoxy)-1,2,3,4-tetrahydro-isoquinoline dihydrochloride salt is prepared from 8-(3-piperidin-1-yl-propoxy)-3,4-dihydro-1H-isoquinoline-2-carboxylic acid tert-butyl ester (3.09 g, 8.25 mmol) in a manner substantially analogous to Procedure B to give the title compound as an off-white solid (2.63 g, 85%). MS (ES+) 275.3

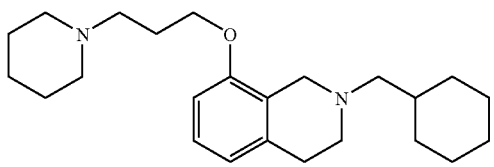

EXAMPLE 309

2-Cyclohexylmethyl-8-(3-piperidin-1-yl-propoxy)-1,2,3,4-tetrahydro-isoquinoline is prepared from 8-(3-piperidin-1-yl-propoxy)-1,2,3,4-tetrahydro-isoquinoline dihydrochloride salt (0.375 g, 1.1 mmol) in a manner substantially analogous to Procedure C to give the title compound as a yellow oil (0.195 g, 48%). MS (ES+) 371.4

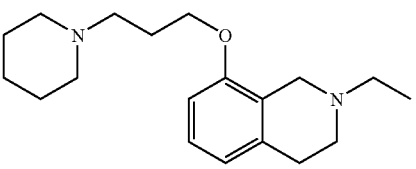

EXAMPLE 310

2-Ethyl-8-(3-piperidin-1-yl-propoxy)-1,2,3,4-tetrahydro-isoquinoline is prepared from 8-(3-piperidin-1-yl-propoxy)-1,2,3,4-tetrahydro-isoquinoline dihydrochloride salt (0.375 g, 1.1 mmol) in a manner substantially analogous to Procedure C to give the title compound as a yellow oil (0.124 g, 37%). MS (ES+) 303.3.

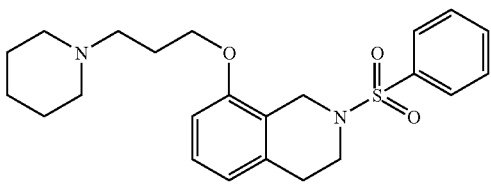

EXAMPLE 311

2-Benzenesulfonyl-8-(3-piperidin-1-yl-propoxy)-1,2,3,4-tetrahydro-isoquinoline is prepared from 8-(3-piperidin-1-yl-propoxy)-1,2,3,4-tetrahydro-isoquinoline dihydrochloride salt (300 mg, 0.86 mmol) via a procedure substantially analogous to Procedure F to provide the title compound as an off-white solid (0.22 g, 63%). MS (ES+) 415.3.

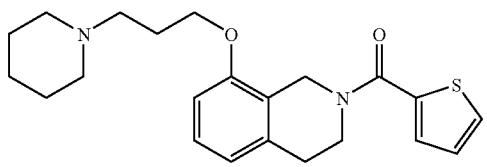

EXAMPLE 312

[8-(3-Piperidin-1-yl-propoxy)-3,4-dihydro-1H-isoquinolin-2-yl]-thiophen-2-yl-methanone: To a mixture of 8-(3-piperidin-1-yl-propoxy)-1,2,3,4-tetrahydro-isoquinoline dihydrochloride salt (300 mg, 0.86 mmol) and NEt₃ (0.36 mL, 2.6 mmol) in CH₂Cl₂ (10 mL) is added 2-thiophene carbonyl chloride (0.10 mL, 0.95 mmol). After stirring at room temperature overnight, the mixture is partitioned between EtOAc and water. The organic phase is washed with brine, dried (MgSO₄), and concentrated. The residue is purified by flash chromatography [Biotage 40S SiO₂, elute 20% (90/10/1 CH₂Cl₂/MeOH/NH₄OH)/80% CH₂Cl₂ to 100% (90/10/1 CH₂Cl₂/MeOH/NH₄OH)] to yield the title compound as a yellow oil (0.181 g, 55%). MS (ES+) 385.3.

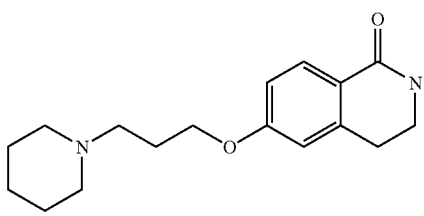

EXAMPLE 206

6-(3-Piperidin-1-yl-propoxy)-3,4-dihydro-2H-isoquinolin-1-one is prepared from 6-hydroxy-3,4-dihydro-2H-isoquinolin-1-one (CAS Registry Number 22245-98-3) (0.5 g, 2.9 mmol) in a manner substantially analogous to Procedure A except DMF is used in place of dioxane. Following aqueous workup, the crude material is purified by flash chromatography (Biotage 40M SiO₂, elute 90/10/1 CH₂Cl₂/ MeOH/NH₄OH) to give the title compound as a white solid (0.516 g, 61%). MS (ES+) 289.1

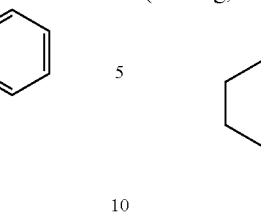

EXAMPLE 207

7-(3-Piperidin-1-yl-propoxy)-3,4-dihydro-2H-isoquinolin-1-one is prepared from 7-hydroxy-3,4-dihydro-2H-isoquinolin-1-one (CAS Registry Number 22246-05-5) (1.43 g, 8.76 mmol) in a manner substantially analogous to Procedure A except DMF is used in place of dioxane. Following aqueous workup, the crude material is purified by flash chromatography (Biotage 40M SiO₂, elute 90/10/1 CH₂Cl₂/ MeOH/NH₄OH) to give the title compound as a white solid (1.11 g, 44%). MS (ES+) 289.1

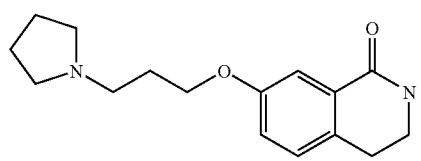

EXAMPLE 205

7-(3-Pyrrolidin-1-yl-propoxy)-3,4-dihydro-2H-isoquinolin-1-one is prepared from 7-hydroxy-3,4-dihydro-2H-isoquinolin-1-one (0.48 g, 2.94 mmol) in a manner substantially analogous to Procedure A except DMF is used in place of dioxane and 1-(3-Chloro-propyl)-pyrrolidine is used instead of N-(3-chloropropyl)piperidine. Following aqueous workup, the crude material is purified by flash chromatography (Biotage 40M SiO₂, elute 90/10/1 CH₂Cl₂/MeOH/ NH₄OH) to give the title compound as an off-white solid (0.17 g, 21%). MS (ES+) 275.1

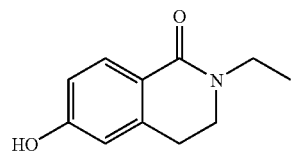

2-Ethyl-6-hydroxy-3,4-dihydro-2H-isoquinolin-1-one:

To a mixture of 6-methoxy-3,4-dihydro-2H-isoquinolin-1-one (0.30 g, 1.69 mmol) in THF (10 mL) is added sodium hydride (60% mineral oil suspension, 100 mg). The suspension is heated at reflux for 1 h, and cooled to room temperature. Ethyl iodide (1.4 mL, 17 mmol) is added, and the mixture is stirred at room temperature overnight. The mixture is partitioned between EtOAc and water. After the aqueous phase is extracted with EtOAc (2×), the combined organic phase is washed with brine and dried (MgSO₄). After removal of the solvent, the residue is purified by flash chromatography (Biotage 40M SiO$_2$, elute 45% EtOAc:hexane–50% EtOAc:hexane, linear gradient) to yield 2-ethyl-6-methoxy-3,4-dihydro-2H-isoquinolin-1-one as a colorless oil (0.275 g, 78%). The material is dissolved in CH$_2$Cl$_2$ (10 mL) and cooled to –78° C. To the cooled mixture is added a solution of boron tribromide (1 M, 4.7 mL, 4.7 mmol) in CH$_2$Cl$_2$. After 0.5 h, the temperature is warmed to 0° C. and stirred for 3 h. After the reaction is carefully quenched with ice, EtOAc and water is added, and the mixture is vigorously stirred overnight. The phases are separated, and the organic phase is extracted with EtOAc (2×). The combined organic phase is washed with brine and dried (MgSO$_4$). The solvent is removed in vacuo, and the residue is purified by chromatography (Varian 10 g SiO$_2$ cartridge, elute 60% EtOAc:hexane) to provide 2-ethyl-6-hydroxy-3,4-dihydro-2H-isoquinolin-1-one (0.209 g, 82%). MS (ES+) 192.0

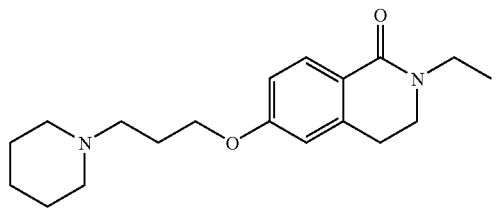

EXAMPLE 265

2-Ethyl-6-(3-piperidin-1-yl-propoxy)-3,4-dihydro-2H-isoquinolin-1-one is prepared from 2-Ethyl-6-hydroxy-3,4-dihydro-2H-isoquinolin-1-one (0.192 g, 1.0 mmol) in a manner substantially analogous to Procedure A except DMF is used in place of dioxane. Following aqueous workup, the crude material is purified by chromatography [Varian 10 g SiO$_2$ cartridge, elute 10% (25/5/1 CHCl$_3$/MeOH/NH$_4$OH)/90% (10% MeOH/CHCl$_3$)] to obtain the title compound as a waxy off-white solid (77 mg, 24%). MS (ES+) 317.1

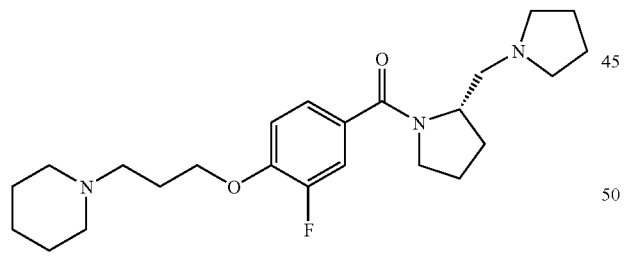

EXAMPLE 303

[3Fluoro-4-(3-piperidin-1-yl-propoxy)-phenyl]-(2-pyrrolidin-1-ylmethyl-pyrrolidin-1-yl)-methanone:

General Procedure G: A mixture of (3-Fluoro-4-hydroxyphenyl)-(2-pyrrolidin-1-ylmethyl-pyrrolidin-1-yl)-methanone (0.193 g, 0.66 Mmol), Cs$_2$CO$_3$ (0.43 g, 1.32 mmol), KI (55 mg, 0.33 mmol), and N-(3-chloropropyl)piperidine (3.9 g, 24 mmol) in DMF (5 mL) is heated at 90° C. overnight. The mixture is partitioned between EtOAc and water. The phases are separated, and the aqueous phase is extracted with EtOAc (2×). The combined organic phase is washed with brine, dried (MgSO$_4$), and concentrated in vacuo. The residue is purified by chromatography [SCX-MeOH wash, elute 2M NH$_3$/MeOH; then Biotage 12M SiO$_2$, elute 10% (25/5/1 CHCl$_3$/MeOH/NH$_4$OH)/90% (10% MeOH/CHCl$_3$)] to give the title compound as a yellow oil (0.105 g, 38%). MS (ES+) 418.4

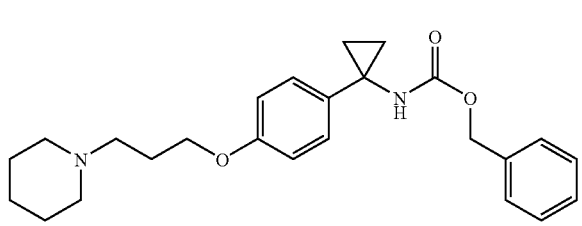

EXAMPLE 240

{1-[4-(3-Piperidin-1-yl-propoxy)-phenyl]-cyclopropyl}-carbamic acid benzyl ester is prepared from [1-(4-Hydroxyphenyl)-cyclopropyl]-carbamic acid benzyl ester (1.21 g, 4.28 mmol), Cs$_2$CO$_3$ (2.78 g, 8.55 mmol), KI (71 mg, 0.43 mmol), and N-(3-chloropropyl)piperidine (0.86 g, 5.34 mmol) in dioxane (50 mL) in a manner substantially analogous to Procedure A to give the product((1.16 g, 66%). MS (ES+) 409.3.

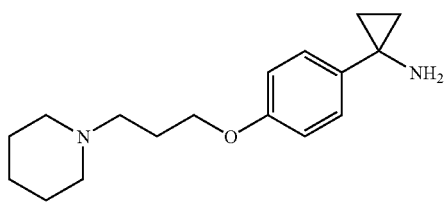

EXAMPLE 241

1-[4-(3-Piperidin-1-yl-propoxy)-phenyl]-cyclopropylamine: {1-[4-(3-Piperidin-1-yl-propoxy)-phenyl]-cyclopropyl}-carbamic acid benzyl ester (1.08 g, 2.65 mmol) is dissolved in ethanol (50 mL), and 10% Pd/C is added (200 mg). The mixture was stirred under a balloon on hydrogen for 3 hours. The reaction mixture was stirred through a plug of silica gel to give the desired compound. HRMS 275.2123 (M+H)$^+$.

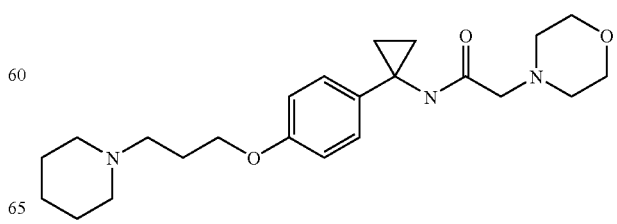

EXAMPLE 247

2-Morpholin-4-yl-N-{1-[4-(3-piperidin-1-yl-propoxy)-phenyl]-cyclopropyl}-acetamide: 1-[4-(3-Piperidin-1-yl-propoxy)-phenyl]-cyclopropylamine (0.195 g, 0.72 mmol) and morpholin-4-yl-acetic acid (0.125 g, 0.86 mmol) are dissolved in DMF, and diisopropylethylamine added (0.15 mL), followed by EDC (0.165 g, 0.86 mmol) and HOBt (0.116 g, 0.86 mmol). The reaction mixture was stirred overnight at room temperature. The residue is purified by chromatography [SCX-MeOH wash, elute 2M NH$_3$/MeOH; then Biotage 12M SiO$_2$, elute 10% (25/5/1 CHCl$_3$/MeOH/NH$_4$OH)/90% (10% MeOH/CHCl$_3$)] to give the title compound as a yellow oil. HRMS 402.2765 (M+H)$^+$.

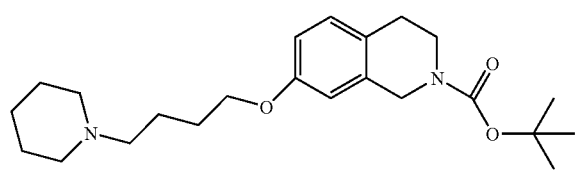

EXAMPLE 316

7-(4-Piperidin-1-yl-butoxy)-3,4-dihydro-1H-isoquinoline-2-carboxylic acid tert-butyl ester: A 20 mL DMF mixture of 7-(4-chloro-butoxy)-3,4-dihydro-1-H-isoquinoline-2-carboxylic acid tert-butyl ester (1.0 g, 3 mmol), piperidine (0.75 mL, 7.5 mmol), and KI (1.0 g, 6 mmol) is stirred at 50° C. under N$_2$ for four hours, then at room temperature for 16 hours. The reaction mixture is directly purified by chromatography (SCX-MeOH wash, elute 2M NH3/MeOH; then SiO$_2$; 0-6% MeOH|CH$_2$Cl$_2$/1% NH$_4$OH gradient) to give the free base (700 mg, 60% yld). MS(ES+)389.3 (M+H)$^+$ free base.

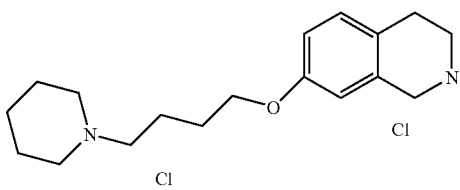

EXAMPLE 314

7-(4-Piperidin-1-yl-butoxy)-1,2,3,4-tetrahydro-isoquinoline dihydrochloride: 7-(4-Piperidin-1-yl-butoxy)-1,2,3,4-tetrahydro-isoquinoline dihydrochloride is prepared from 7-(4-chloro-butoxy)-3,4-dihydro-1-H-isoquinoline-2-carboxylic acid tert-butyl ester (600 mg, 1.5 mmol) and 4N HCl/dioxane (2.5 mL, 10 mmol) base in a manner substantially analogous to Procedure B to give the product (490 mg, 90% yld). MS(ES+)389.3 (M+H)$^+$ free

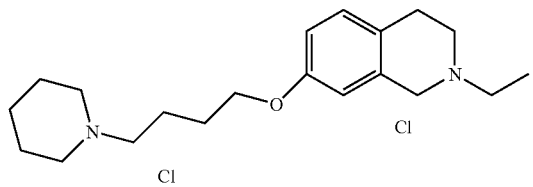

EXAMPLE 315

2-Ethyl-7-(4-piperidin-1-yl-butoxy)-1,2,3,4-tetrahydro-isoquinoline dihydrochloride: 2-Ethyl-7-(4-piperidin-1-yl-butoxy)-1,2,3,4-tetrahydro-isoquinoline dihydrochloride is prepared from 7-(4-piperidin-1-yl-butoxy)-1,2,3,4-tetrahydro-isoquinoline dihydrochloride (252 mg, 0.7 mmol), and acetaldehyde (0.40 mL, 7 mmol) in a manner substantially analogous to Procedure C to give the dihydrochloride product as an off white solid (125 mg, 70% yld). MS(ES+)317.2 (M+H)$^+$ free base.

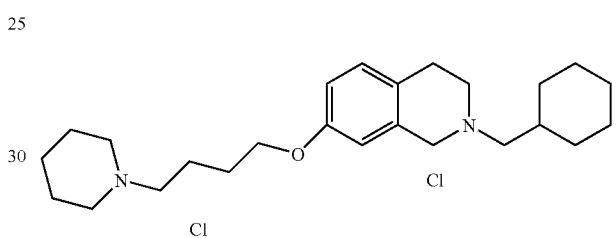

EXAMPLE 317

2-Cyclohexylmethyl-7-(4-piperidin-1-yl-butoxy)-1,2,3,4-tetrahydro-isoquinoline dihydrochloride: 2-Cyclohexylmethyl-7-(4-piperidin-1-yl-butoxy)-1,2,3,4-tetrahydro-isoquinoline dihydrochloride is prepared from 7-(4-piperidin-1-yl-butoxy)-1,2,3,4-tetrahydro-isoquinoline dihydrochloride (175 mg, 0.48 mmol), and cyclohexanecarboxaldehyde (0.35 mL, 2.9 mmol) in a manner substantially analogous to Procedure C to give the dihydrochloride product as an off white solid (105 mg, 62% yld). MS(ES+)385.3 (M+H)$^+$ free base.

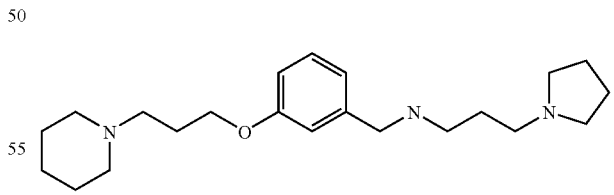

EXAMPLE 208

[3-(3-Piperidin-1-yl-propoxy)-benzyl]-(3-pyrrolidin-1-yl-propyl)-amine: The reductive amination is run with 3-(3-piperidin-1-yl-propoxy)-benzaldehyde (1 g, 4 mmol) and), 3-pyrrolridin-1-yl propylamine (1 mL, 8 mmol), and MP-CNBH$_3$ resin(4.5 g, 10.4 mmol) via a procedure substantially analogous to [2-(3-piperidin-1-yl-propoxy)-benzyl]-

(3-pyrrolidin-1-yl-propyl)-amine to give the product as a yellow oil (818 mg, 58% yld). MS(ES+)360.3(M+H)+ free bas.

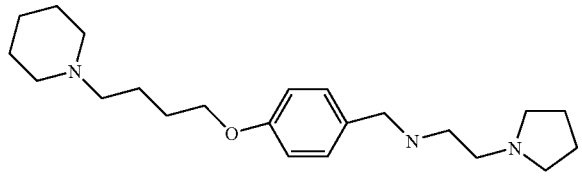

EXAMPLE 202

[4-(4-Piperidin-1-yl-butoxy)-benzyl]-(2-pyrrolidin-1-yl-ethyl)-amine: An 8 mL DMF solution of [4-(4-bromo-butoxy)-benzyl]-(2-pyrrolidin-1-yl-ethyl)-amine (307 mg, 0.86 mmol) and piperidine (0.22 mL, 2.2 mmol) is stirred at 90° C. for six hours under $N_2$. The reaction mixture is cooled, diluted with $CH_2Cl_2$, filtered, washed with brine, dried ($Na_2SO_4$), and concentrated. The residue is purified by chromatography ($SiO_2$; 0-6% MeOH/$CH_2Cl_2$/1% $NH_4OH$ gradient) to give the product (40 mg, 12% yld). MS(ES+) 360.4(M+H)+ free base.

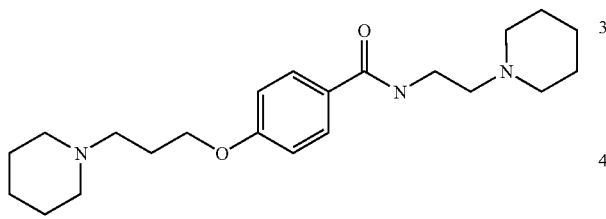

EXAMPLE 236

N-(2-Piperidin-1-yl-ethyl)-4-(3-piperidin-1-yl-propoxy)-benzamide is prepared according to general procedure A from 4-Hydroxy-N-(2-piperidin-1-yl-ethyl)-benzamide (CAS Registry 106018-38-6) (0.27 g, 1.1 mmol) to give the title compound as a white solid (77 mg, 19%). MS (ES+) 374.3

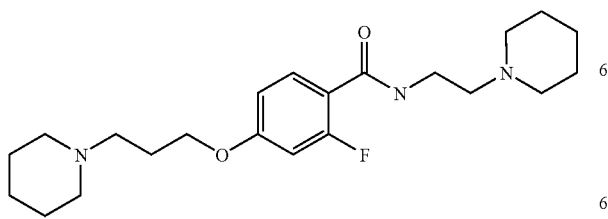

EXAMPLE 237

2-Fluoro-N-(2-piperidin-1-yl-ethyl)-4-(3-piperidin-1-yl-propoxy)-benzamide: To a mixture of 2-Fluoro-4-(3-piperidin-1-yl-propoxy)-benzoic acid (70 mg, 0.25 mmol) and 1-(2-aminoethyl)piperidine (450 □L, 0.3 mmol) in DMF (5 mL) was added EDC (58 mg, 0.3 mmol), HOBT (40 mg, 0.3 mmol), and diisopropylethyl amine (52 □l, 0.3 mmol). The mixture was stirred at room temperature overnight. The mixture was partitioned between EtOAc and water. The organic phase was washed with brine, dried ($MgSO_4$), and concentrated. The residue was purified by flash chromatography (Biotage 12 M, elute 90/10/1 $CH_2Cl_2$/MeOH/$NH_4OH$) to yield the title compound. MS (ES+) 392.3

EXAMPLE 264

3-Fluoro-N-(2-piperidin-1-yl-ethyl)-4-(3-piperidin-1-yl-propoxy)-benzamide is prepared from 3-Fluoro-4-hydroxy-N-(2-piperidin-1-yl-ethyl)-benzamide (0.1 g, 0.38 mmol) by general procedure A to yield the title compound as an off-white solid (80 mg, 54%). MS (ES+) 392.2

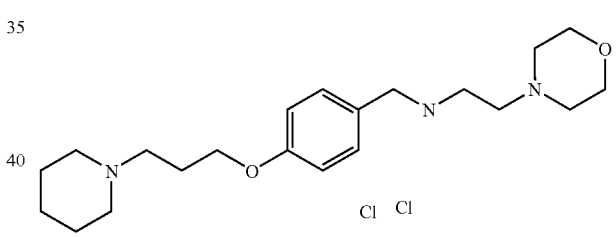

EXAMPLE 256

(2-Morpholin-4-yl-ethyl)-[4-(3-piperidin-1-yl-propoxy)-benzyl]-amine dihydrochloride: The dihydrochloride salt was prepared from (2-morpholin-4-yl-ethyl)-[4-(3-piperidin-1-yl-propoxy)-benzyl]-amine (0.307 g) by dissolving in THF (6 mL) and adding a solution of HCl in $Et_2O$ (1 M, 0.85 mL). Additional $Et_2O$ was added until the mixture was cloudy, and the mixture was allowed to stand at 0° C. overnight. The white solid was collected by filtration to give the dihydrochloride salt. Anal. Calculated for $C_{21}H_{35}N_3O_2$·2 HCl: C, 58.06; H, 8.58; N, 9.67; Cl, 16.32. Found: C, 58.0; H, 8.51; N, 9.57; Cl, 16.99.

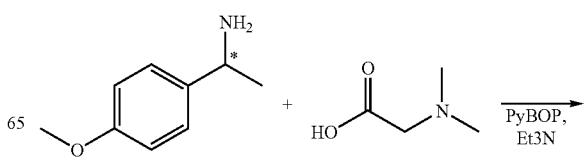

-continued

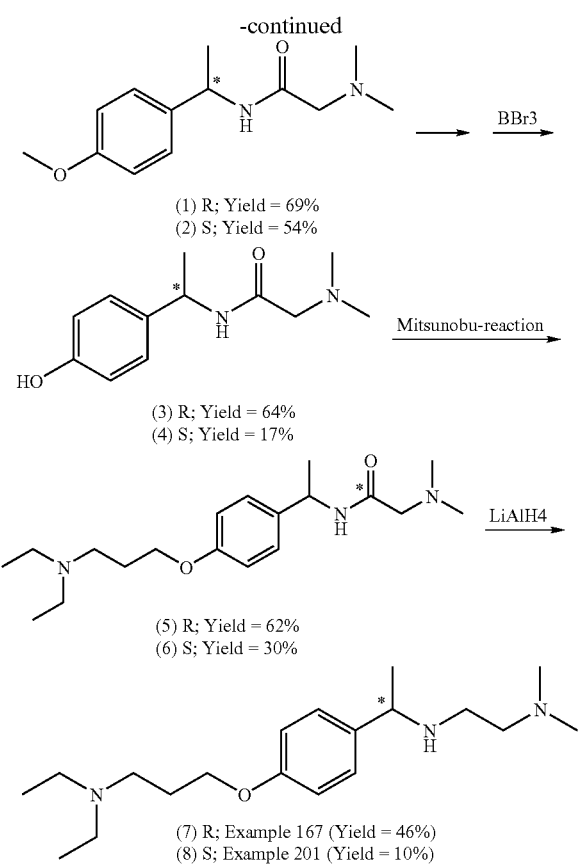

(1) R; Yield = 69%
(2) S; Yield = 54%

(3) R; Yield = 64%
(4) S; Yield = 17%

(5) R; Yield = 62%
(6) S; Yield = 30%

(7) R; Example 167 (Yield = 46%)
(8) S; Example 201 (Yield = 10%)

Synthesis of (1)

1.50 g of ® (+)-1-(4-methoxyphenyl) ethylamine (10.0 mmol), 2.06 g of N,N-Dimethylglycine (20.0 mmol) and 2.58 g of N,N-Di-isopropylethylamine (20.0 mmol) were dissolved in 50 ml of $CH_2Cl_2$ and 6.78 g of PyBOP (13.0 mmol) was added to the mixture. The reaction mixture was stirred at room temperature for 4 h. The reaction mixture was diluted with 20 ml of $CH_2Cl_2$ and washed with brine, 0.1N Hl, brine satNaHCO3 and brine. The separated organic layer was dried over NaSO4 and evaporated. The crude product was applied to short silica-gel column chromatography ($CH_2Cl_2 \rightarrow CH_2Cl_2$: 2M NH3 in MeOH=20:1) and pure product was recrystalized from $Et_2O/CH_2Cl_2$. White powder. 1.62 g (69%). C/MS:m/z 237(M+1)

Synthesis of (2)

This compound was synthesized according to the method described in the preparation of (1).

Synthesis of (3)

500 mg of compound (1) (2.12 mmol) was dissolved in 5.0 ml of $CH_2Cl_2$ and cooled to 0° C. 10.0 ml of BBr3 1.0M in $CH_2Cl_2$ (10 mmol) was added slowly and stirred at 0° C. for 1 h. MeOH was added to quench the reaction and 4.0 ml of 5NaOHaq. was added. The mixture was stirred at 0° C. for 10 min. $CH_2Cl_2$ layer was separated. The water layer was acidified slowly PH=14→2 and extracted with $CH_2Cl_2$ for each step. The water layer was concentrated in vacuo, filtered off NaCl. The filtrate was made to PH=10 stepwise and extracted with $CH_2Cl_2$ each step. All of these extractions were combined together, dried over NaSO4 and evaporated to give the product 301 mg (64%). LC/MS:m/z 223(M+1)

Synthesis of (4)

This compound was synthesized according to the method described in the preparation of (3).

Synthesis of (5)

52 mg of compound (3) (0.23 mmol), 57 mg of 3-diethylaminopropanol (0.28 mmol) and 73 mg of Triphenylphosphine (0.28 mmol) were dissolved in 2.0 ml of dry THF. The air was replaced to $N_2$ gas. 37 mg of Diisopropyl-azodicarboxylate (0.28 mmol) in 0.5 ml of THF was added to this reaction mixture and stirred at room temparature for overnight. The reaction mixture was concentrated and applied to SCX column, washed by MeOH. The crude product was eluted with 2M NH3 in MeOH. This crude product was applied to silica-gel column chromatography ($CH_2Cl_2$: 2M NH3 in MeOH=20:1) to give the product. 48 mg (62%). LC/MS: m/z 336(M+1)

Synthesis of (6)

This compound was synthesized according to the method described in the preparation of (5).

Synthesis of (7)

3.0 ml of Litium aluminium hydride 1.0M in THF (3.0 mmol) was placed in flask and the air was replaced to N2 gas. 43 mg of compound (5) (0.13 mmol) in 2.0 ml of THF was added slowly into the flask and stirred under reflux for 2 h. The reaction mixture was allowed to cool to room temperature and water was added to quench the reaction. The organic layer was decanted. The water layer was extracted with $CH_2Cl_2$ (3 times) and all organic layers were combined together. This solution was dried over NaSO4 and evaporated. The crude product was applied to silica-gel column chromatography ($CH_2Cl_2$: 2M NH3 in MeOH=20: 1) to give the product. 19 mg (46%). LC/MS:m/z 322(M+1)

Synthesis of (8)

This compound was synthesized according to the method described in the preparation of (7).

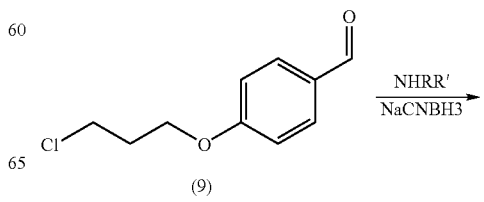

(9)

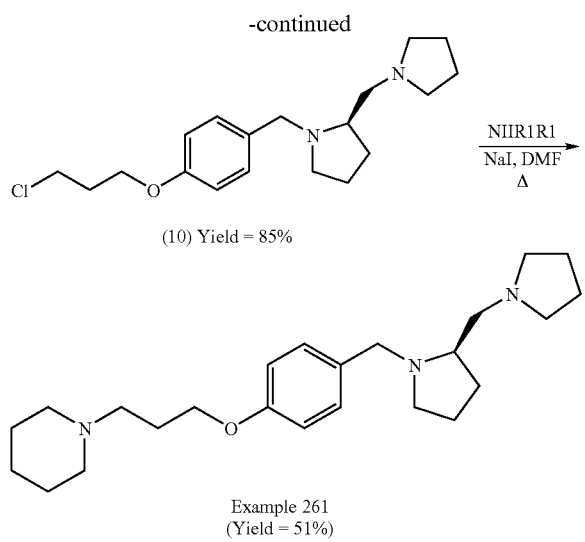

Example 261
(Yield = 51%)

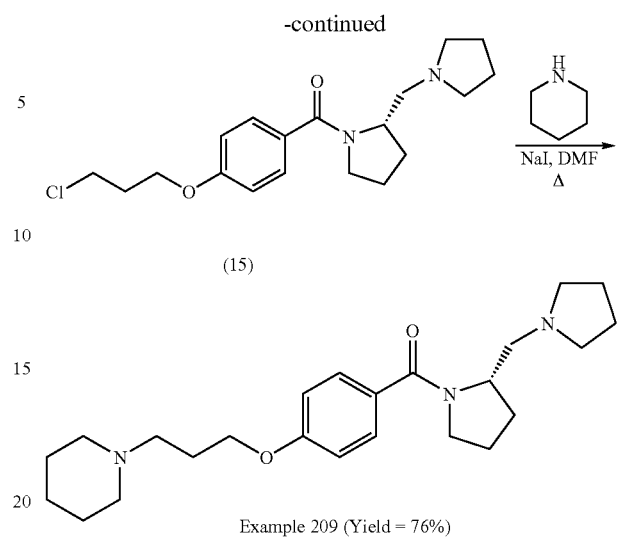

Example 209 (Yield = 76%)

Synthesis of (10) 100 mg of compound (9) (0.50 mmol) and 116 mg of (R)(−)-1-(2-pyrrolidinylmethyl)pyrrolidine (0.75 mmol) were dissolved in 5.0 ml of 5% AcOH in $CH_2Cl_2$ and 310 mg of MP-cyanoborohydride (mmo/g=2.42, 0.75 mmol) was added in the reaction vial. The vial was capped by Teflon cap and shaken at 60° C. for overnight. The reaction mixture was filtered and the filtrate was concentrated under N2 gas. The crude product was applied to silica-gel column chromatography ($CH_2Cl_2$: 2M NH3 in MeOH=20:1) to give the product. 143 mg (85%). LC/MS: m/z 337(M+1)

Synthesis of Example 261

65 mg of compound (10) (0.19 mmol) and 50 mg of piperidine (0.58 mmol) were put into 4.0 ml vial and 2.0 ml of THF and 10 mg of NaI were added to the vial. The vial was capped by Teflon cap and heated at 100° C. for 3 days. The reaction mixture was concentrated under N2 gas and applied to silica-gel column chromatography ($CH_2Cl_2$: 2M NH3 in MeOH=20:1) to give the product. 38 mg (51%). LC/MS: m/z 386(M+1)

Synthesis of (15)

813 mg of compound (14) (98536) (3.8 mmol) was dissolved in 5.0 ml of thionyl chloride and stirred at 70° C. for 1 h under N2 gas. The excess acid chloride was removed in vacuo. The residue was dissolved in 1.0 ml of $CH_2Cl_2$ to make acid chloride solution. 643 mg of (S)(+)-1(2-pyrrolidinylmethyl)pyrrolidine (4.17 mmol) and 421 mg of triethylamine (4.17 mmol) were dissolved in 10 ml of $CH_2Cl_2$ and cooled to 0° C. Acid chloride solution was added to this mixture at 0° C. and stirred at room temperature for 2 h. The reaction mixture was diluted with $CH_2Cl_2$ and washed by brine. The crude product was applied to silica-gel column chromatography ($CH_2Cl_2$: 2M NH3 in MeOH=10:1) to give the product. 1.13 g (85%) LC/MS: m/z 351(M+1)

Synthesis of Example 209

This compound was synthesized according to the method described in the preparation of Example 261.

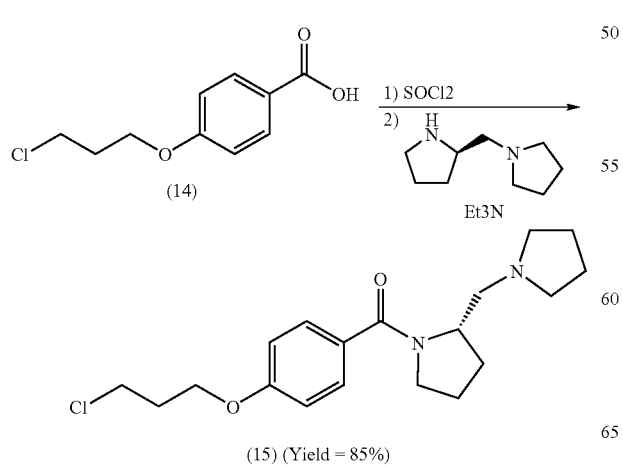

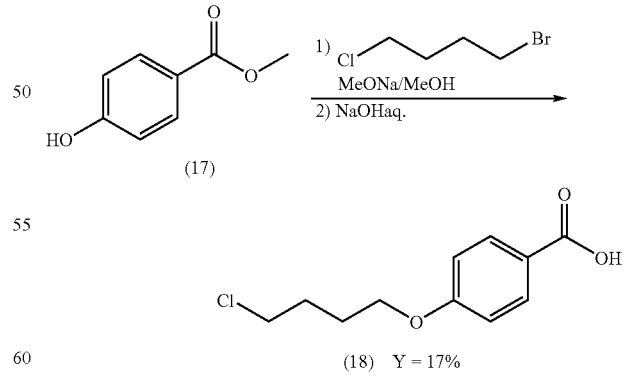

(18)  Y = 17%

Synthesis of (18)

1.17 g of Na (51 mmol) was dissolved in 200 ml of MeOH and 6.48 g of methyl p-hydroxy benzoate (17) (42.5 mmol)

was added followed by 20.52 g of 1-bromo 4-chlorobutane (119.6 mmol). The reaction mixture was stirred at room temperature for 2 h and stirred at 60° C. for 1 h. Almost of MeOH was removed in vacuo. The residue was dissolved in water and acidified by cHCl to PH=1.0 and extracted with CH$_2$Cl$_2$. The separated organic layer was dried over NaSO4 and evaporated. The crude product was applied to silica-gel column chromatography (CH$_2$Cl$_2$: 2M NH3 in MeOH=20:1) to give the product. 1.64 g (17%). NMR (DMSO); 7.84(d, 2H, J=5.9 Hz), 6.91(d, 2H, J=5.9 Hz), 4.02(t, 2H, J=5.8 Hz), 3.69(t, 2H, J=6.4 Hz), 1.85(m, 4H)

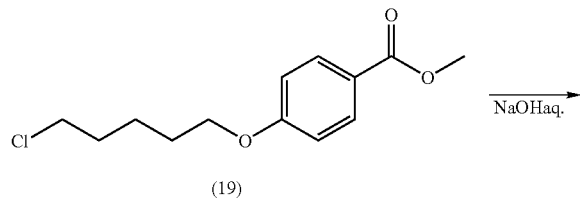

(19)

(20) Yield = 77%

Synthesis of (20)

1.14 g of compound (19) (4.44 mmol) was dissolved in 15 ml of MeOH and 10 ml of 5N NaOHaq. was added. The reaction mixture was stirred at room temperature for overnight. The reaction mixture was evaporated. The residue was dissolved in water and acidified by cHCl to PH=1.0. This solution was extracted with CH$_2$Cl$_2$, dried over NaSO4 and evaporated. The pure product was recrystalized from Hexane/CH$_2$Cl$_2$. 829 mg (77%) NMR (DMSO); 8.05(d, 2H, J=8.9 Hz), 6.93(d, 2H, J=8.9 Hz), 4.05(t, 2H, J=6.3 Hz), 3.57(t, 2H, J=6.8 Hz), 1.86(m, 4H), 1.65(m, 2H)

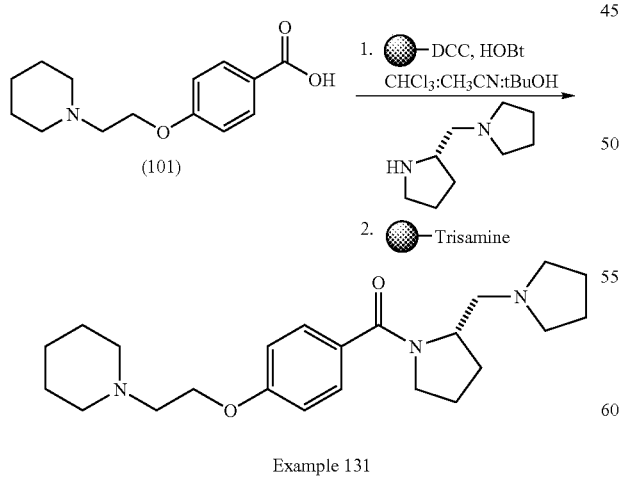

Example 131

To a 4 mL vial was placed 101 (28,5 mg, 0.1 mmol), resin-bound DCC (170 mg, 0.1 mmol), resin-bound DCC (170 mg, 0.16 mmol, 0.94 mmol/g), HOBt (16 mg, 0.12 mmol), amine (13 uL, 0.08 mmol) and a 5:1:1 mixture of CHCl$_3$:CH$_3$CN:tBuOH. The vial was agitated by means of a lab quake shaker overnight. In the morning, PS-trisamine (134 mg, 0.4 mmol, 3.0 mmol/g) was added and the reaction again allowed to rotate overnight to scavenge excess carboxylic acid and HOBt. Filtration, washing with DCM/MeOH and concentration afforded a orange foam. Filtration through a short pipet column provided 25 mg (83%) of an yellow solid, 629304. Mass spec hit M+1, 386; LCMS>95% @230 nm and ELSD. A substantially analogous procedure was employed for the array synthesis of Examples:

| Example # | Observed Mass |
|---|---|
| 41 | 361 |
| 42 | 361 |
| 44 | 389 |
| 43 | 401 |
| 130 | 386 |
| 131 | 386 |
| 132 | 401 |
| 133 | 372 |
| 144 | 400 |
| 150 | 360 |
| 151 | 340 |
| 152 | 346 |
| 153 | 360 |
| 154 | 360 |
| 155 | 386 |
| 173 | 358 |

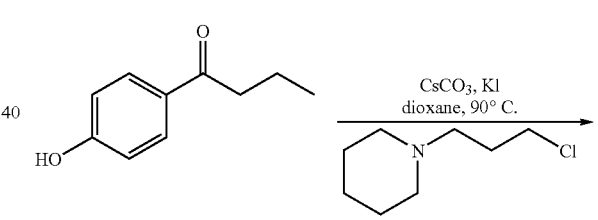

(201)

1-[4-(3-Piperidin-1-yl-propoxy)-phenyl]-butan-1-one

To a 20 mL vial was placed keto-phenol (500 mg, 3 mmol), CsCO$_3$ (1.98 g, 6 mmol), KI (454 mg, 3 mmol) and chloropropylpiperdine (64 mg, 3.3 mmol). Dioxane added and the reaction was heated to 90 degrees overnight on a J-KEM heater/shaker block. The reaction was then quenched with water, extracted into DCM and dried over Na2SO4. The material was purified by Biotage utilizing 4:1 EtOAc:MeOH to afford (201) as a orange oil (880 mg, 99%). Mass spec hit M+1, 290; LCMS>95% @230 nm and ELSD.

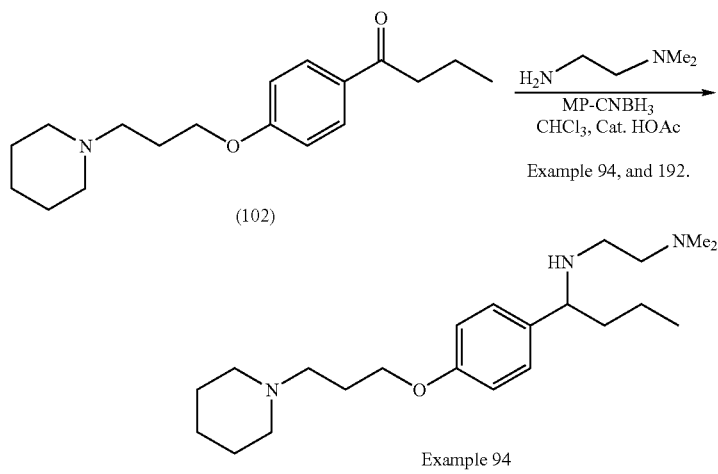

Example 94, and 192.

Example 94

To a 20 mL vial was placed (102) (300 mg, 1 mmol), diamine (120 mg, 1.14 mmol), MP-CNBH$_3$ (2.4 g, 6.22 mmol) and a 9:1 CHCl$_3$:HOAc solution. The reaction was heated to 50 degrees overnight on a J-KEM heater/shaker block. The reaction was filtered, washed with DCM/MeOH. The material was then subjected to preparative HPLC purification to afford 29 mg (3%) of analytically pure example 94. as a white solid. Mass spec hit M+1, 362; LCMS>98% @230 nm and ELSD. Example 192 can be made by a substantially analogous procedure, Observed mass 360. The following examples are made by a substantially analogous procedure:

| Phenyl Ketone | Product Name | Example | (M + 1) |
|---|---|---|---|
|  | N-[6-(3-Dimethylamino-propoxy)-1,2,3,4-tetrahydro-naphthalen-1-yl]-N',N'-dimethyl-ethane-1,2-diamine | 84 | 320 |
|  | N-[6-(3-Dimethylamino-2-methyl-propoxy)-1,2,3,4-tetrahydro-naphthalen-1-yl]-N',N'-dimethyl-ethane-1,2-diamine | 85 | 246 M − 87 |
|  | N,N-Dimethyl-N'-[6-(1-methyl-piperidin-3-ylmethoxy)-1,2,3,4-tetrahydro-naphthalen-1-yl]-ethane-1,2-diamine | 86 | 346 |
|  | N-{1-[4-(3-Dimethylamino-2-methyl-propoxy)-phenyl]-propyl}-N',N'-dimethyl-ethane-1,2-diamine | 87 | 322 |

-continued

| Phenyl Ketone | Product Name | Example | (M + 1) |
|---|---|---|---|
| 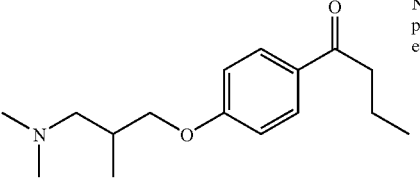 | N-{1-[4-(3-Dimethylamino-2-methyl-propoxy)-phenyl]-butyl}-N',N'-dimethyl-ethane-1,2-diamine | 88 | 336 |
| 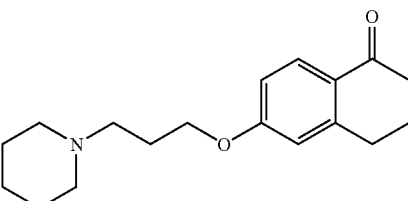 | N,N-Dimethyl-N'-[6-(3-piperidin-1-yl-propoxy)-1,2,3,4-tetrahydro-naphthalen-1-yl]-ethane-1,2-diamine | 89 | 272 M − 87 |
| 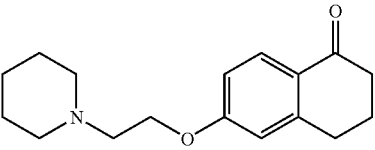 | N,N-Dimethyl-N'-[6-(2-piperidin-1-yl-ethoxy)-1,2,3,4-tetrahydro-naphthalen-1-yl]-ethane-1,2-diamine | 90 | 258 M − 87 |
| 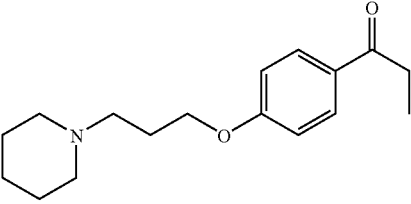 | N,N-Dimethyl-N'-{1-[4-(3-piperidin-1-yl-propoxy)-phenyl]-propyl}-ethane-1,2-diamine | 91 | 348 |
| 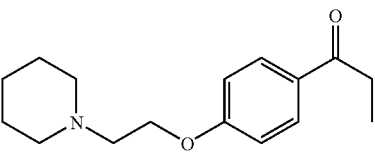 | N,N-Dimethyl-N'-{1-[4-(2-piperidin-1-yl-ethoxy)-phenyl]-butyl}-ethane-1,2-diamine | 92 | 334 |
| 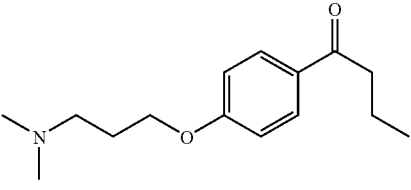 | N-{1-[4-(3-Dimethylamino-propoxy)-phenyl]-butyl}-N',N'-dimethyl-ethane-1,2-diamine | 93 | 322 |
| 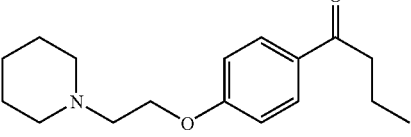 | N,N-Dimethyl-N'-{1-[4-(2-piperidin-1-yl-ethoxy)-phenyl]-butyl}-ethane-1,2-diamine | 95 | 348 |

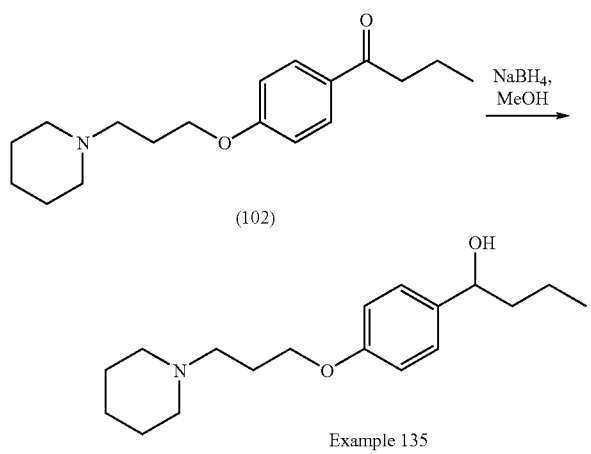

Example 135

EXAMPLES 135, 14, 126 6

To a 10 mL round-bottom flask was added (102) (280 mg, 0.96 mmol) and dry MeOH (5 mL). Then, NaBH$_4$ (74 mg, 1.93 mmol) was added at room temperature. After 1 hour, the reaction was then quenched with water, extracted into DCM and dried over Na$_2$SO$_4$. The material was purified by Biotage utilizing 4:1 EtOAc:MeOH to provide 270 mg (98%) of a white solid. Mass spec hit M+1,292; LCMS>98% @230 nm and ELSD. Examples 14 and 126 are made by a substantially analogous procedure. Observed mass: Example 14=321, Example 126=375.

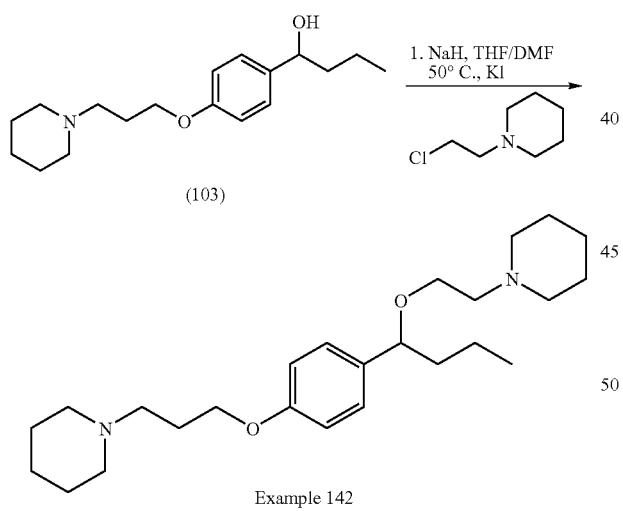

Example 142

EXAMPLE 142

To a round-bottom flask, equipped with stir bar and septum, was placed (103) (300 mg, 1.03 mmol), KI (230 mg, 1.54 mmol) and NaH (78 mg, 95% dry, 3.09 mmol). Then, dry DMF (20 mL, 0.5 M) was added via syringe followed by chloroethylpiperidine (285 mg, 1.54 mmol). The reaction was allowed to stir at 50 degrees overnight. In the morning, the reaction was quenched with water, extracted into EtOAc (3×20 mL) and dried over brine. Column chromatography in 9:1 DCM:MeOH afforded 631934 an yellow oil (300 mg, 79%). Mass sec hit M+1, 404; LCMS>95% @230 nm and ELSD.

EXAMPLE 246

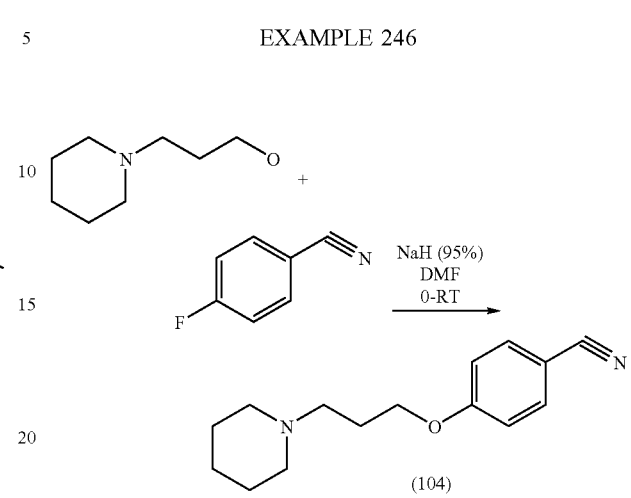

3-Piperidinylpropanol (3.56 g, 25 mmoles) in 4 ml DMF was added to a slurry of sodium hydride in 10 ml DMF at 0 C., and the reaction was stirred at 0 C. for 0.5 hr. The 4-fluorobenzonitrile in 6 ml was added at 0 C. The reaction was stirred at 0 C for 1 hr. and at RT overnight. Water and ether were carefully added. Separated the ether layer and extracted with water five times. The ether extract was dried over sodium sulfate, filtered and evaporated to give 6.0 g (0.0246 mmoles, 98.4% yield). LCMS 1.61 min @254.0 nm 95.2%; @230.0 nm 89.5%; ELSD 1.71 min 100%; MS 1.59 min M+1=245 good for product (104).

Example 246

EXAMPLE 246

The nitrile (6.0 g, 0.0246 mmoles) in 250 ml 2B EtOH with 2.5 g RaNi was hydrogenated at 80 C. for 8 hrs. Filtration and evaporation yielded 5.4 g oil (88.4 yield).

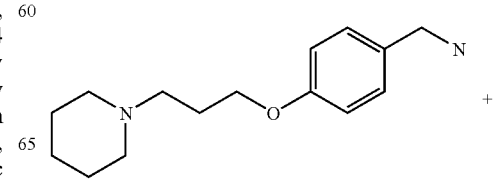

-continued

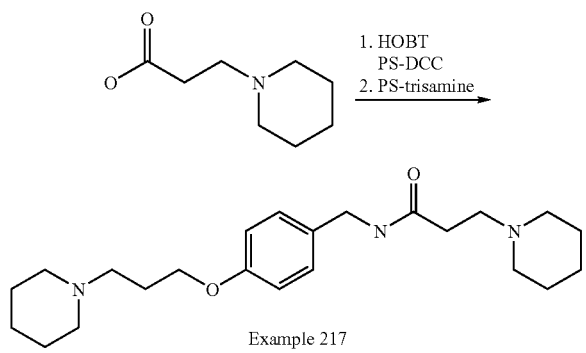

Example 217

EXAMPLE 217

The 1-hydroxybenzotriazole hydrate (13.5 mg, 0.1 mmole), 1-piperidinepropionic acid (18.1 mg, 0.115 mmole), amine (248 mg, 0.1 mmole), polystyrene-carbodiimide (125 mg, 0.15 mmoles) and 2.5 ml chloroform, acetonitrile, t-butanol (5:1:1) in a 4 ml vial were rotated for four days. Polysterene-trisamine (93.7 mg, 0.4 mmoles) was added and the reaction was rotated overnight. Filtered reaction through filter cartridge and evaporated to give 37.5 mg, 0.0967 mmole, 96.7% yield. LCMS ELSD 1.42 min 100%, MS 1.21 min M+1=388 good for product.

| Example | Observed Mass |
|---|---|
| 116 | 348 |
| 117 | 376 |
| 118 | 350 |
| 119 | 384 |
| 120 | 391 |
| 121 | 322 |
| 122 | 398 |
| 123 | 393 |
| 124 | 388 |
| 125 | 477 |

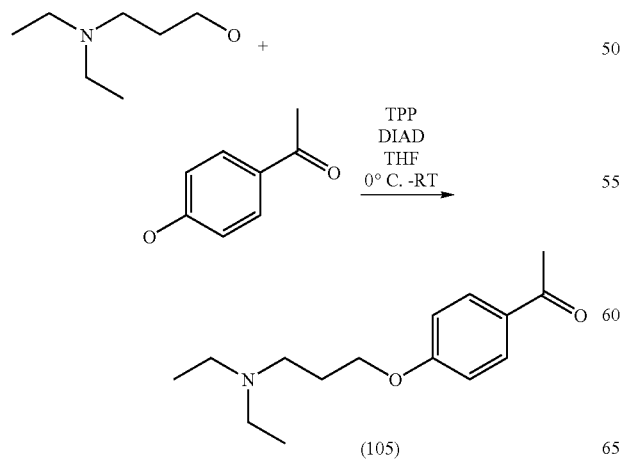

EXAMPLE 15

The solution of diisopropylazodicarboxylate (3.93 ml, 20 mmoles) in 20 ml anhydrous THF was added dropwise with stirring to the cold solution of 4-hydroxyacetophenone (2.18 g, 16 mmoles), 3-diethylaminopropanol (2.23 ml, 15 mmoles) and triphenylphosphine (4.98 g, 19 mmoles) in 50 ml anhydrous THF over 45 minutes. The reaction was stirred in an ice bath for one hour and at room temperature for 18 hours. The solvent was evaporated and ether was added. This solution was extracted with dilute HCl (1.0 N) four times. These combined acidic extracts were extracted with ether, basified with a NaOH solution and extracted with ether three times. These combined ethereal extracts were dried over sodium sulfate, filtered and evaporated to give 3.41 g oil. LCMS 1.53 min @254.0 nm 97.4%; ELSD 1.59 min 91.1%; MS 1.58 min M+1=250 good for product (105).

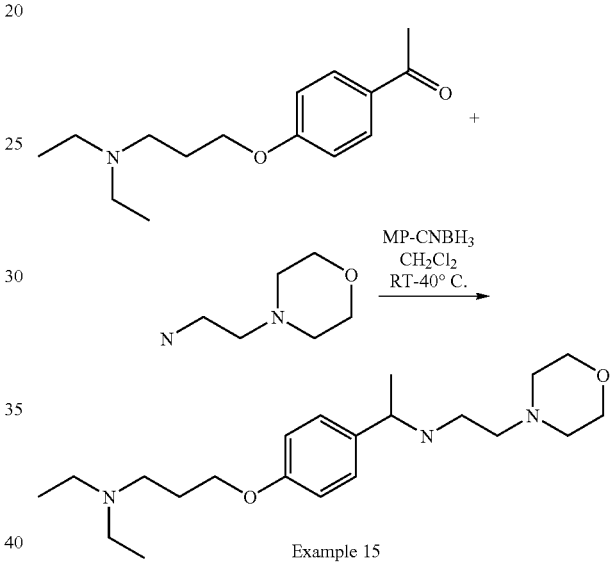

Example 15

In a 7 ml vial with cap, 4-(3-diethylaminopropyloxy)acetophenone (0.47 g, 0.19 mmoles), N-(2-aminoethyl)morpholine (0.039 ml, 0.3 mmoles) and macroporus cyanoborohydride (169 mg, 0.4 mmoles) in 2 ml dichloromethane with 0.2 ml glacial acetic were heated on shaker at 55° for 18 hours. Purified with a 3 ml extrelut cartridge hydrated with 3 ml water. The reaction solution was added and the cartridge was rinsed with dichloromethane (5 ml). The product was eluted with 10% triethylamine/dichloromethane. LCMS 1.14 min @254.0 nm 95.6%; @230.0 nm 95.3%; 1.20 min ELSD 95.3%; MS 1.14 min M+1=364 good for product.

| Example | Observed Mass |
|---|---|
| 15 | 364 |
| 16 | 348 |
| 17 | 308 |
| 18 | 362 |
| 19 | 336 |
| 20 | 377 |
| 21 | 391 |
| 1 | 336 |
| 22 | 381 |
| 231 | 363 |

| Example | Observed Mass |
|---------|---------------|
| 24 | 362 |
| 25 | 359 |
| 26 | 336 |
| 27 | 376 |

EXAMPLE 62

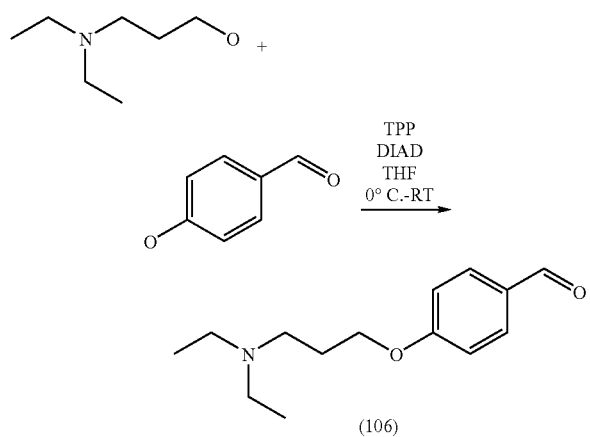

(106)

The solution of diisopropylazodicarboxylate (3.93 ml, 20 mmoles) in 20 ml anhydrous THF was added dropwise with stirring to the cold solution of 4-hydroxybenzaldehyde (1.95 g, 16 mmoles), 3-diethylaminopropanol (2.23 ml, 15 mmoles) and triphenylphosphine (4.98 g, 19 mmoles) in 50 ml anhydrous THF over 45 minutes. The reaction was stirred in an ice bath for one hour and at room temperature for 18 hours. The solvent was evaporated and ether was added. This solution was extracted with dilute HCl (1.0 N) four times. These combined acidic extracts were extracted with ether, basified with a NaOH solution and extracted with ether three times. These combined ethereal extracts were dried over sodium sulfate, filtered and evaporated to give 3.71 g oil. LCMS 1.47 min @254.0 nm 97.0%; ELSD 1.53 min 95.4%; MS 1.48 min M+1=236 good for product.

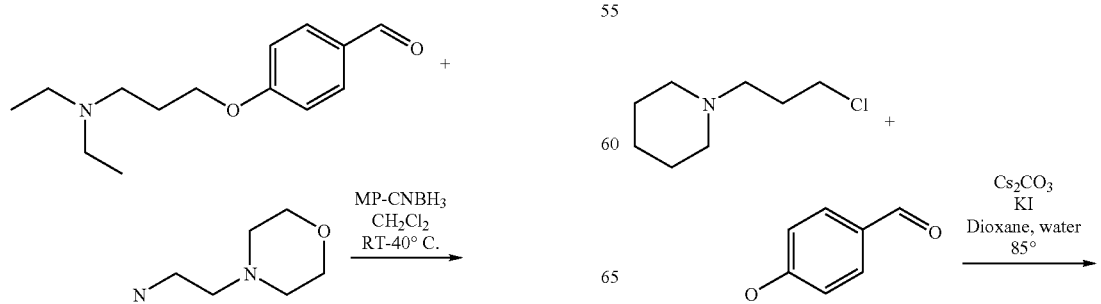

Example 62

In a 7 ml vial with cap, 4-(3-diethylaminopropyloxy)benzaldehyde (0.59 g, 0.25 mmoles), N-(2-aminoethyl)morpholine (0.049 ml, 0.375 mmoles) and macroporus cyanoborohydride (210 mg, 0.5 mmoles) in 3 ml dichloromethane with 0.3 ml glacial acetic were heated on shaker at 40° briefly. Purified with 3 ml extrelut cartridge hydrated with 3 ml water. The reaction was added and the cartridge was rinsed with dicloromethane (5 ml). The product was eluted with 10% triethylamine/dichloromethane. LCMS 1.14 min ELSD 95.3%; MS 1.09 min M+1=350 good for product Example 62.

| Example | Observed Mass |
|---------|---------------|
| 629 | 350 |
| 63 | 334 |
| 47 | 294 |
| 48 | 348 |
| 49 | 348 |
| 50 | 322 |
| 51 | 363 |
| 52 | 377 |
| 61 | 322 |
| 53 | 349 |
| 54 | 348 |
| 70 | 345 |
| 71 | 322 |
| 72 | 362 |
| 73 | 364 |
| 59 | 376 |
| 74 | 348 |
| 104 | 320 |
| 113 | 420 |
| 114 | 410 |
| 107 | 334 |
| 103 | 334 |

EXAMPLE 45

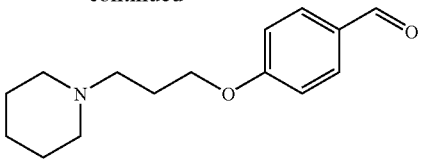

(107)

4-Hydroxybenzaldehyde (2.44 g, 20 mmoles), N-(3-Chloropropyl)piperidine hydrochloride, cesium carbonate (19.7 g, 60 mmoles) and potassium iodide in 14 ml dioxane with 0.7 ml water were stirred at 85° for 8 hours and at room temperature for 16 hours. Evaporated the decanted supernatant, added water to both (evaporated supernatant and solid) and extracted three times with ether. These combined ethereal extracts were washed three times with water, dried over sodium sulfate, filtered and evaporated to give 7.8 g oil. LCMS 1.48 min @254.0 nm 99.4%; @230.0 nm 89.6%; 1.51 min ELSD 99.4%; MS 1.49 min M+1=248 good for product. 300 mHz NMR(CDCl$_3$) good for structure (107).

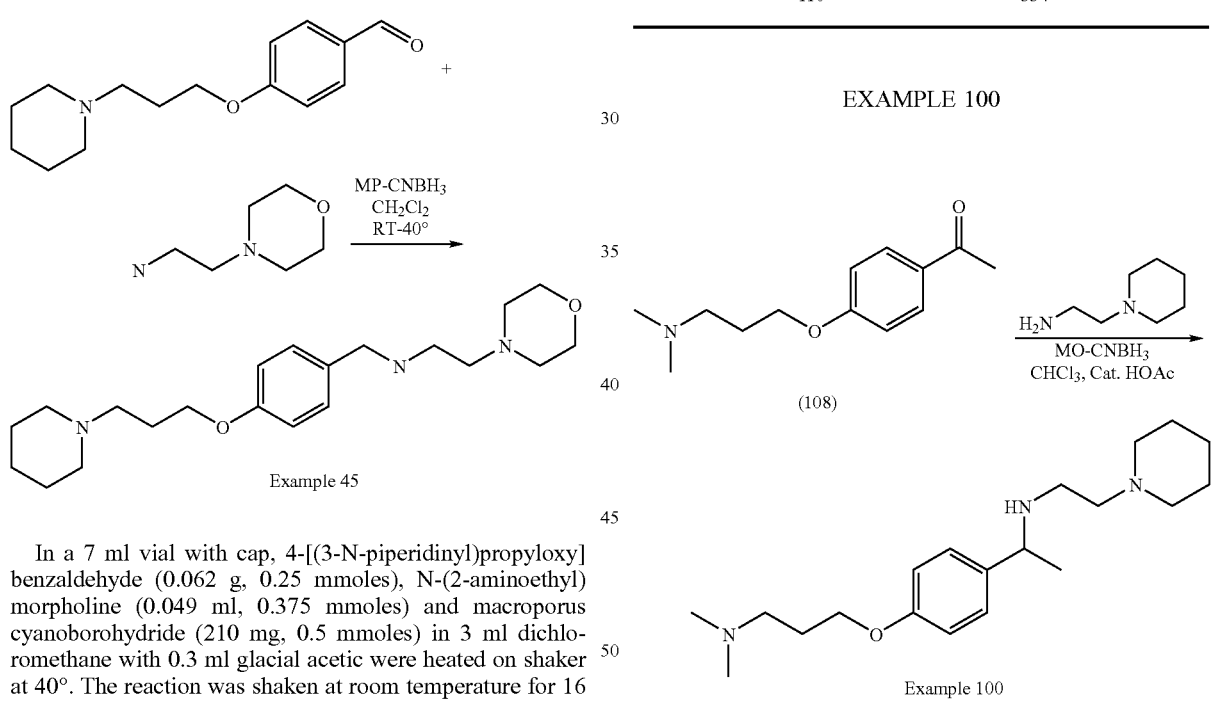

Example 45

In a 7 ml vial with cap, 4-[(3-N-piperidinyl)propyloxy]benzaldehyde (0.062 g, 0.25 mmoles), N-(2-aminoethyl)morpholine (0.049 ml, 0.375 mmoles) and macroporus cyanoborohydride (210 mg, 0.5 mmoles) in 3 ml dichloromethane with 0.3 ml glacial acetic were heated on shaker at 40°. The reaction was shaken at room temperature for 16 hours and at 40° for one hour. Purified with 3 ml extrelut cartridge hydrated with 3 ml water. The reaction solution was added and the cartridge was rinsed with dicloromethane (5 ml). The product was eluted with 10% triethylamine/dichloromethane. LCMS 1.13 min @230.0 nm 97.3%; 1.19 min ELSD 98.5%; MS 1.13 min M+1=362 good for product Example 45.

| Example | Observed Mass |
|---------|---------------|
| 45 | 362 |
| 46 | 346 |
| 64 | 306 |
| 65 | 360 |

| Example | Observed Mass |
|---------|---------------|
| 66 | 360 |
| 67 | 334 |
| 68 | 361 |
| 69 | 360 |
| 55 | 357 |
| 56 | 334 |
| 57 | 374 |
| 58 | 376 |
| 75 | 388 |
| 60 | 360 |
| 102 | 346 |
| 105 | 332 |
| 112 | 432 |
| 115 | 410 |
| 106 | 346 |
| 108 | 375 |
| 109 | 389 |
| 110 | 334 |

EXAMPLE 100

(108)

Example 100

Dimethyl-(3-{4-[1-(2-piperidin-1-yl-ethylamino)-ethyl]-phenoxy}-propyl)-amine To a 20 mL vial was placed (108) (42 mg, 0.19 mmol), amine (37 mg, 0.29 mmol), MP-CNBH$_3$ (190 mg, 0.45 mmol, 2.37 mmol/g) and a 9:1 CHCl$_3$:HOAc solution. The reaction was heated to 50 degrees overnight on a J-KEM heater/shaker block. The reaction was filtered, washed with DCM/MeOH. The material was then subjected to preparative HPLC purification to afford 5.8 mg (9%) example 100. As a clear oil. Mass spec hit M+1, 334; LCMS>89% @214 nm.

In a procedure substantially similar to that for synthesis if Example 100, the following examples are made:

| Amino Ketone | Amine | Product Name | Example | MS |
|---|---|---|---|---|
| | | Dimethyl-[3-(4-{1-[3-(2-methyl-piperidin-1-yl)-propylamino]-ethyl}-phenoxy)-propyl]-amine | 13 613123 | 362 |
| | | N-{1-[4-(3-Dimethylamino-propoxy)-phenyl]-ethyl}-N'-ethyl-N'-m-tolyl-ethane-1,2-diamine | 12 613021 | 384 |
| | | (1-{1-[4-(3-Dimethylamino-propoxy)-phenyl]-ethyl}-pyrrolidin-3-yl)-dimethyl-amine | 11 613011 | 320 |
| | | Dimethyl-(3-{4-[1-(1-phenyl-ethyl amino)-ethyl]-phenoxy}-propyl)-amine | 10 | 327 |
| | | Dimethyl-(3-{4-[1-(2-morpholin-4-yl-ethylamino)-ethyl]-phenoxy}-propyl)-amine | 96 623901 | 335 |
| | | $N^4$-{1-[4-(3-Dimethylamino-propoxy)phenyl]-ethyl}-$N^1$,$N^1$-diethyl-pentane-1,4-diamine | 97 | 363 |
| | | [3-(4-{1-[(1-Ethyl-pyrrolidin-2-yl methyl)-amino]-ethyl}-phenoxy)-propyl]-dimethyl-amine | 98 623903 | 333 |

-continued
| Amino Ketone | Amine | Product Name | Example | MS |
|---|---|---|---|---|
| 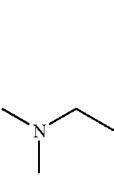 | 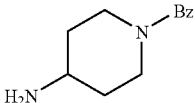 | (1-Benzyl-piperidin-4-yl)-{1-[4-(3-dimethylamino-propoxy)-phenyl]-ethyl}-amine | 99 | 395 |
| 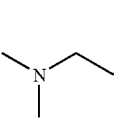 | 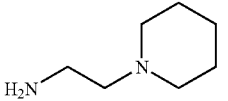 | Dimethyl-(3-{4-[1-(2-piperidin-1-yl-ethylamino)-ethyl]-phenoxy}-propyl)-amine | 100 | 333 |
| 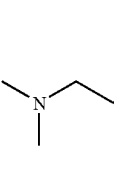 | 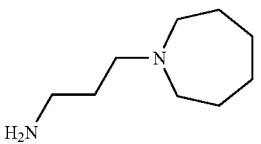 | (3-{4-[1-(3-Azepan-1-yl-propyl amino)-ethyl]-phenoxy}-propyl)-dimethyl-amine | 101 | 361 |
| 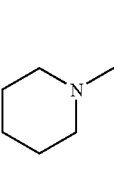 | 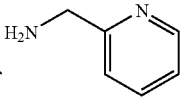 | {1-[4-(3-Piperidin-1-yl-propoxy)-phenyl]-ethyl}-pyridin-2-ylmethyl-amine | 36 | 354 |

-continued

| Amino Ketone | Amine | Product Name | Example | MS |
|---|---|---|---|---|
| (piperidine-propoxy-phenyl ketone structure) | H₂N-CH₂-(pyridin-4-yl) | {1-[4-(3-Piperidin-1-yl-propoxy)-phenyl]-thyl}-pyridin-4-ylmethyl-amine | 37 | 354 |
| (piperidine-propoxy-phenyl ketone structure) | H₂N-CH₂-(tetrahydrofuran-2-yl) | {1-[4-(3-Piperidin-1-yl-propoxy)-phenyl]-ethyl}-(tetrahydro-furan-2-ylmethyl)-amine | 40 | 347 |

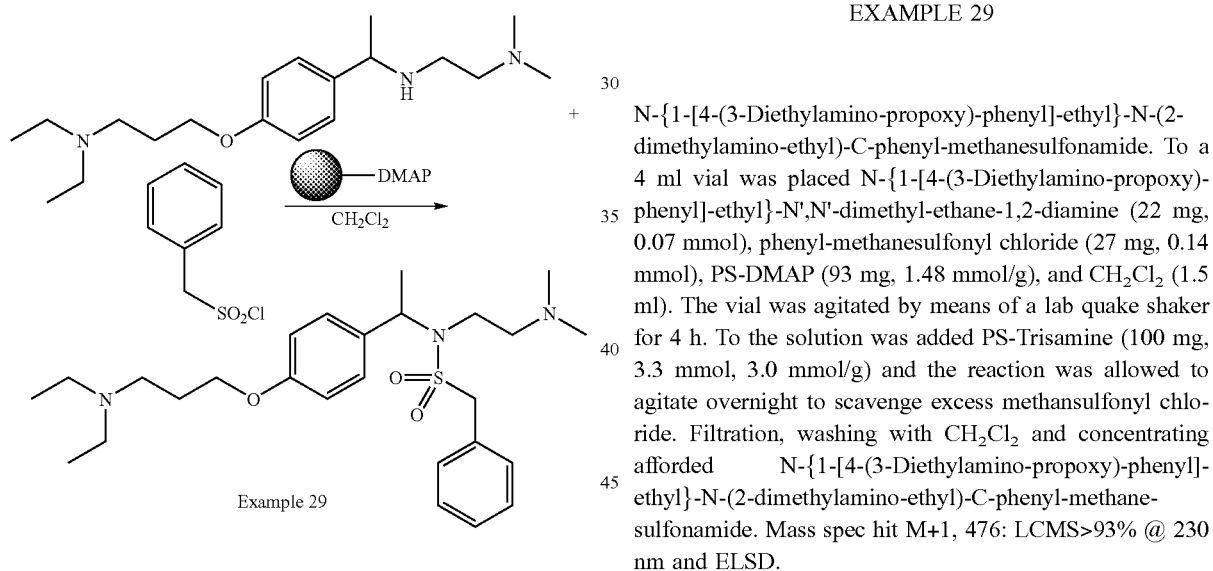

Example 29

EXAMPLE 29

N-{1-[4-(3-Diethylamino-propoxy)-phenyl]-ethyl}-N-(2-dimethylamino-ethyl)-C-phenyl-methanesulfonamide. To a 4 ml vial was placed N-{1-[4-(3-Diethylamino-propoxy)-phenyl]-ethyl}-N',N'-dimethyl-ethane-1,2-diamine (22 mg, 0.07 mmol), phenyl-methanesulfonyl chloride (27 mg, 0.14 mmol), PS-DMAP (93 mg, 1.48 mmol/g), and CH₂Cl₂ (1.5 ml). The vial was agitated by means of a lab quake shaker for 4 h. To the solution was added PS-Trisamine (100 mg, 3.3 mmol, 3.0 mmol/g) and the reaction was allowed to agitate overnight to scavenge excess methansulfonyl chloride. Filtration, washing with CH₂Cl₂ and concentrating afforded N-{1-[4-(3-Diethylamino-propoxy)-phenyl]-ethyl}-N-(2-dimethylamino-ethyl)-C-phenyl-methane-sulfonamide. Mass spec hit M+1, 476: LCMS>93% @ 230 nm and ELSD.

| Sulfonyl Chloride | Product Name | Example | MS (M + 1) |
|---|---|---|---|
| phenyl-SO₂Cl | N-{1-[4-(3-Diethylamino-propoxy)-phenyl]-ethyl}-N-(2-dimethylamino-ethyl)-benzenesulfonamide | 30 | 462 |
| thiophene-SO₂Cl | Thiophene-2-sulfonic acid {1-[4-(3-diethylamino-propoxy)-phenyl]-ethyl}-(2-dimethylamino-ethyl)-amide | 33 | 468 |

-continued

| Sulfonyl Chloride | Product Name | Example | MS (M + 1) |
|---|---|---|---|
| 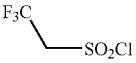 | 2,2,2-Trifluoro-ethanesulfonic acid {1-[4-(3-diethylamino-propoxy)-phenyl]-ethyl}-(2-dimethylamino-ethyl)-amide | 31 | 468 |

Utilizing the procedures provided herein, in addition to methods known in the art, compounds of Formula I and Formula II were prepared. Structural figures for representative examples of Formula I and Formula II are shown the following pages.

| Example Number | Structure | Observed Mass |
|---|---|---|
| 1 | 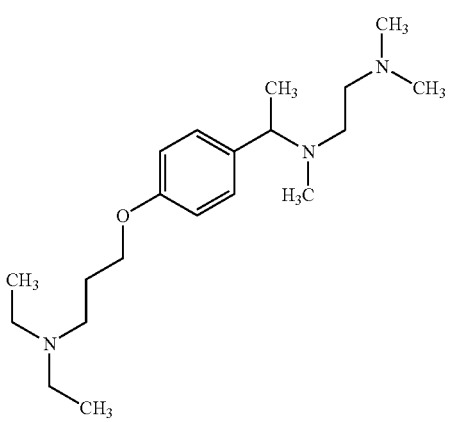 | 336 |
| 2 | 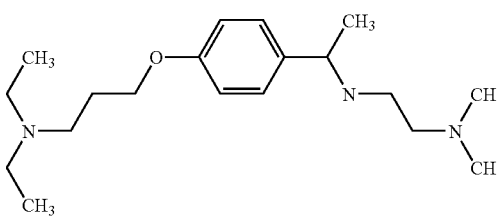 | 321.2 |
| 3 | 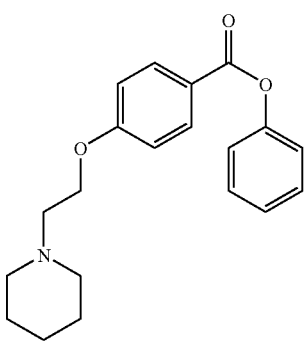 | |

-continued
| Example Number | Structure | Observed Mass |
|---|---|---|
| 4 | 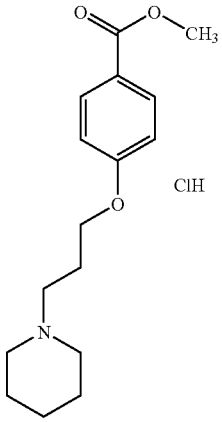 | |
| 5 | 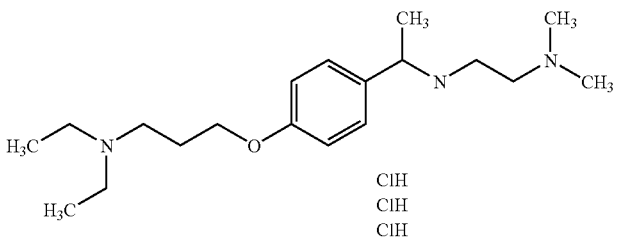 | 321.2 |
| 6 | 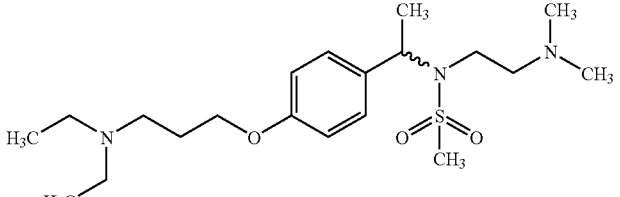 | 400.2 |
| 7 | 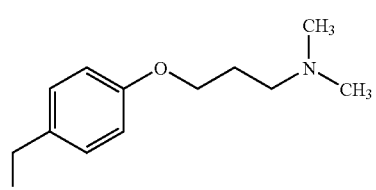 | 210.3 |
| 8 | 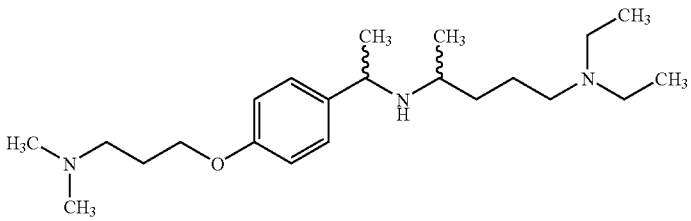 | |
| 9 | 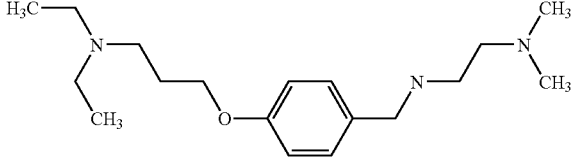 | 308 |

-continued
| Example Number | Structure | Observed Mass |
|---|---|---|
| 10 | 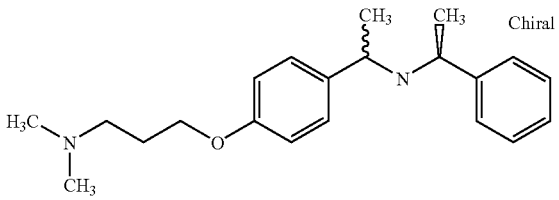 | 327 |
| 11 | 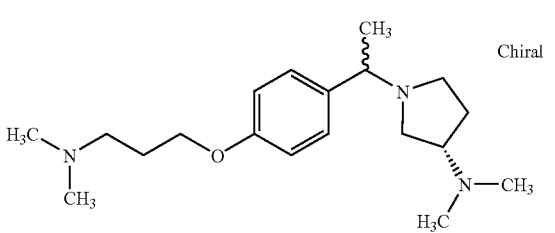 | 320 |
| 12 | 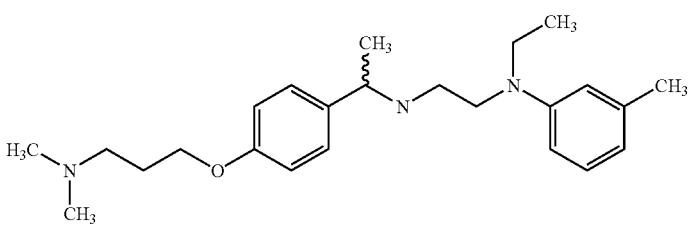 | 384 |
| 13 | 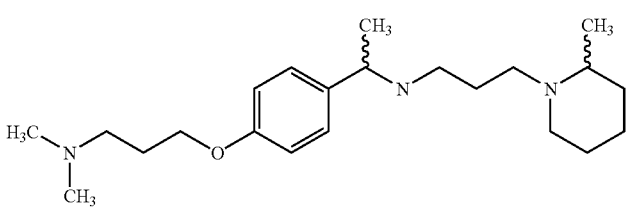 | 362 |
| 14 | 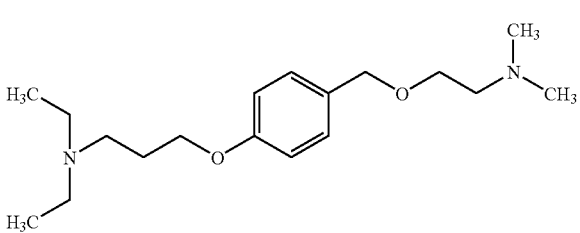 | 321 |
| 15 | 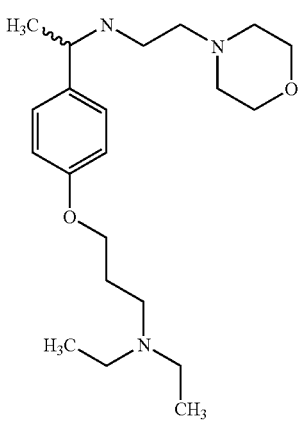 | 363 |

-continued

| Example Number | Structure | Observed Mass |
|---|---|---|
| 16 | 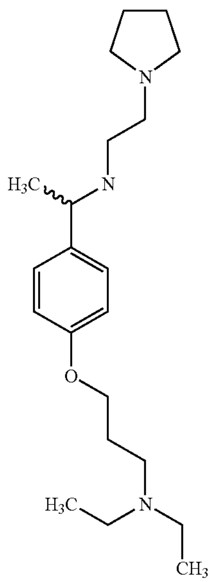 | 348 |
| 17 | 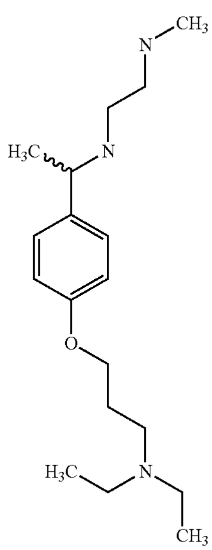 | 308 |
| 18 | 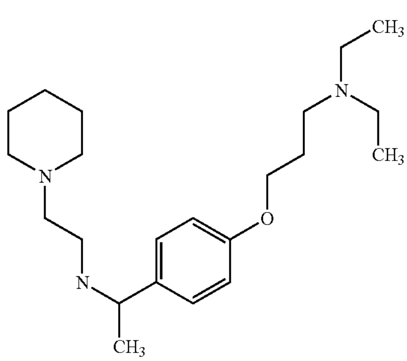 | 362 |

-continued
| Example Number | Structure | Observed Mass |
|---|---|---|
| 19 | 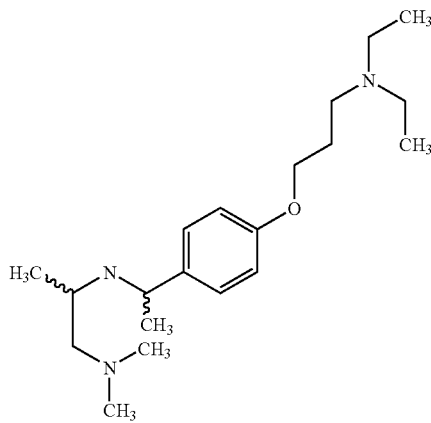 | 336 |
| 20 | 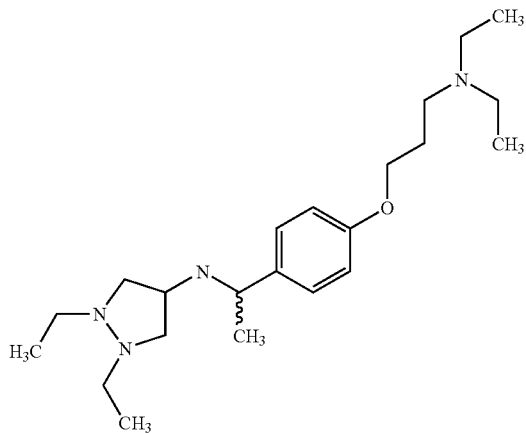 | 377 |
| 21 | 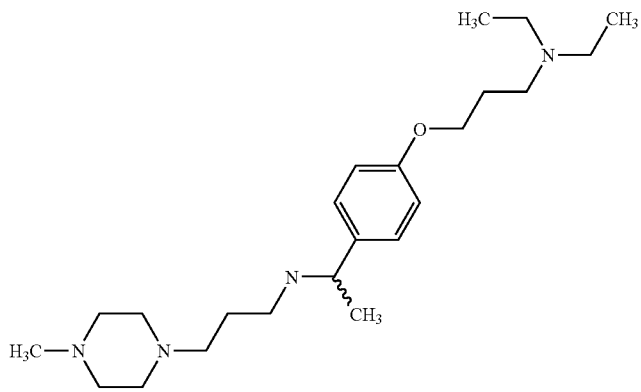 | 391 |

-continued
| Example Number | Structure | Observed Mass |
|---|---|---|
| 22 | 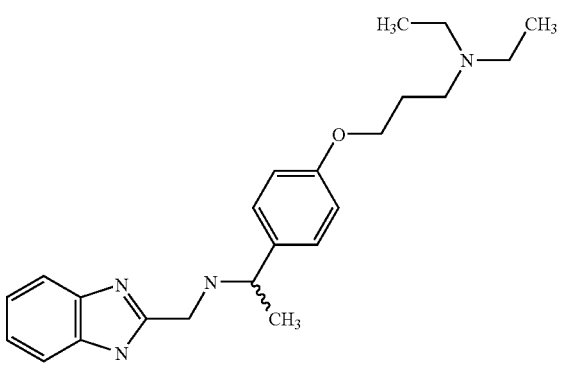 | 381 |
| 23 | 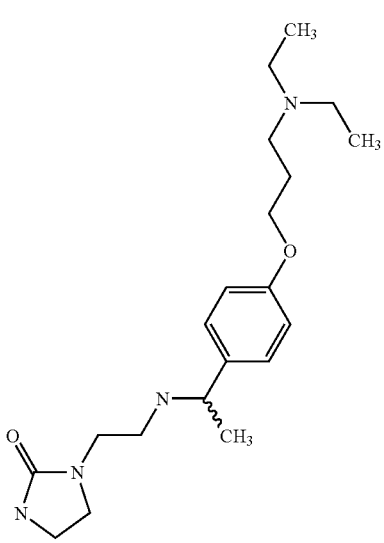 | 376 |
| 24 | 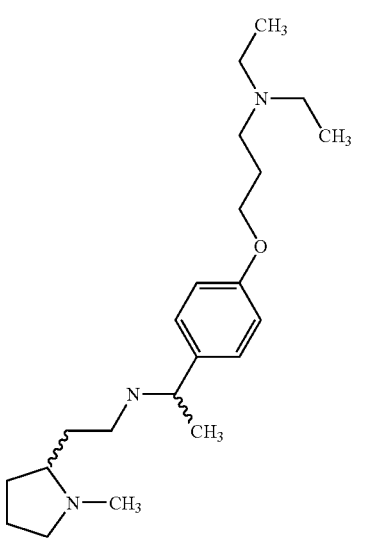 | 362 |

-continued

| Example Number | Structure | Observed Mass |
|---|---|---|
| 25 | 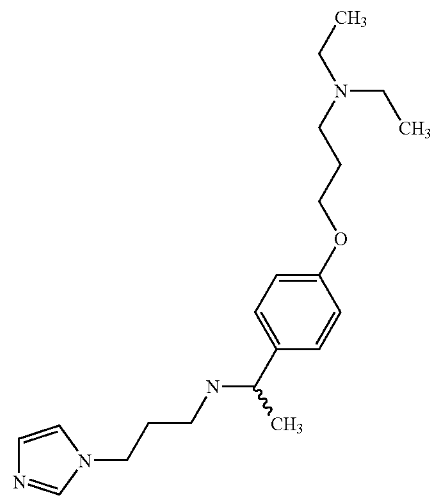 | 359 |
| 26 | 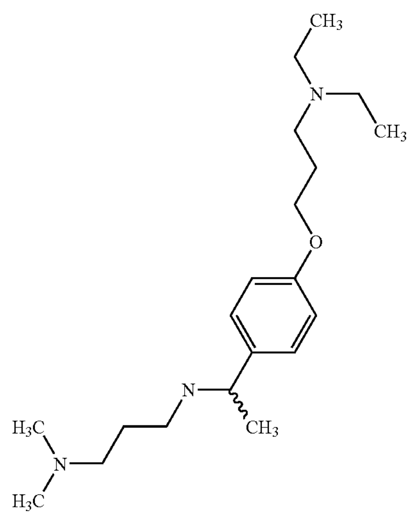 | 336 |
| 27 | 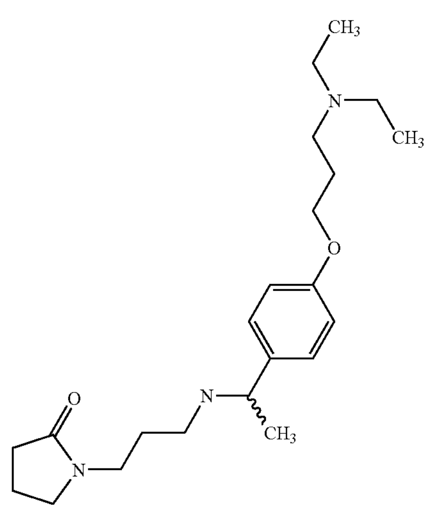 | 376 |

-continued

| Example Number | Structure | Observed Mass |
|---|---|---|
| 28 | 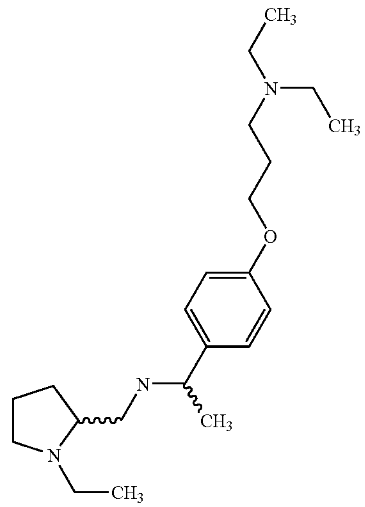 | 362 |
| 29 | 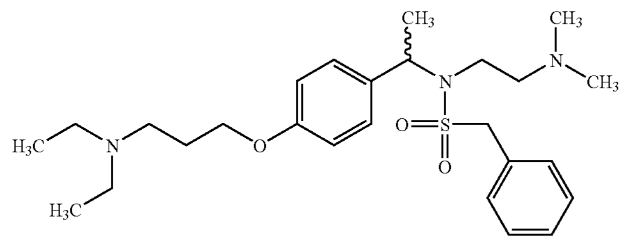 | 476 |
| 30 | 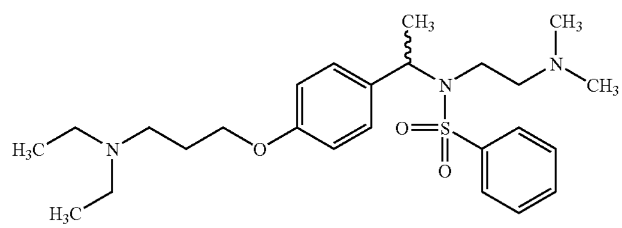 | 462 |
| 31 | 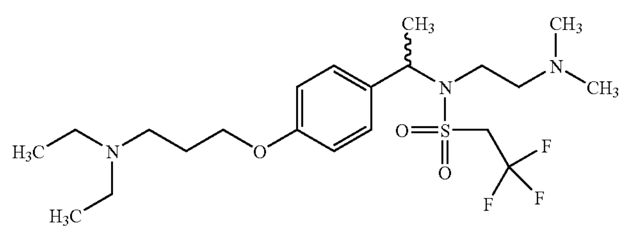 | 468 |
| 32 | 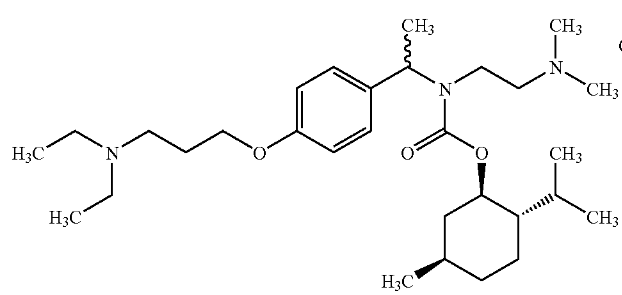 | |

-continued

| Example Number | Structure | Observed Mass |
|---|---|---|
| 33 | 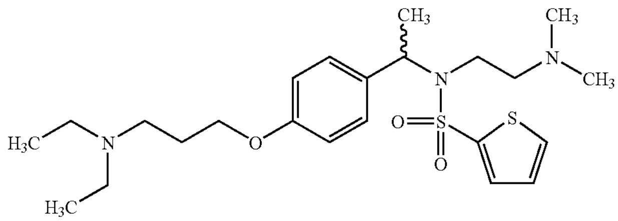 | 468 |
| 34 | 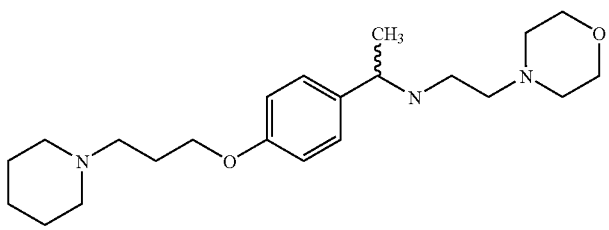 | |
| 35 | 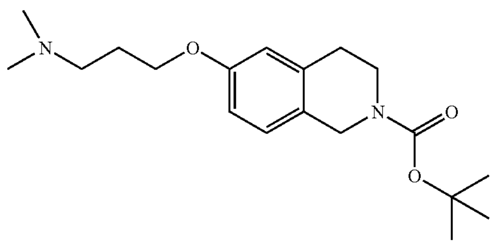 | 335 |
| 36 | 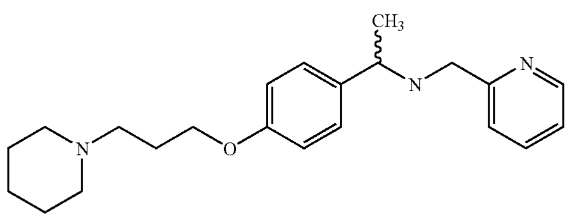 | 354 |
| 37 | 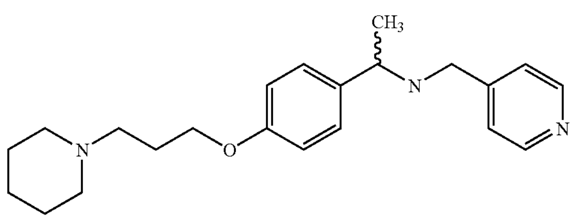 | 354 |
| 38 | 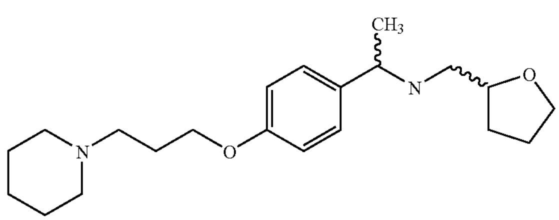 | |
| 39 | 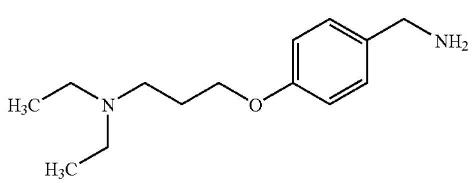 | |

| Example Number | Structure | Observed Mass |
|---|---|---|
| 40 | ![structure] N,N-dimethyl-3-[(1,2,3,4-tetrahydroisoquinolin-6-yl)oxy]propan-1-amine · 2 HCl | 235 |
| 41 | ![structure] (Chiral) | 361 |
| 42 | ![structure] (Chiral) | 361 |
| 43 | ![structure] (Chiral) | 401 |
| 44 | ![structure] | 389 |
| 45 | ![structure] | 362 |
| 46 | ![structure] | 346 |

| Example Number | Structure | Observed Mass |
|---|---|---|
| 47 | 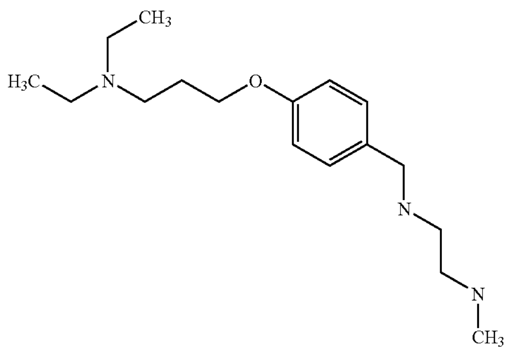 | 294 |
| 48 | 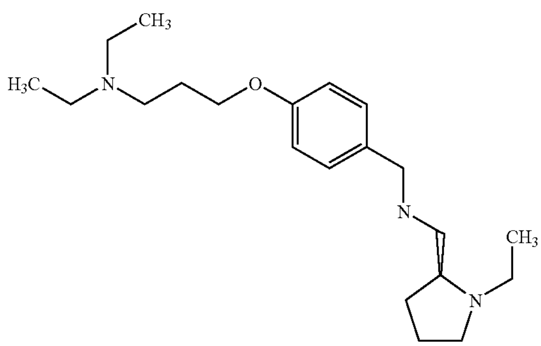 | 348 |
| 49 | 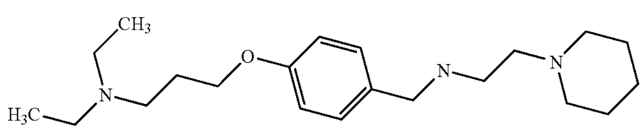 | 348 |
| 50 | 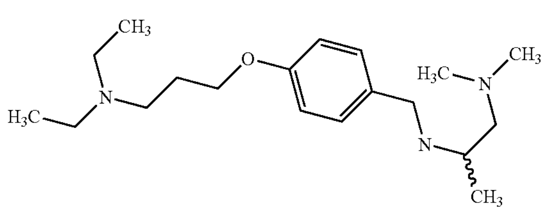 | 322 |
| 51 | 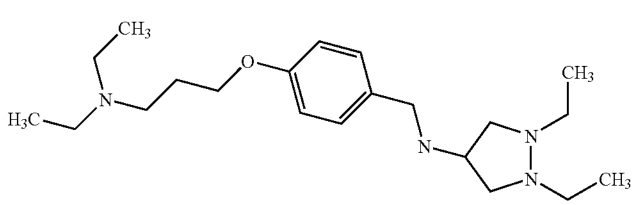 | 363 |

-continued
| Example Number | Structure | Observed Mass |
|---|---|---|
| 52 | 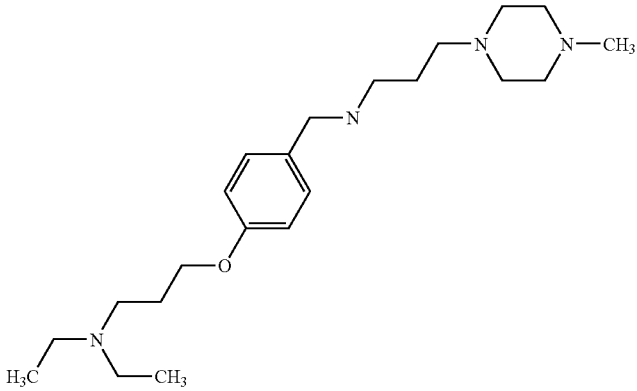 | 377 |
| 53 | 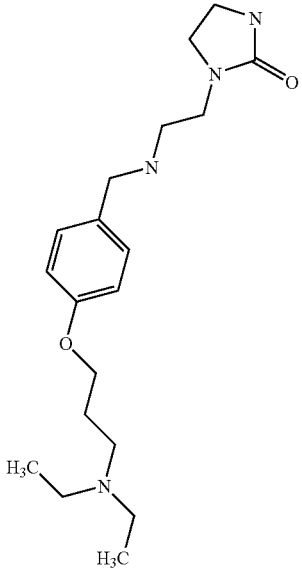 | 349 |
| 54 | 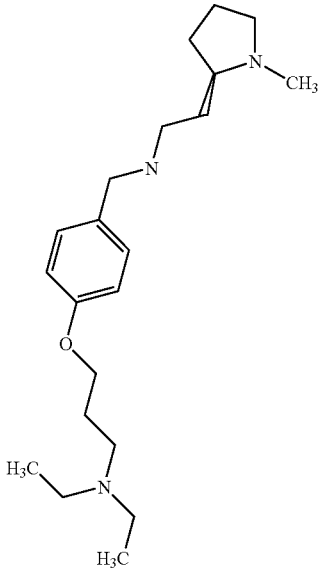 | 348 |

| Example Number | Structure | Observed Mass |
|---|---|---|
| 55 | 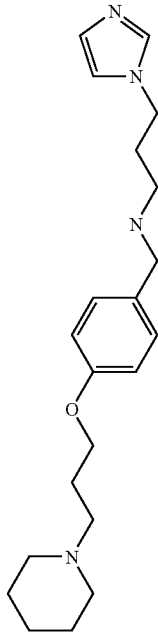 | 357 |
| 56 | 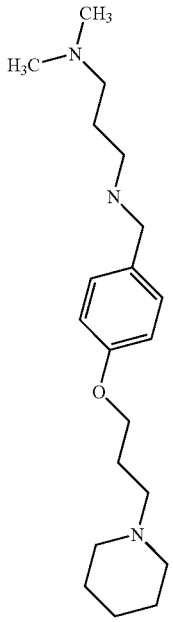 | 334 |

| Example Number | Structure | Observed Mass |
|---|---|---|
| 57 | 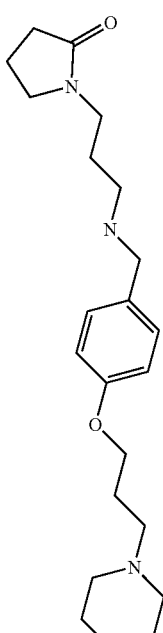 | 374 |
| 58 | 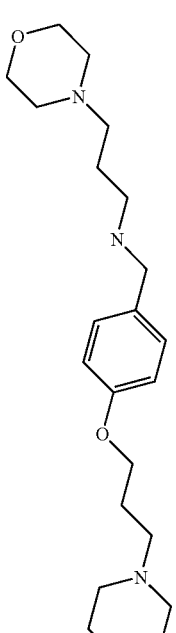 | 376 |
| 59 | 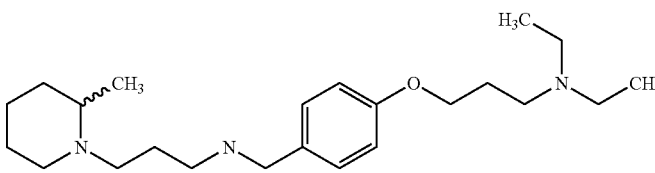 | 376 |

-continued

| Example Number | Structure | Observed Mass |
|---|---|---|
| 60 | 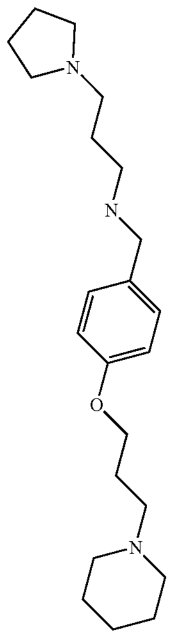 | 360 |
| 61 | 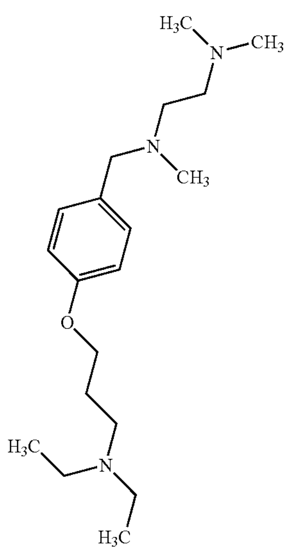 | 322 |
| 62 | 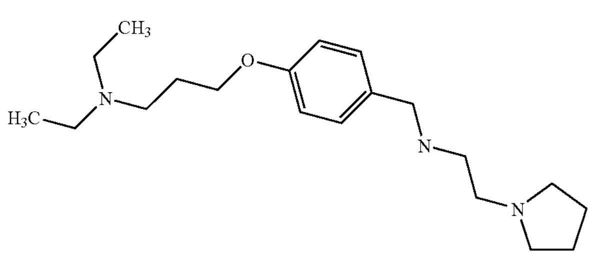 | 350 |

-continued
| Example Number | Structure | Observed Mass |
|---|---|---|
| 63 | 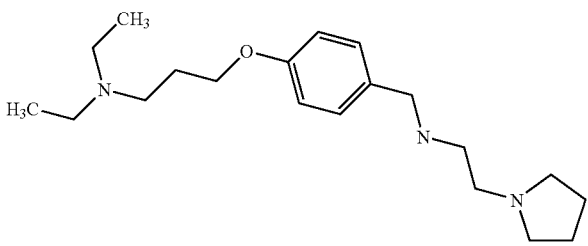 | 334 |
| 64 | 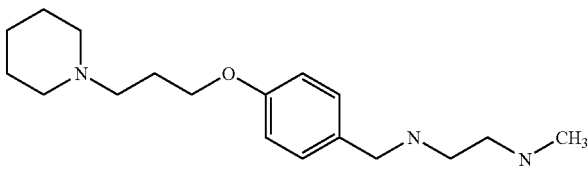 | 306 |
| 65 | 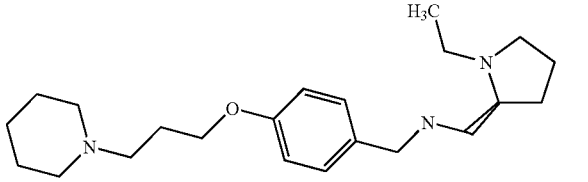 | 360 |
| 66 | 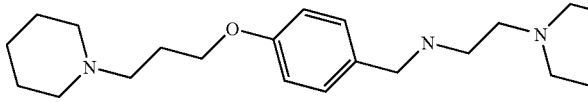 | 360 |
| 67 | 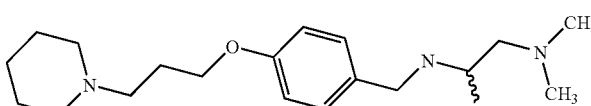 | 334 |
| 68 | 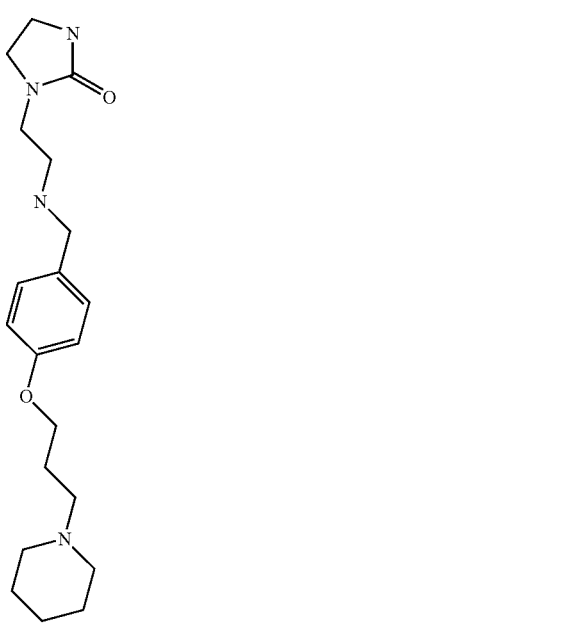 | 361 |

-continued

| Example Number | Structure | Observed Mass |
|---|---|---|
| 69 | 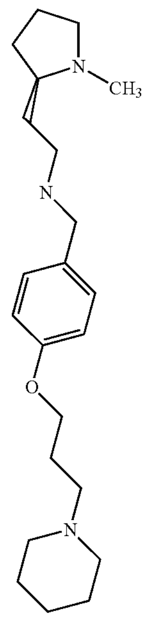 | 360 |
| 70 | 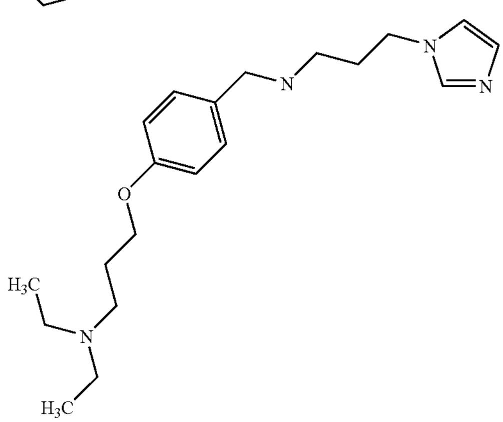 | 345 |
| 71 | 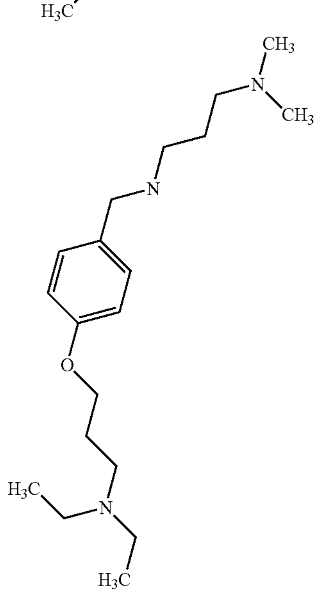 | 322 |

-continued
| Example Number | Structure | Observed Mass |
|---|---|---|
| 72 | 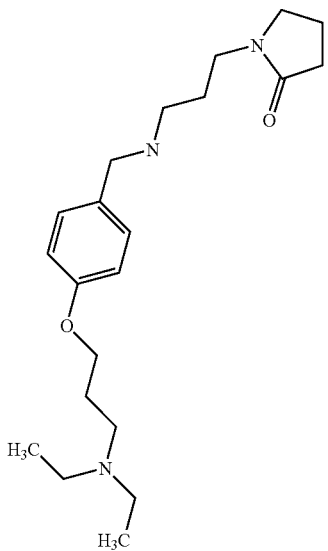 | 362 |
| 73 | 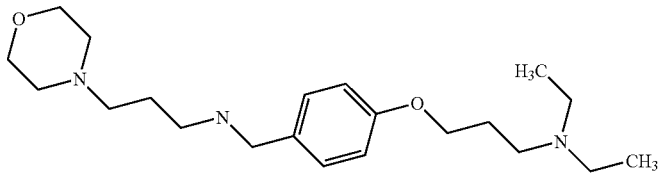 | 364 |
| 74 | 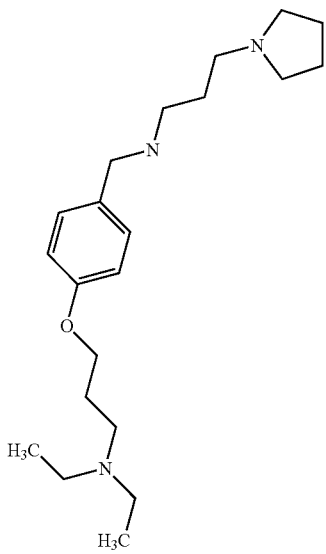 | 348 |

-continued
| Example Number | Structure | Observed Mass |
|---|---|---|
| 75 | 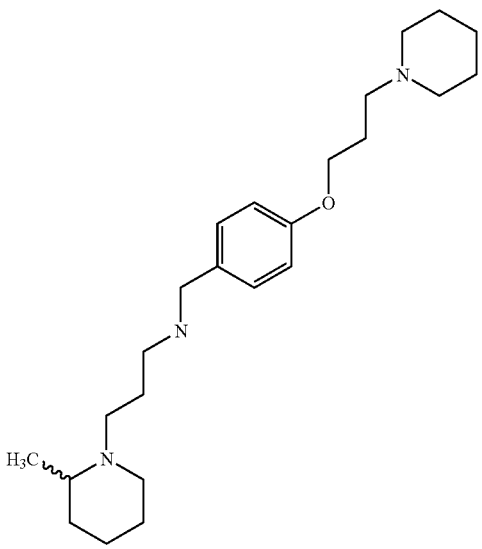 | 388 |
| 76 | 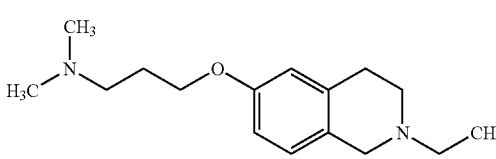 | 263 |
| 77 | 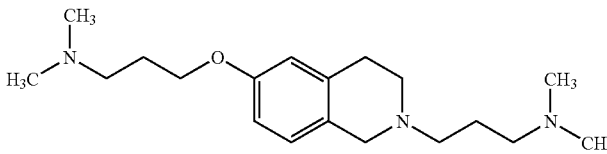 | 320 |
| 78 | 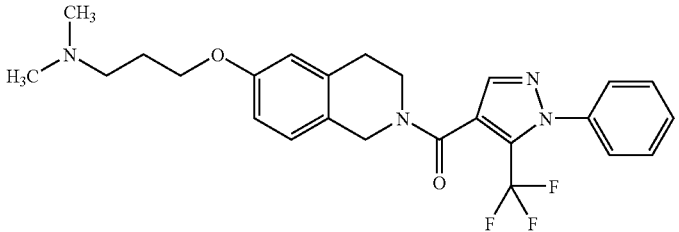 | 474 |
| 79 | 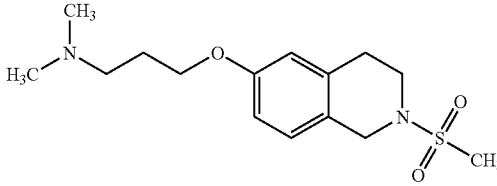 | 360 |
| 80 | 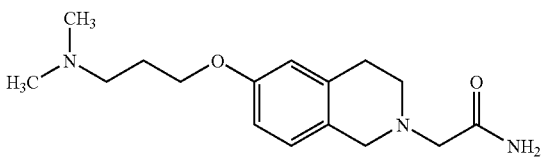 | 292 |

-continued

| Example Number | Structure | Observed Mass |
|---|---|---|
| 81 | 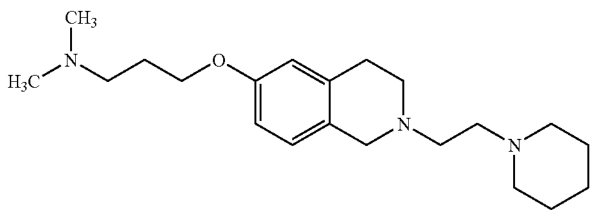 | 346 |
| 82 | 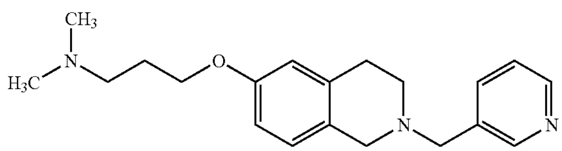 | 326 |
| 83 | 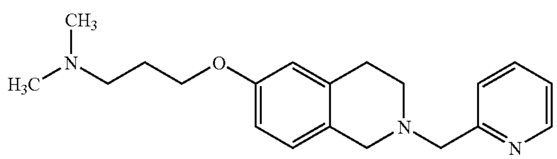 | 326 |
| 84 | 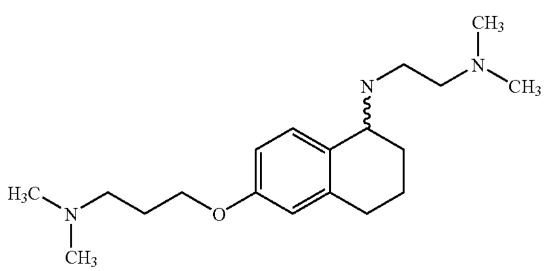 | |
| 85 | 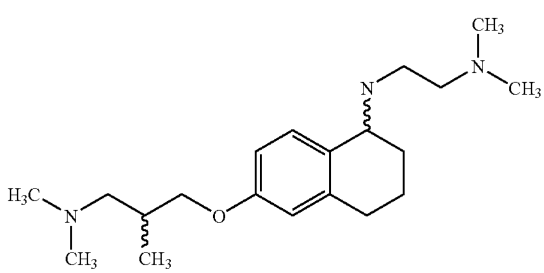 | 246 |
| 86 | 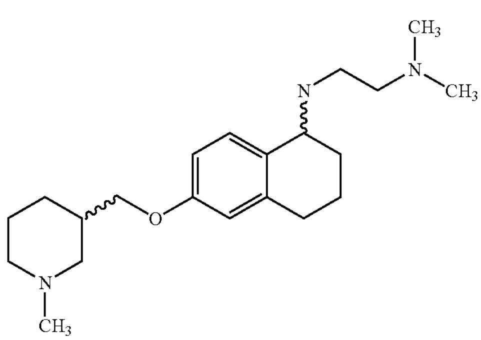 | 346 |

-continued

| Example Number | Structure | Observed Mass |
|---|---|---|
| 87 | 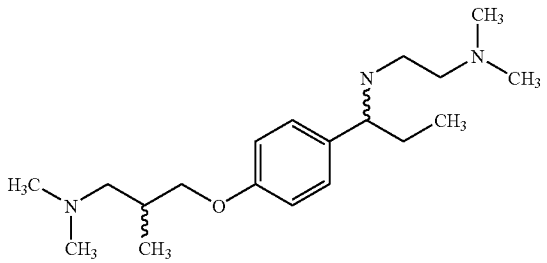 | 322 |
| 88 | 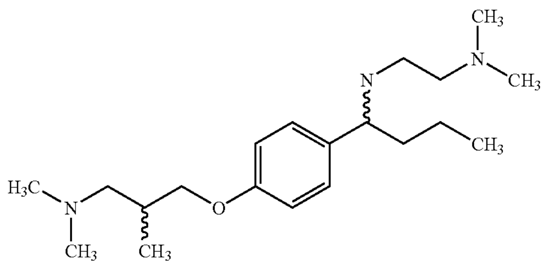 | 336 |
| 89 | 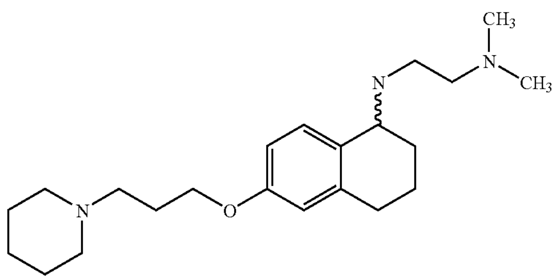 | 272 |
| 90 | 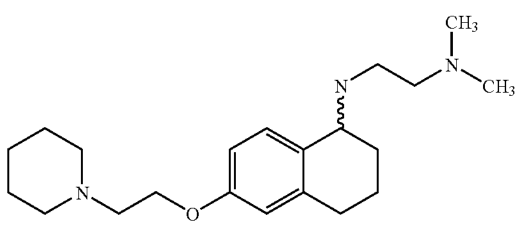 | 258 |
| 91 | 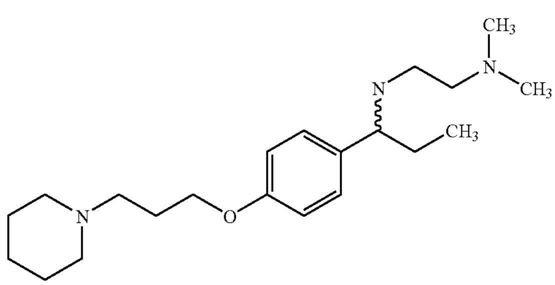 | 348 |
| 92 | 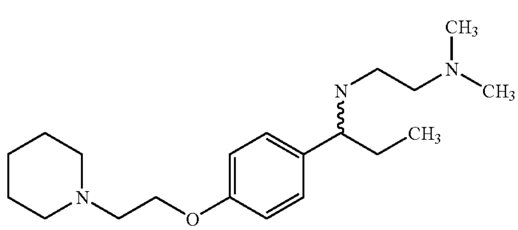 | 334 |

-continued

| Example Number | Structure | Observed Mass |
|---|---|---|
| 93 | 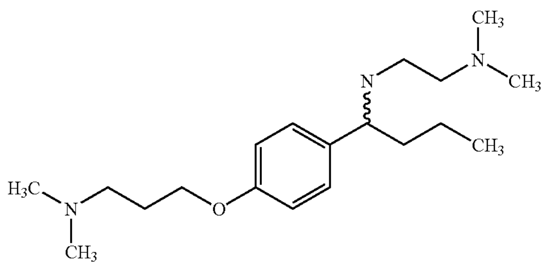 | 322 |
| 94 | 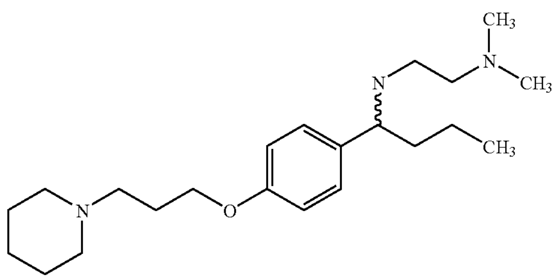 | 362 |
| 95 | 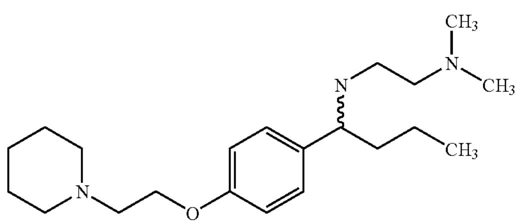 | 348 |
| 96 | 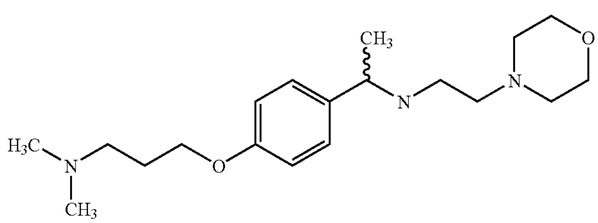 | 335 |
| 97 | 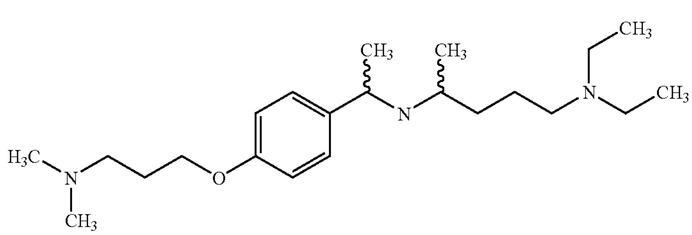 | 363 |
| 98 | 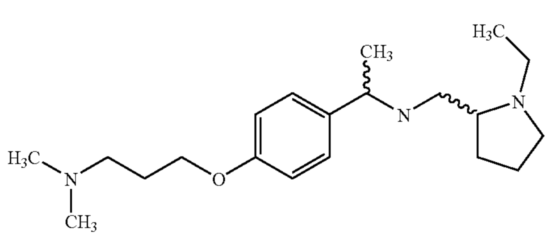 | 333 |

-continued
| Example Number | Structure | Observed Mass |
|---|---|---|
| 99 | 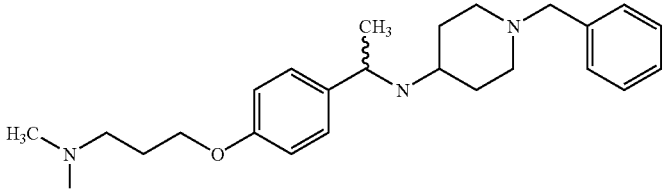 | 393 |
| 100 | 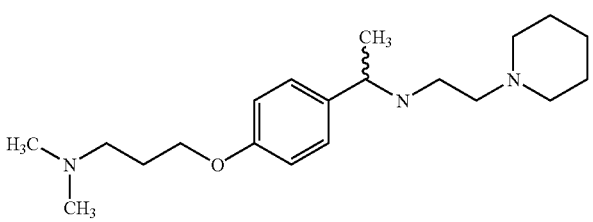 | 334 |
| 101 | 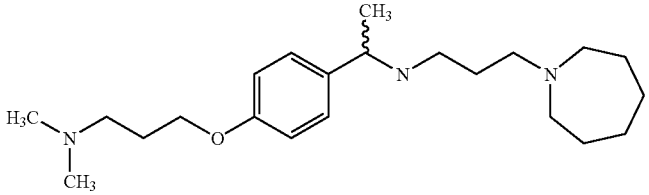 | 361 |
| 102 | 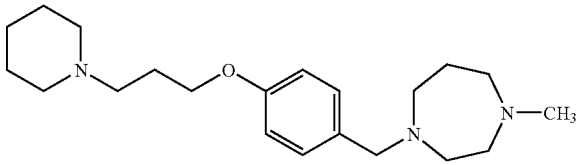 | 346 |
| 103 | 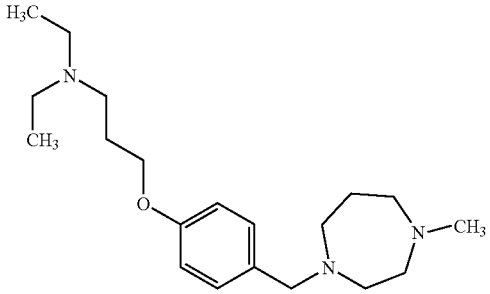 | 334 |
| 104 | 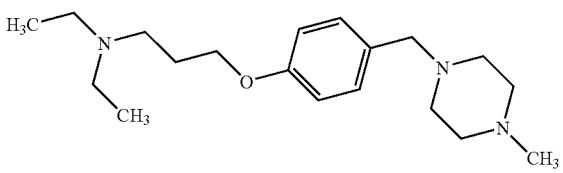 | 320 |
| 105 | 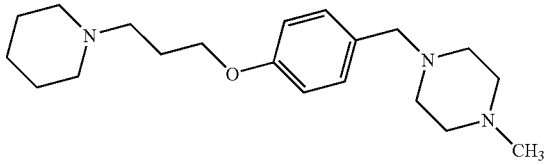 | 332 |

-continued
| Example Number | Structure | Observed Mass |
|---|---|---|
| 106 | 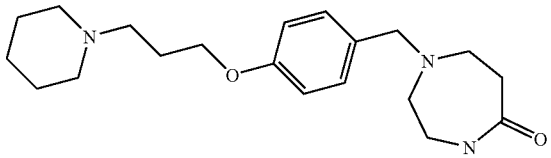 | 346 |
| 107 | 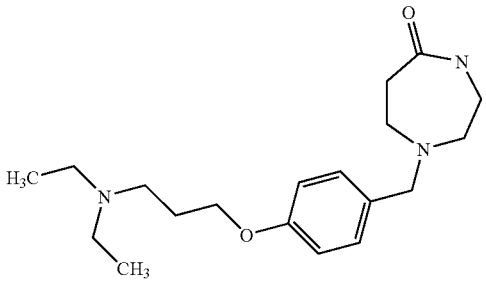 | 334 |
| 108 | 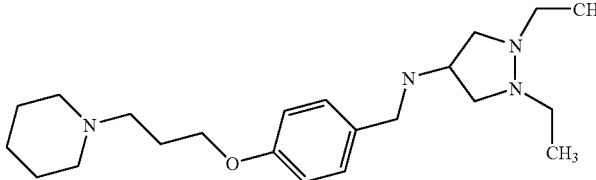 | 375 |
| 109 | 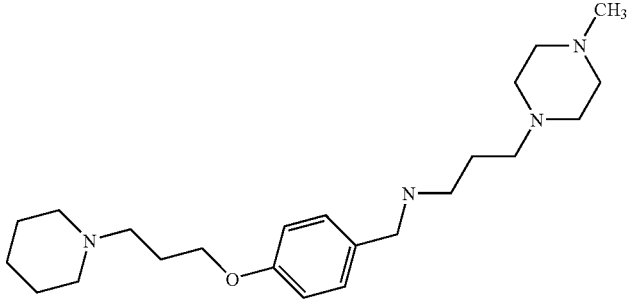 | 389 |
| 110 | 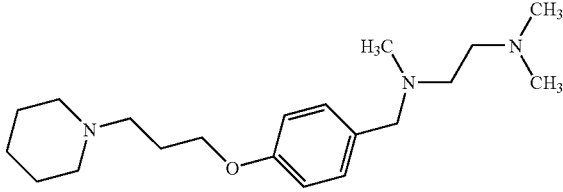 | 334 |
| 111 | 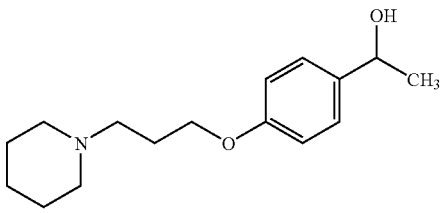 | 364.1 |

-continued
| Example Number | Structure | Observed Mass |
|---|---|---|
| 112 | 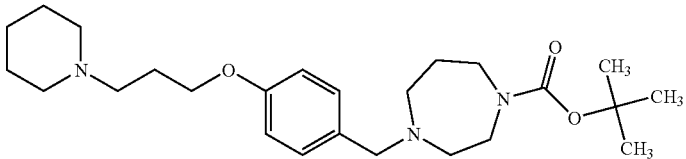 | 432 |
| 113 | 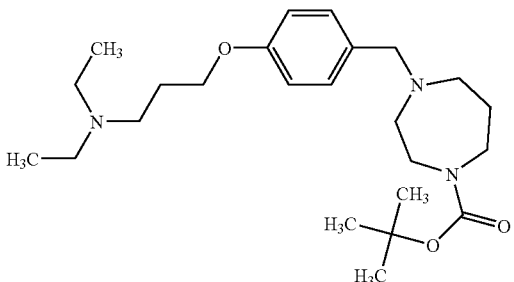 | 420 |
| 114 | 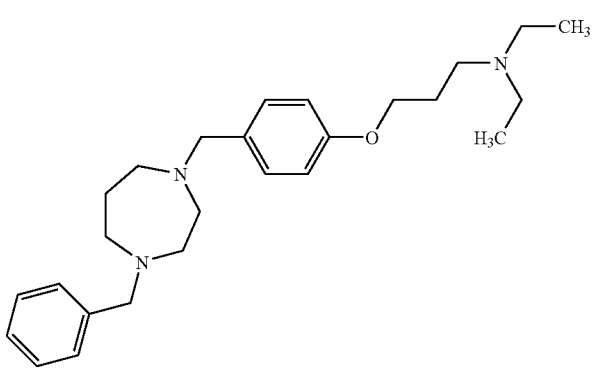 | 410 |
| 115 | 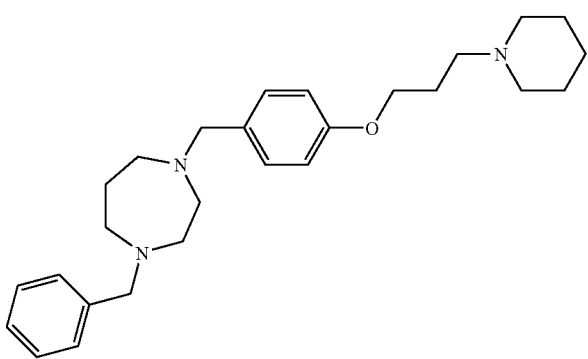 | 410 |
| 116 | 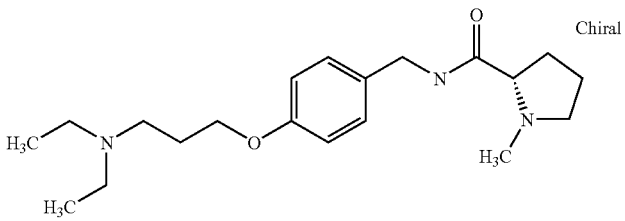 | 348 |

-continued

| Example Number | Structure | Observed Mass |
|---|---|---|
| 117 | 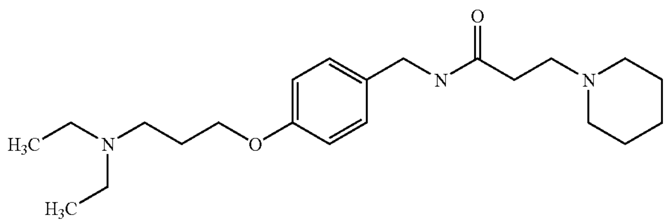 | 376 |
| 118 | 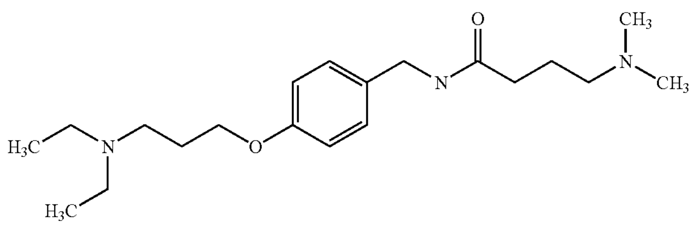 | 350 |
| 119 | 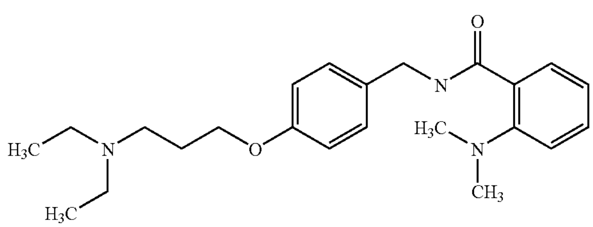 | 384 |
| 120 | (Chiral) | 391 |
| 121 | 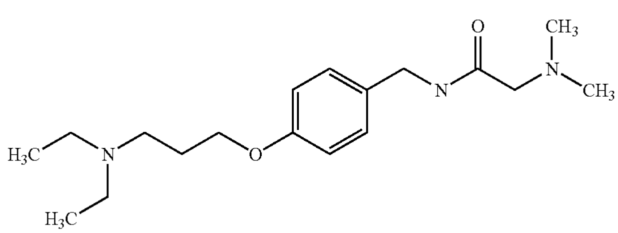 | 322 |
| 122 | 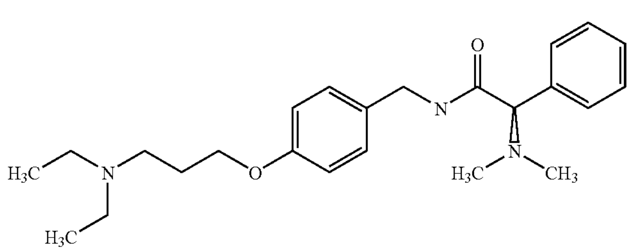 | 398 |

-continued

| Example Number | Structure | Observed Mass |
|---|---|---|
| 123 | 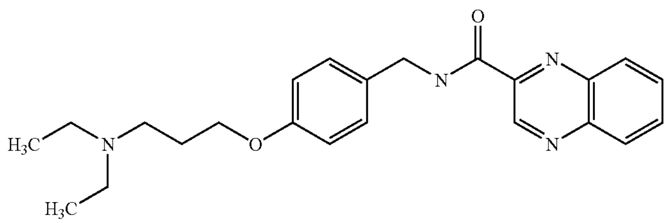 | 393 |
| 124 | 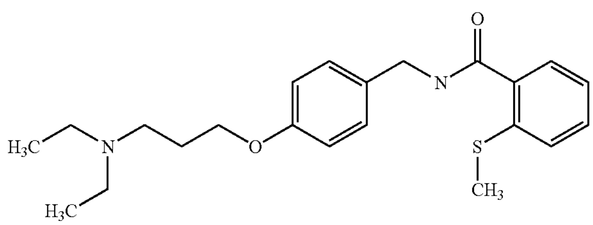 | 388 |
| 125 | 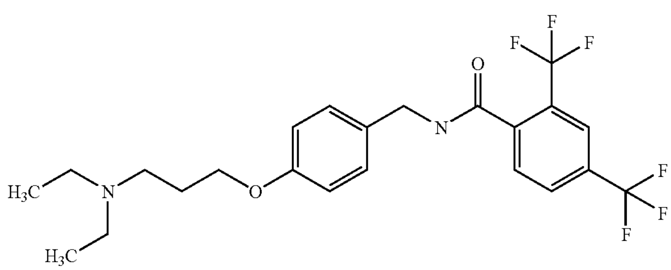 | 477 |
| 126 | 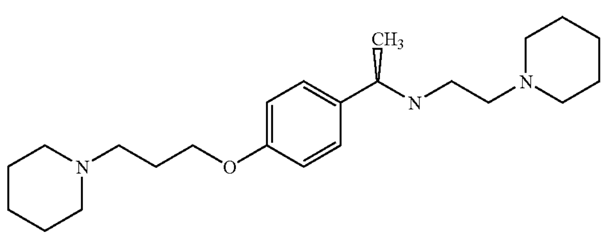 | 375 |
| 127 | 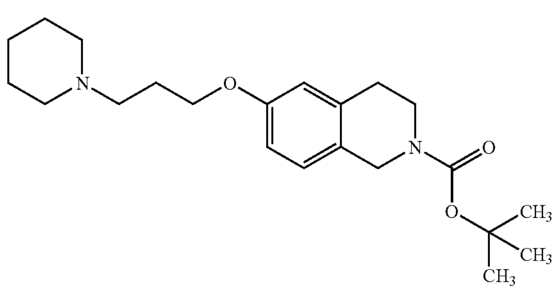 | 375 |
| 128 | 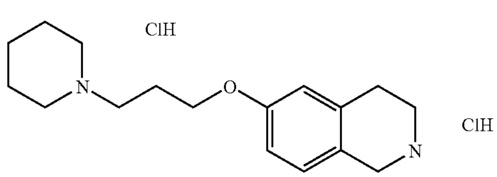 | 275 |

-continued

| Example Number | Structure | Observed Mass |
|---|---|---|
| 129 | 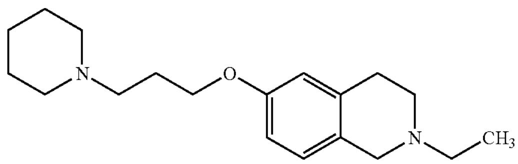 | 303 |
| 130 | Chiral | 386 |
| 131 | Chiral | 386 |
| 132 | Chiral | 401 |
| 133 | Chiral | 372 |
| 134 | 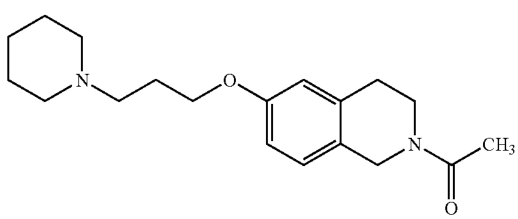 | 315 |
| 135 | 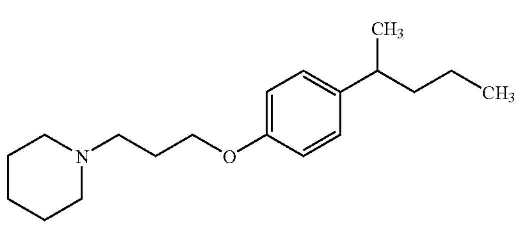 | 292 |

US 7,314,937 B2
123                                                                                      124
-continued
| Example Number | Structure | Observed Mass |
|---|---|---|
| 136 | 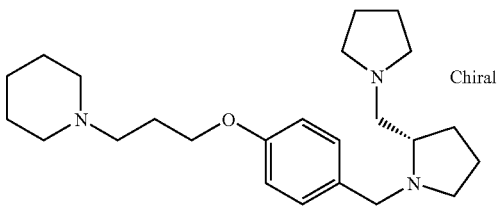 | 386 |
| 137 | 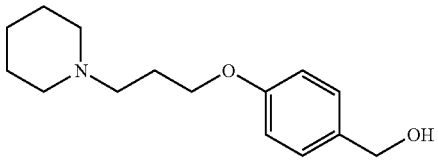 | 250 |
| 138 | 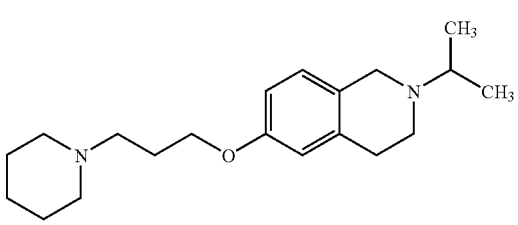 | 317 |
| 139 | 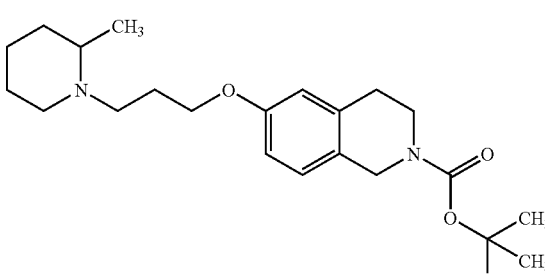 | 389 |
| 140 | 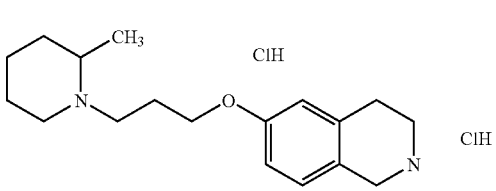 | 289 |
| 141 | 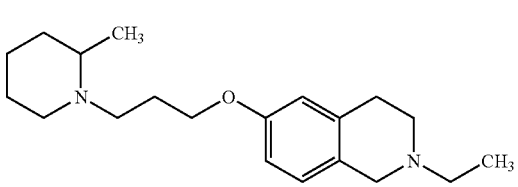 | 317 |
| 142 | 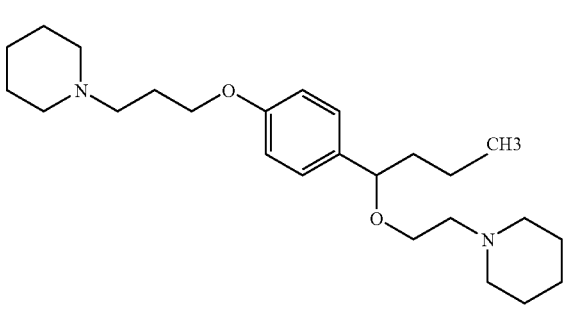 | 404 |

-continued
| Example Number | Structure | Observed Mass |
|---|---|---|
| 143 | 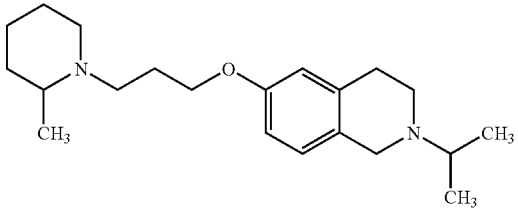 | 331 |
| 144 | 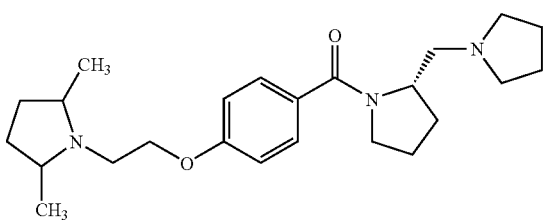 Chiral | 400 |
| 145 | 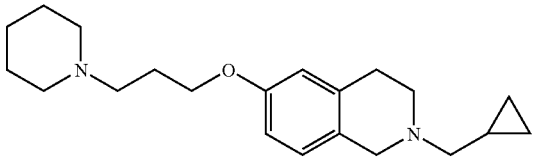 | 329 |
| 146 | 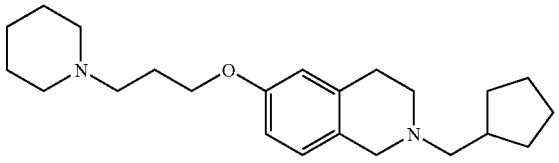 | 357 |
| 147 | 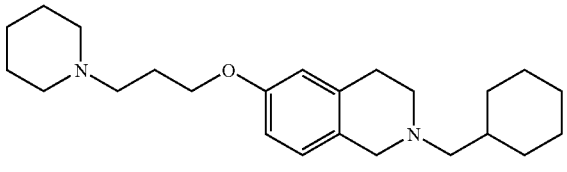 | 371 |
| 148 | 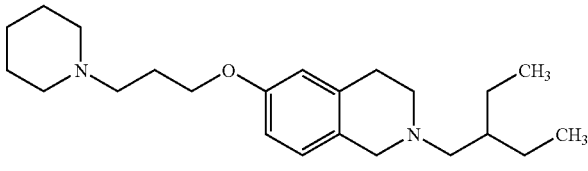 | 359 |
| 149 | 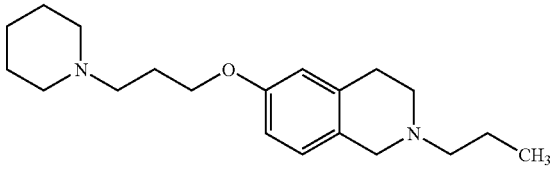 | 317 |
| 150 | 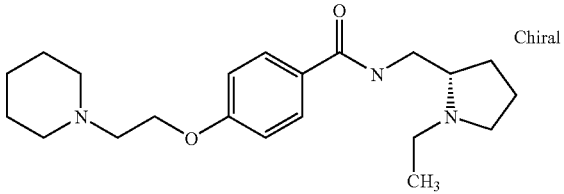 Chiral | 360 |

US 7,314,937 B2
127                                                                            128
-continued
| Example Number | Structure | Observed Mass |
|---|---|---|
| 151 | 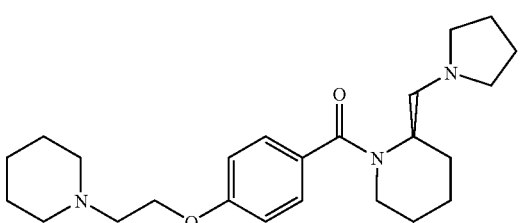 | 340 |
| 152 | 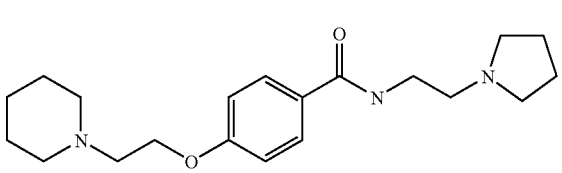 | 346 |
| 153 | 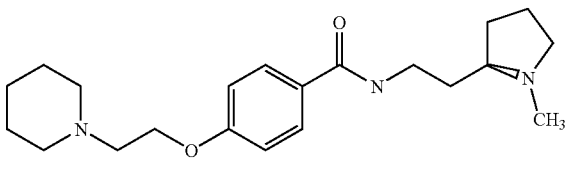 | 360 |
| 154 | 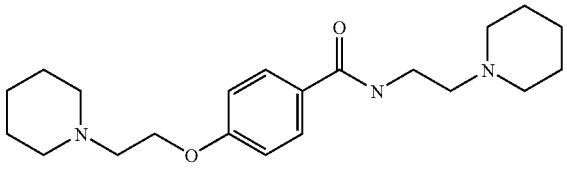 | 360 |
| 155 | 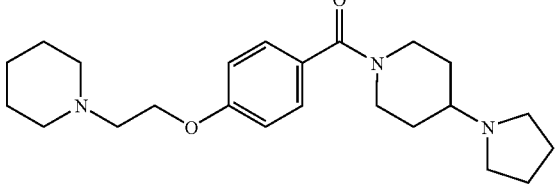 | 386 |
| 156 | 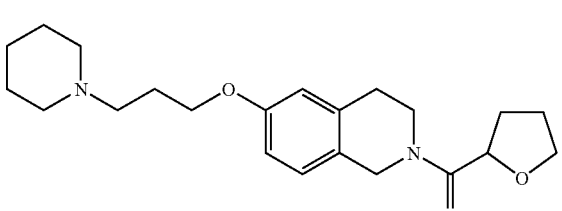 | 386 |
| 157 | 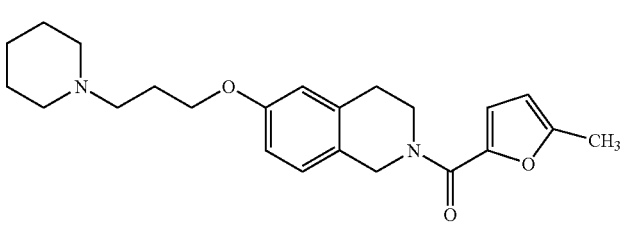 | 383 |

-continued

| Example Number | Structure | Observed Mass |
|---|---|---|
| 158 | 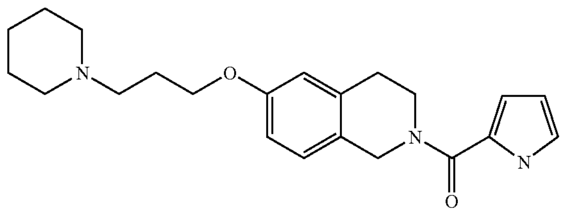 | 368 |
| 159 | 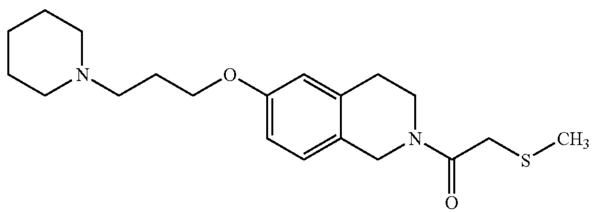 | 363 |
| 160 | 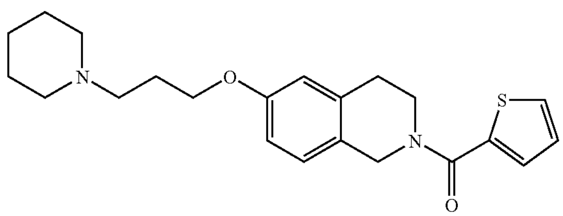 | 385 |
| 161 | 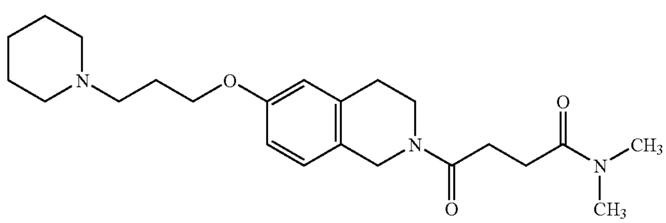 | 402 |
| 162 | 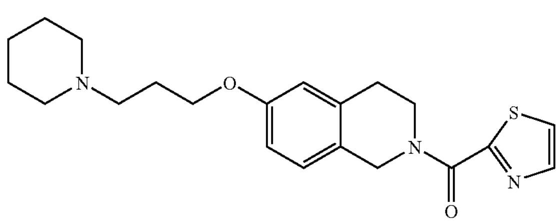 | 386 |
| 163 | 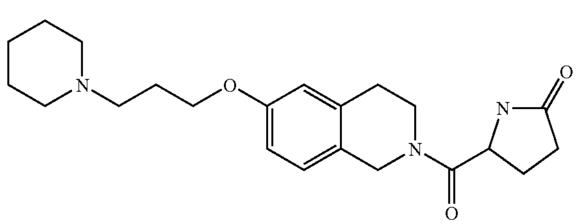 | 386 |
| 164 | 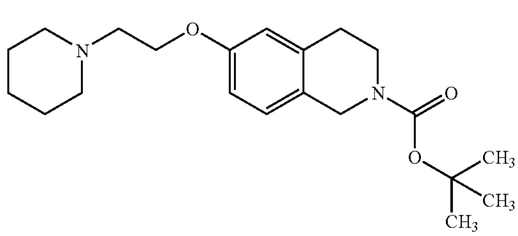 | 361 |

-continued
| Example Number | Structure | Observed Mass |
|---|---|---|
| 165 | 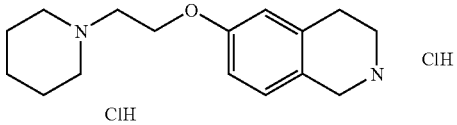 | 261 |
| 166 | 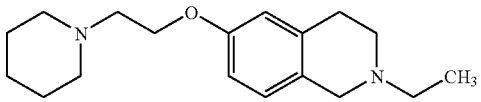 | 289 |
| 167 | 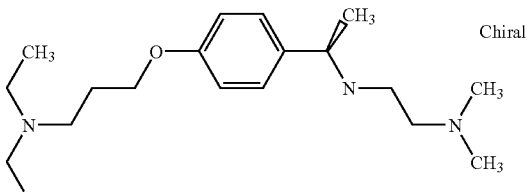 Chiral | 322 |
| 168 | 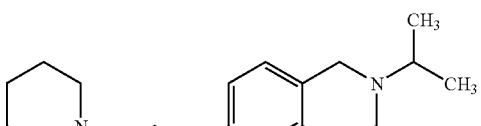 | 303 |
| 169 | 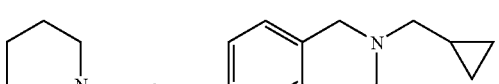 | 315 |
| 170 | 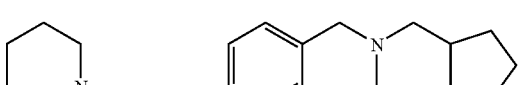 | 343 |
| 171 | 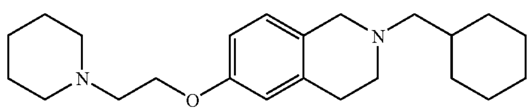 | 357 |
| 172 | 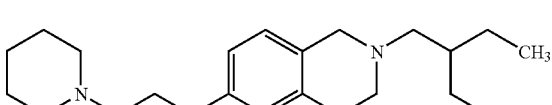 | 345 |
| 173 | 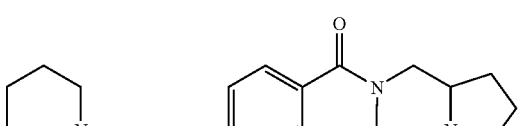 | 358 |
| 174 | 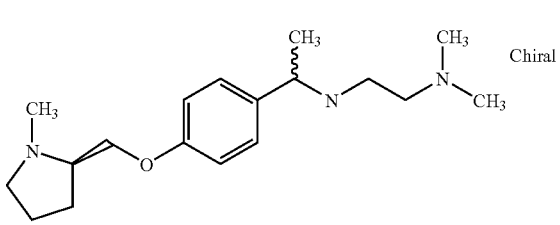 Chiral | 306 |

-continued
| Example Number | Structure | Observed Mass |
|---|---|---|
| 175 | 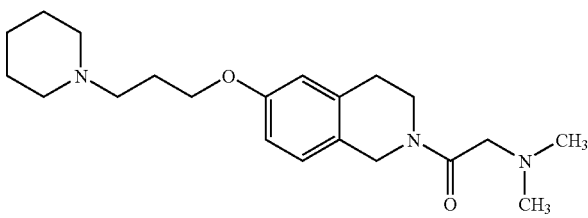 | 360 |
| 176 | 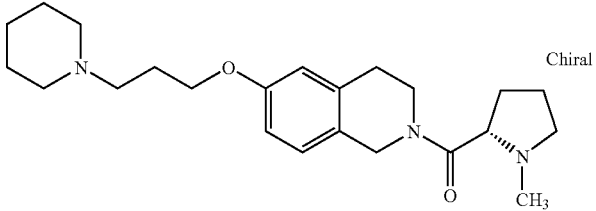 | 386 |
| 177 | 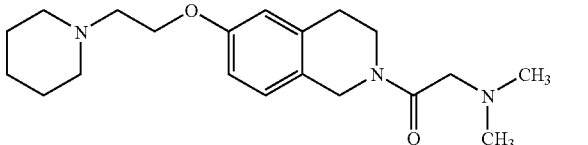 | 346 |
| 178 | 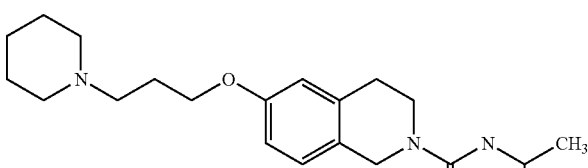 | 360 |
| 179 | 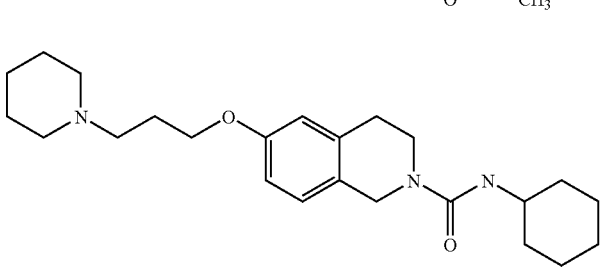 | 400 |
| 180 | 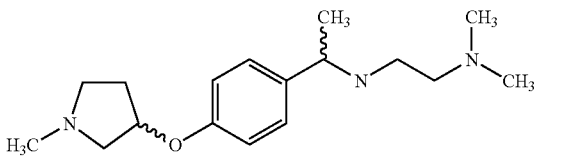 | 292 |
| 181 | 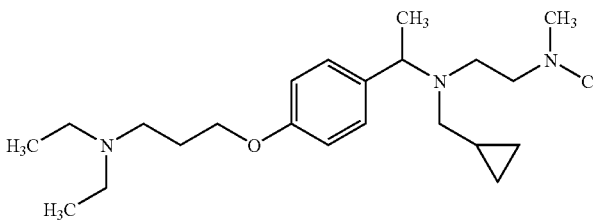 | 377 |

-continued

| Example Number | Structure | Observed Mass |
|---|---|---|
| 182 | 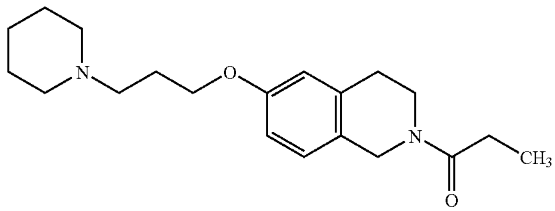 | 332 |
| 183 | 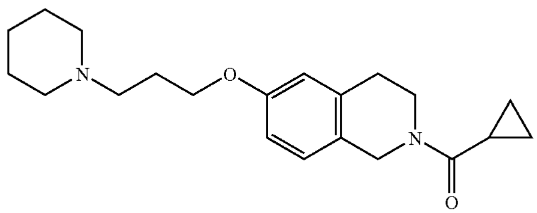 | 344 |
| 184 | 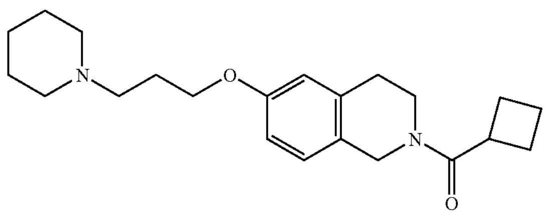 | 358 |
| 185 | 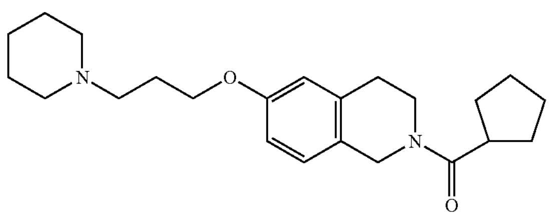 | 372 |
| 186 | 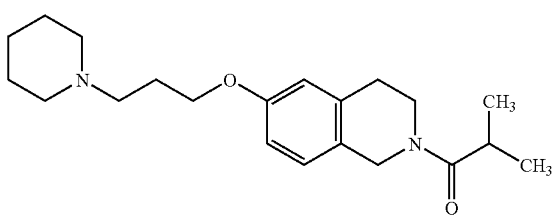 | 346 |
| 187 | 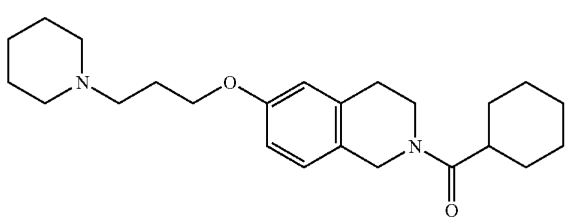 | 385 |
| 188 | 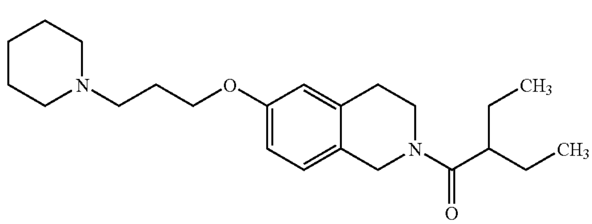 | 373 |

-continued
| Example Number | Structure | Observed Mass |
|---|---|---|
| 189 | 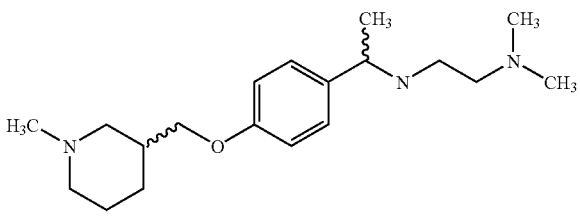 | 320 |
| 190 | 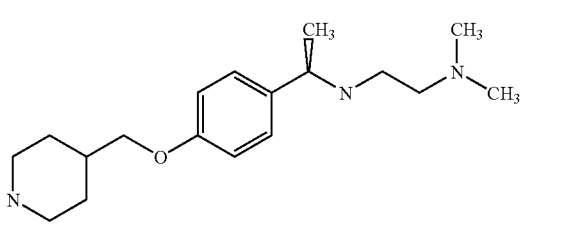 | 306 |
| 191 | 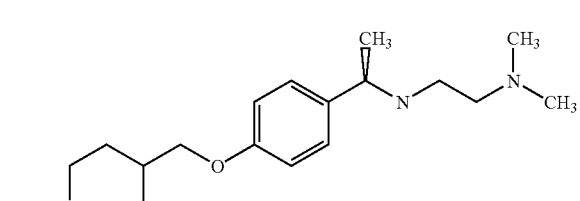 | 320 |
| 192 | 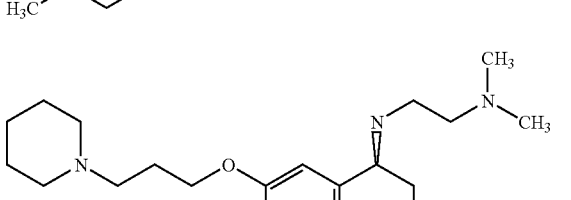 | 360 |
| 193 | 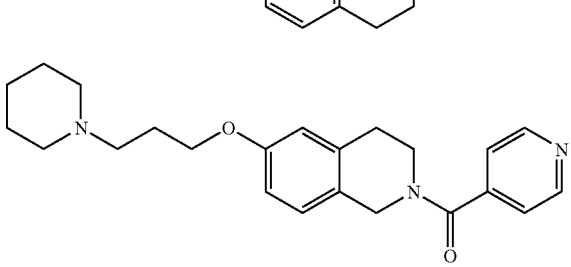 | 381 |
| 194 | 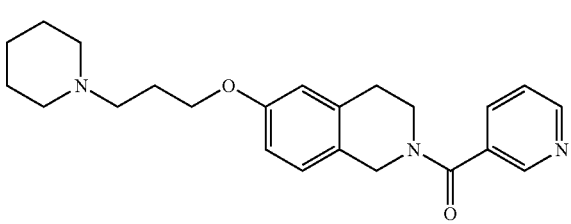 | 381 |
| 195 | 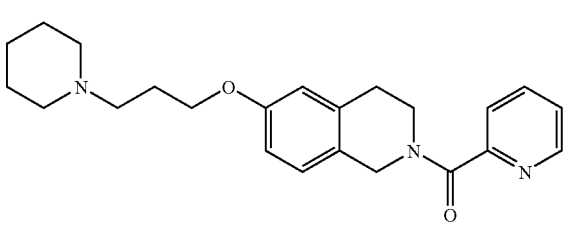 | 381 |

-continued
| Example Number | Structure | Observed Mass |
|---|---|---|
| 196 | 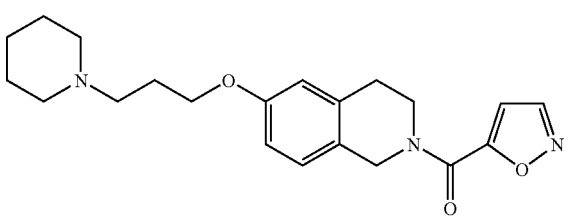 | 371 |
| 197 | 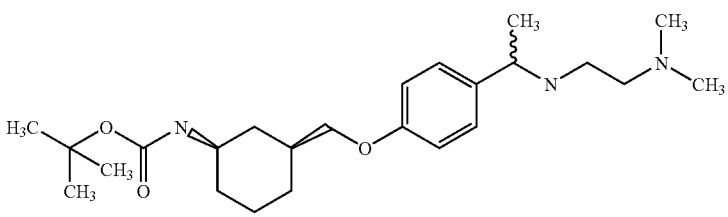 | 420 |
| 198 | 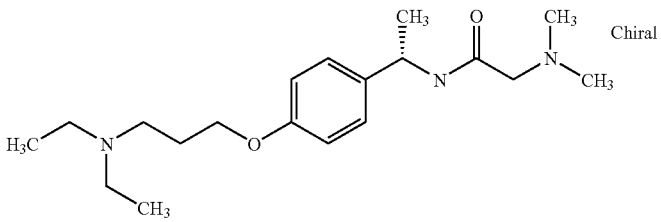 Chiral | 336 |
| 199 | 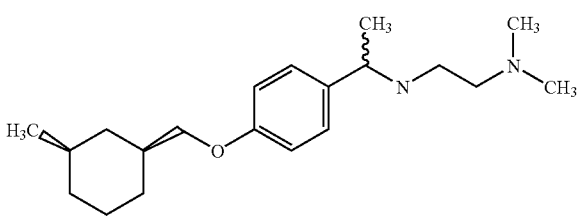 | 320 |
| 200 | 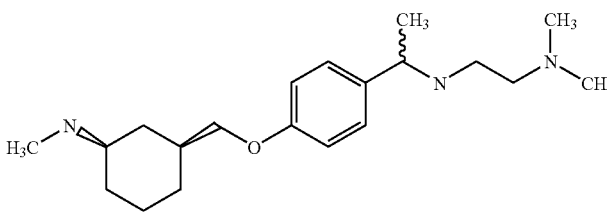 | 334 |
| 201 | 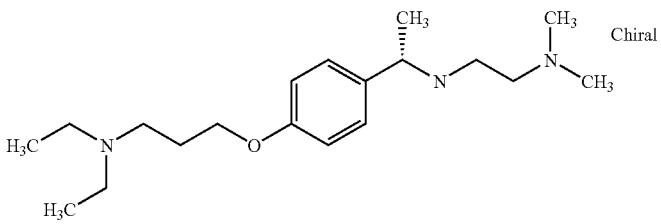 Chiral | 322 |

-continued

| Example Number | Structure | Observed Mass |
|---|---|---|
| 202 | 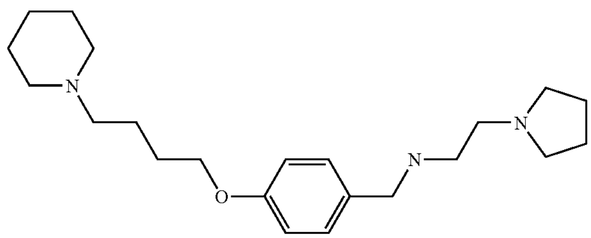 | 360.4 |
| 203 | 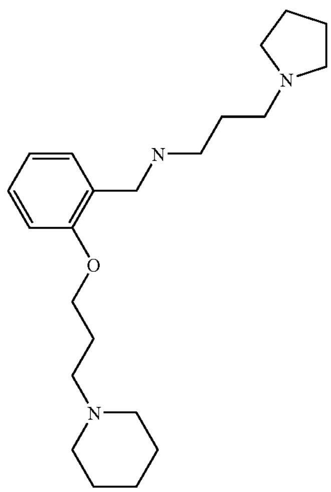 | 360.2 |
| 204 | 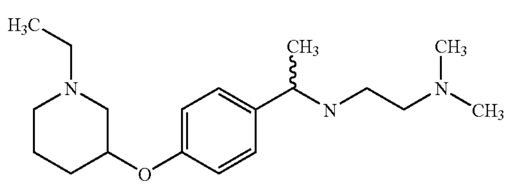 | 360.4 |
| 205 | 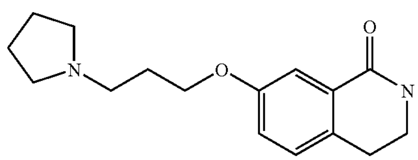 | 275.1 |
| 206 | 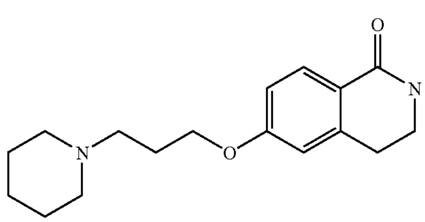 | 289.1 |
| 207 | 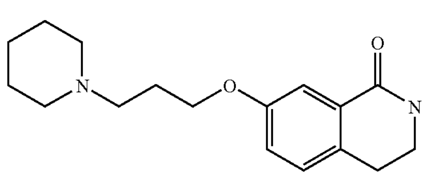 | 289.1 |

-continued
| Example Number | Structure | Observed Mass |
|---|---|---|
| 208 | 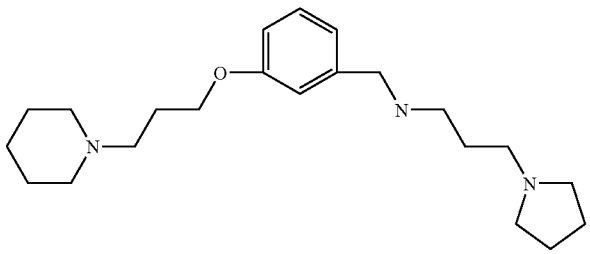 | 360.3 |
| 209 | 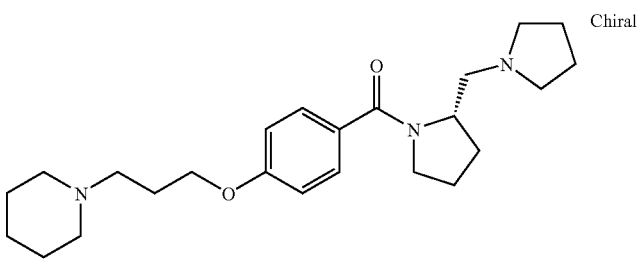 Chiral | 400 |
| 210 | 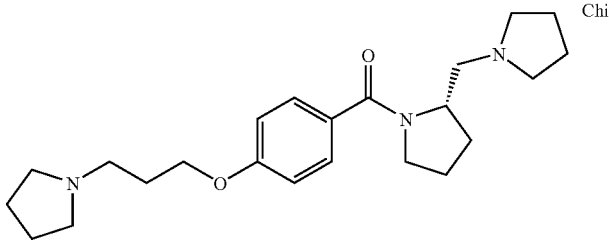 Chiral | 386 |
| 211 | 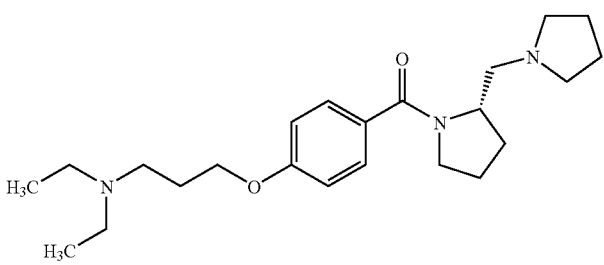 Chiral | 388 |
| 212 | 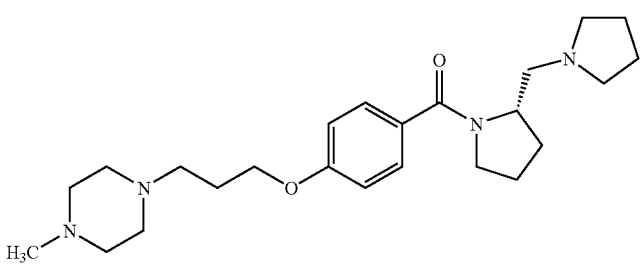 Chiral | 415 |

-continued

| Example Number | Structure | Observed Mass |
|---|---|---|
| 213 | 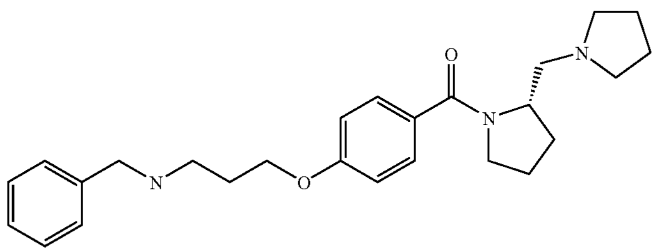 | 422 |
| 214 | 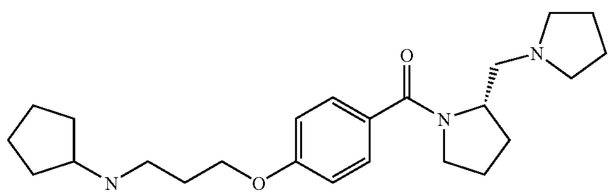 | 400 |
| 215 | 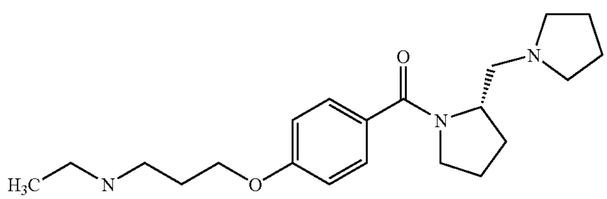 | 360 |
| 216 | 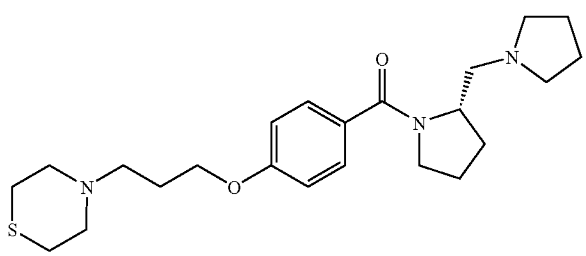 | 418 |
| 217 | 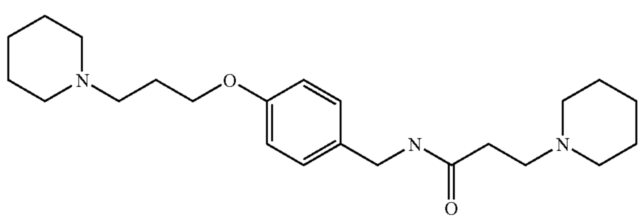 | 303.3 |
| 218 | 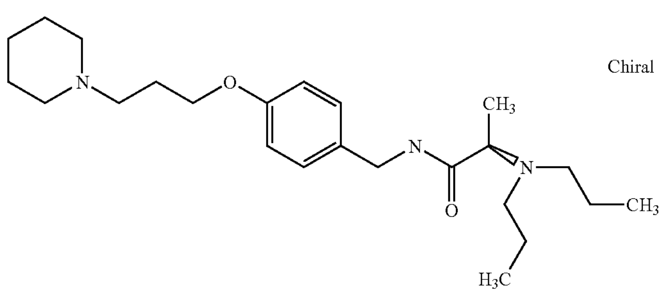 | 404 |

| Example Number | Structure | Observed Mass |
|---|---|---|
| 219 | 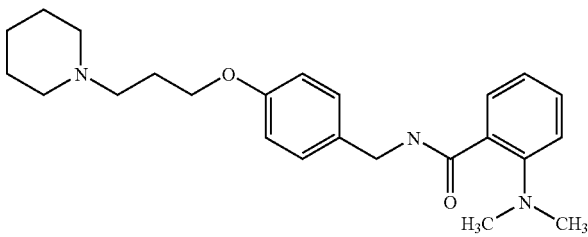 | 395 |
| 220 | 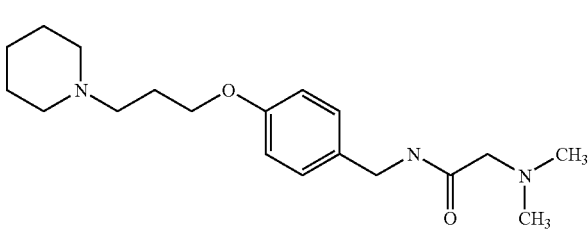 | 334 |
| 221 | 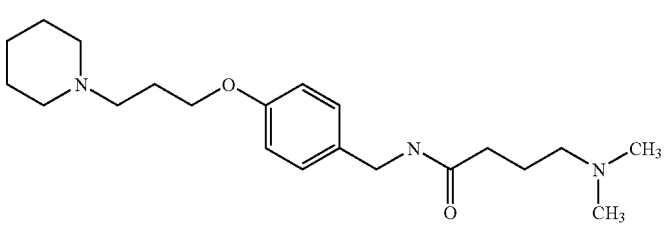 | 362 |
| 222 | 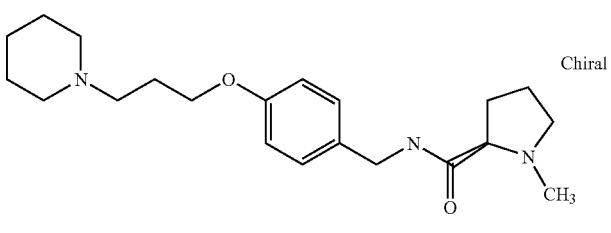 Chiral | 359 |
| 223 | 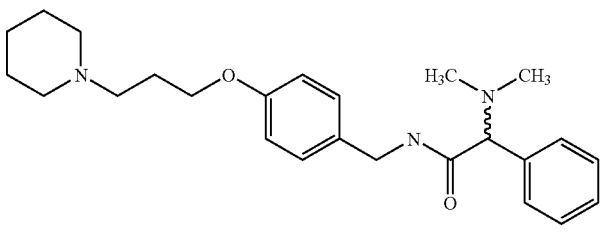 | 410 |
| 224 | 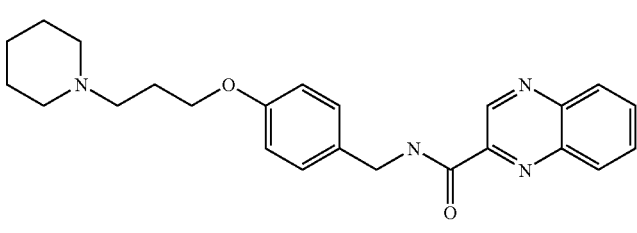 | 405 |

-continued

| Example Number | Structure | Observed Mass |
|---|---|---|
| 225 | 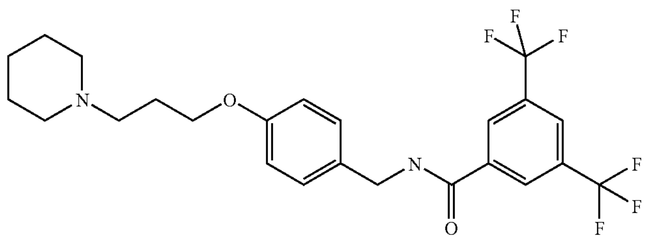 | 489 |
| 226 | 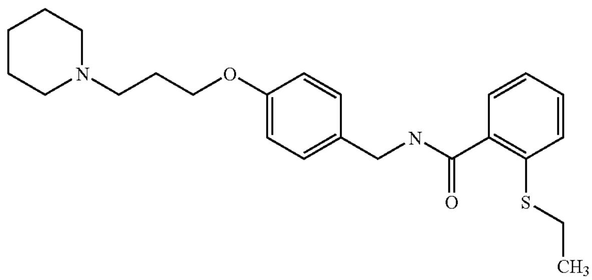 | 413 |
| 227 | 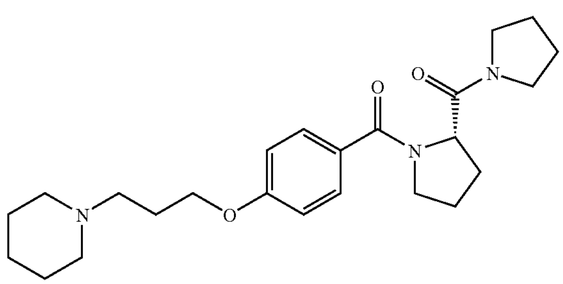 | 414 |
| 228 | 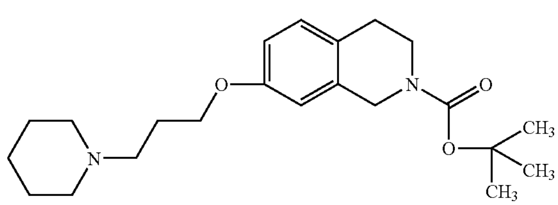 | 375.3 |
| 229 | 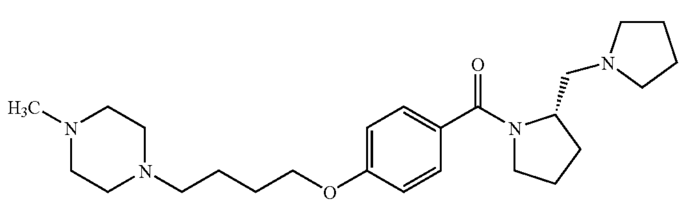 | 429 |
| 230 | 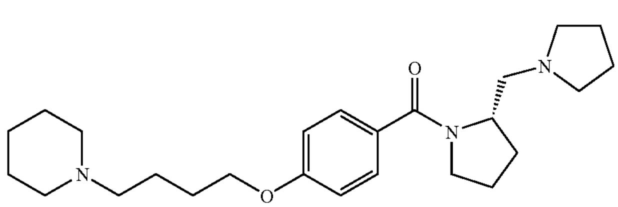 | 414 |

-continued

| Example Number | Structure | Observed Mass |
|---|---|---|
| 231 | 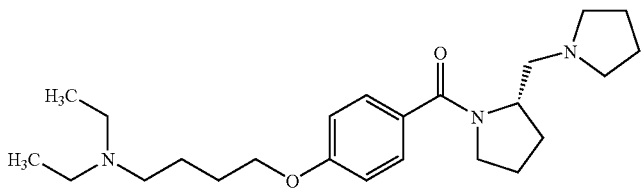 | 402 |
| 232 | 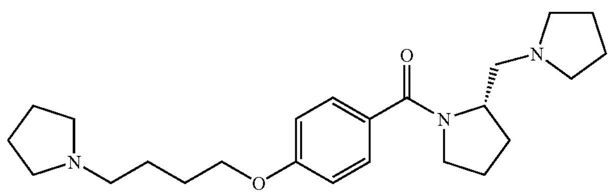 | 400 |
| 233 | 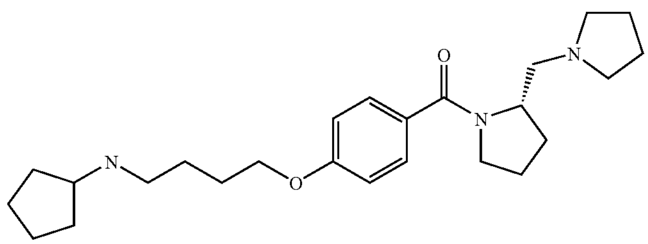 | 414 |
| 234 | 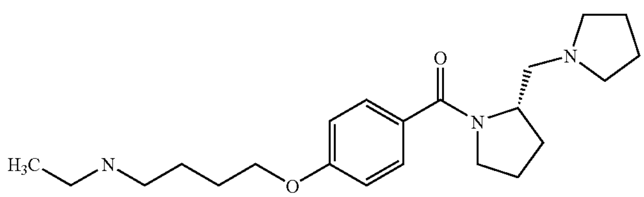 | 374 |
| 235 | 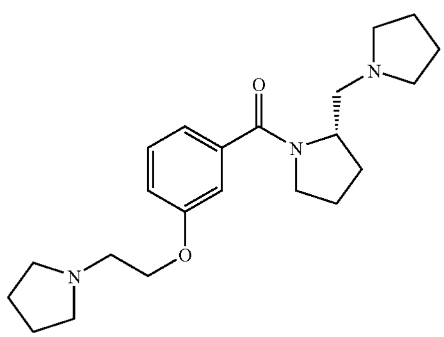 | 372 |
| 236 | 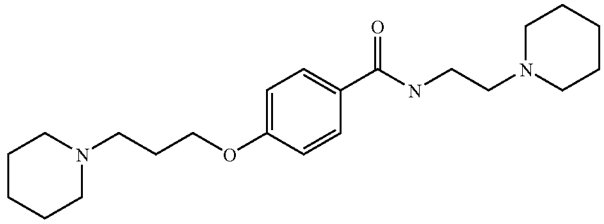 | 374.3 |

-continued

| Example Number | Structure | Observed Mass |
|---|---|---|
| 237 | 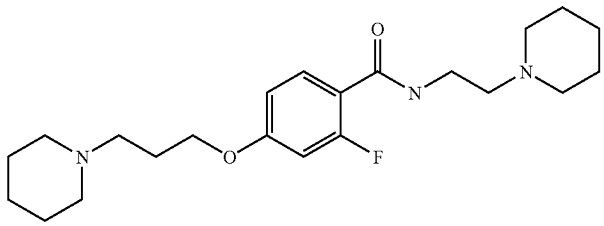 | 329.2 |
| 238 | 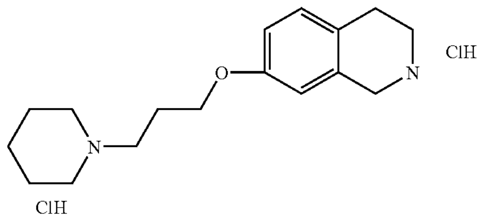 | 275.3 |
| 239 | 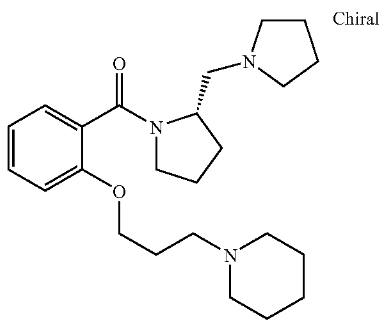 | 400 |
| 240 | 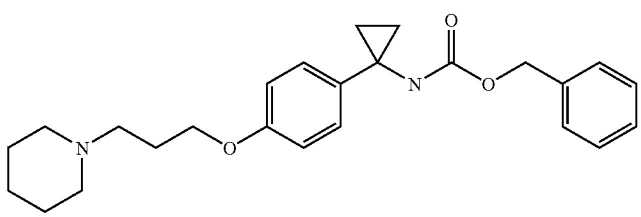 | 409.3 |
| 241 | 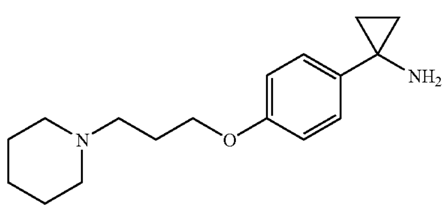 | 275.2 |
| 242 | 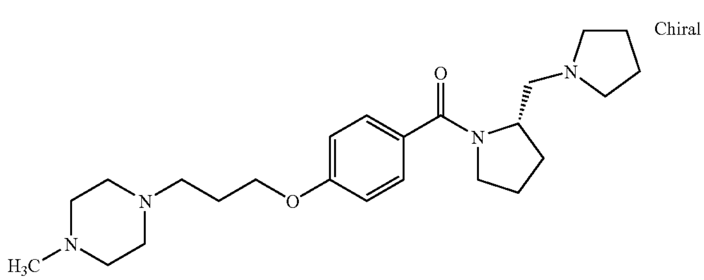 | 401 |

| Example Number | Structure | Observed Mass |
|---|---|---|
| 243 | 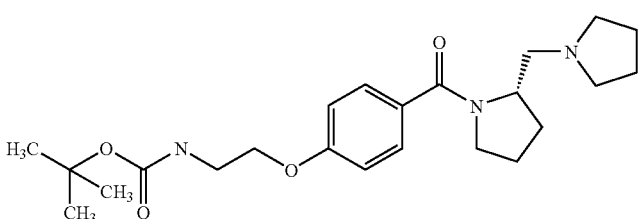 Chiral | 418 |
| 244 | 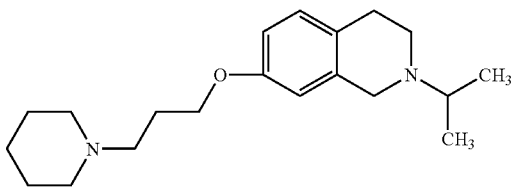 | 317.2 |
| 245 | 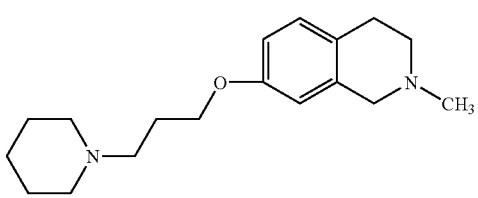 | 289.1 |
| 246 | 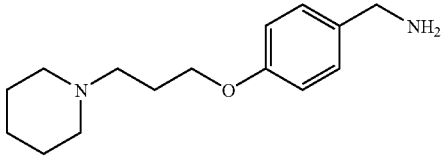 | |
| 247 | 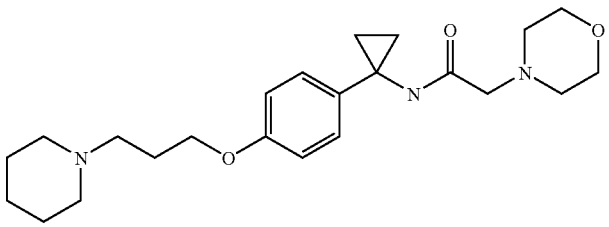 | 402.3 |
| 248 | 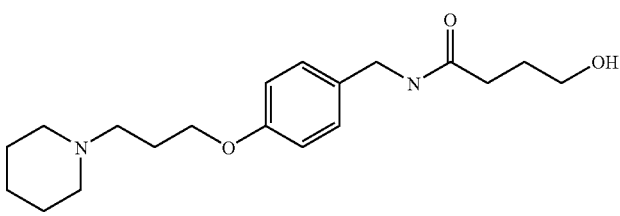 | |
| 249 | 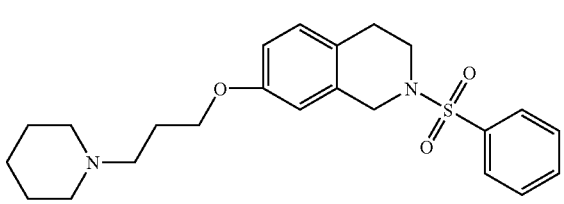 | 415.1 |

| Example Number | Structure | Observed Mass |
|---|---|---|
| 250 | 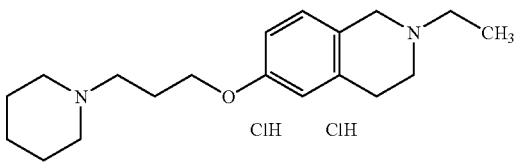 | 303.3 |
| 251 | 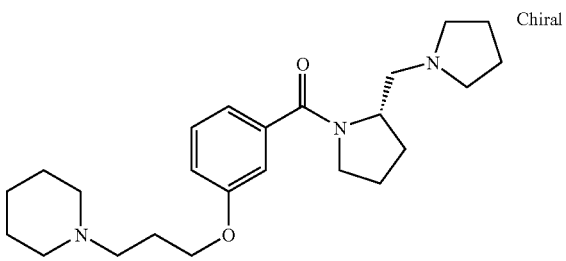 Chiral | 400 |
| 252 | 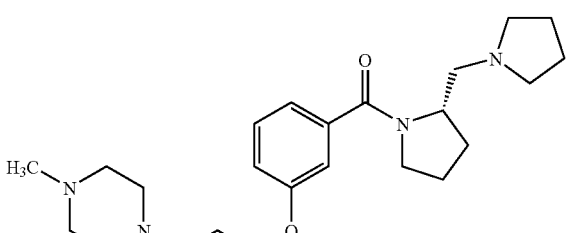 Chiral | 415 |
| 253 | 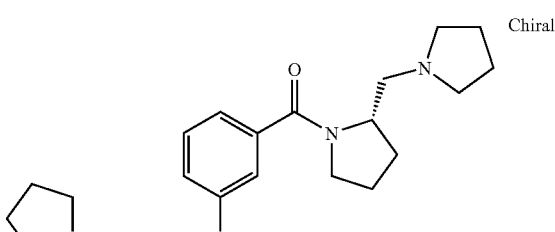 Chiral | 386 |
| 254 | 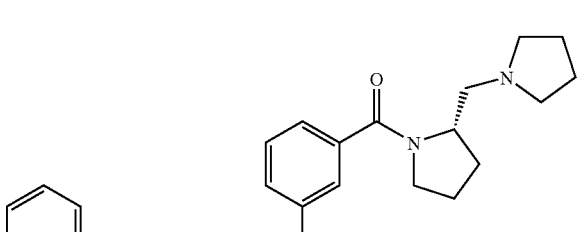 Chiral | 422 |
| 255 | 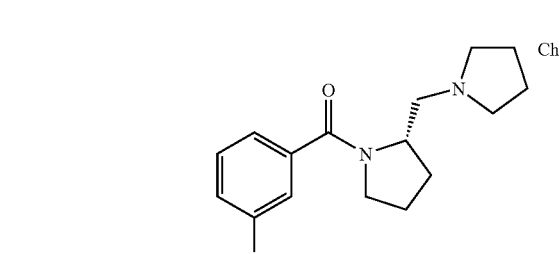 Chiral | 388 |

-continued
| Example Number | Structure | Observed Mass |
|---|---|---|
| 256 | 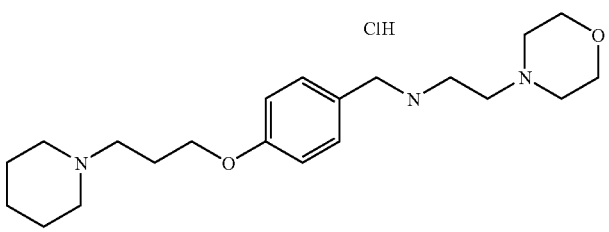 | 362.2 |
| 257 | 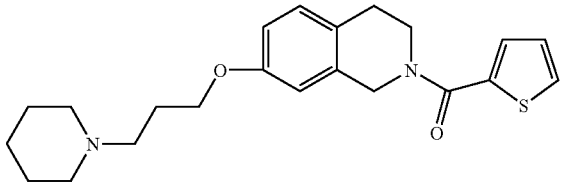 | 385.1 |
| 258 | 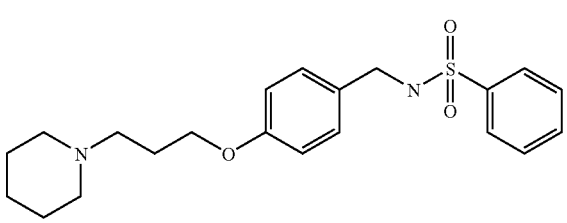 | |
| 259 | 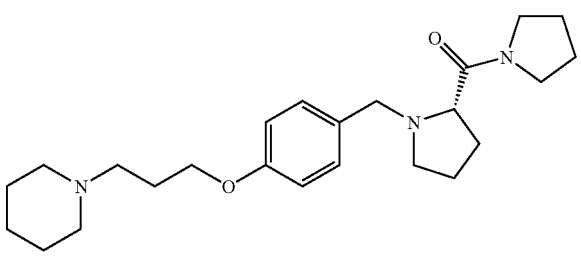 | 400 |
| 260 | 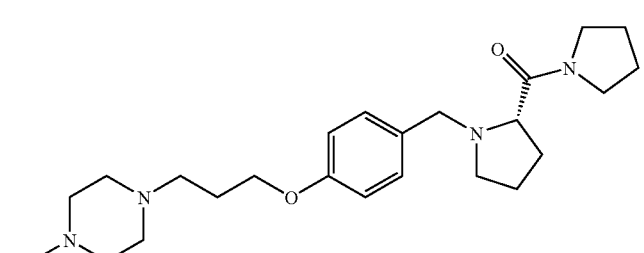 | 415 |
| 261 | 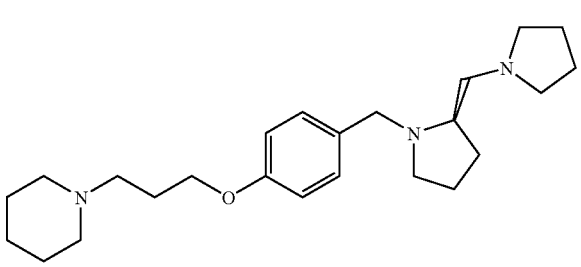 | 386 |

-continued
| Example Number | Structure | Observed Mass |
|---|---|---|
| 262 | 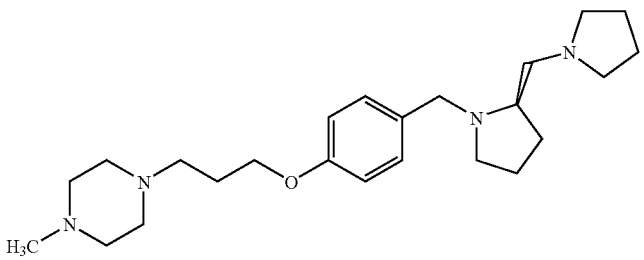 | 401 |
| 263 | 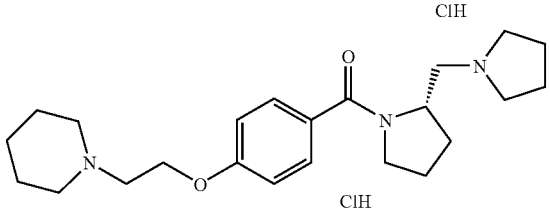 | 386 |
| 264 | 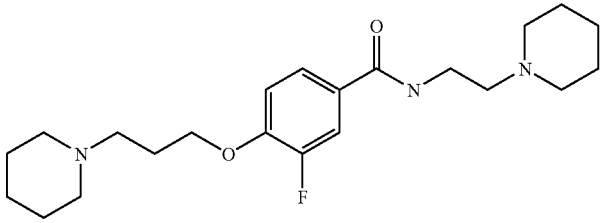 | 392.2 |
| 265 | 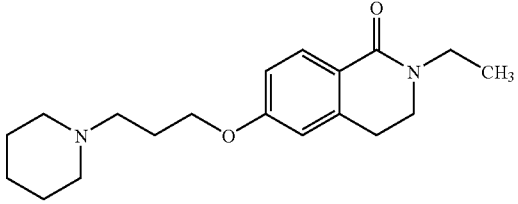 | 317.1 |
| 266 | 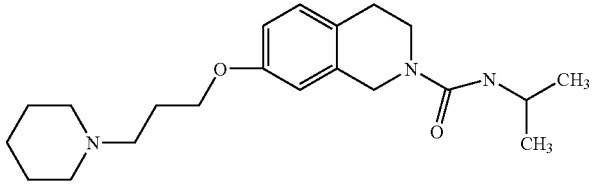 | 360.2 |
| 267 | 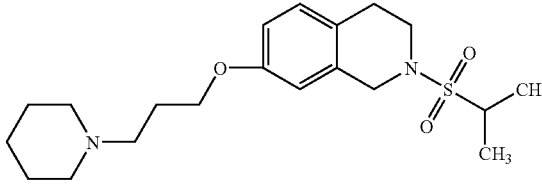 | 381.1 |
| 268 | 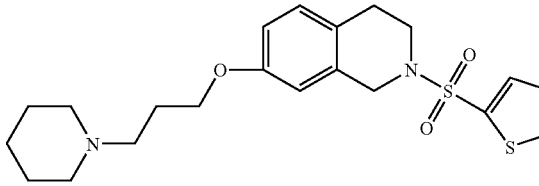 | 421.1 |

-continued
| Example Number | Structure | Observed Mass |
|---|---|---|
| 269 | 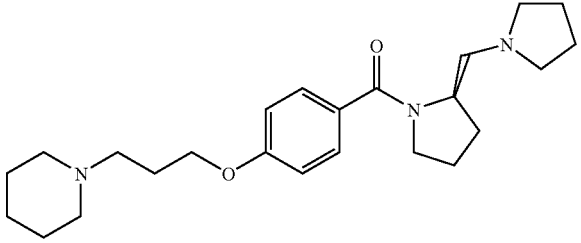 | 400 |
| 270 | 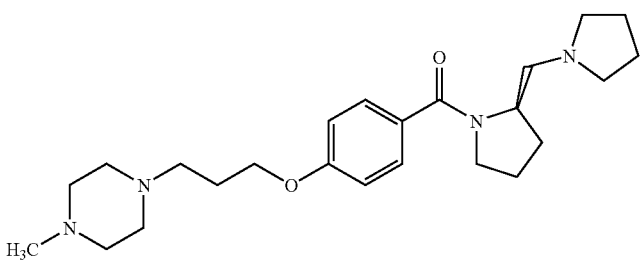 | 415 |
| 271 | 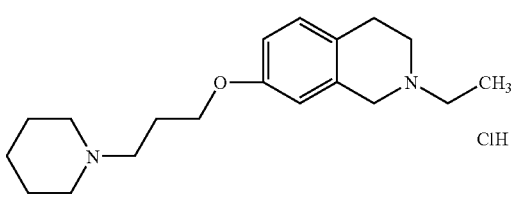 | 303.3 |
| 272 | 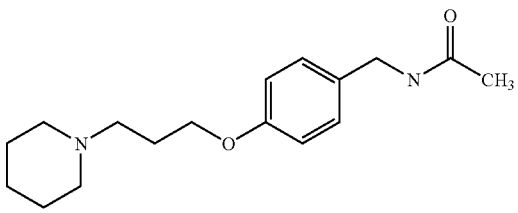 | — |
| 273 | 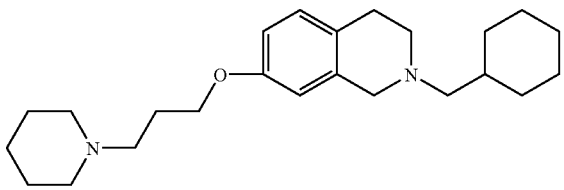 | 371.4 |
| 274 | 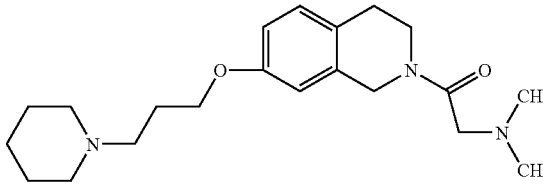 | 360.5 |
| 275 | 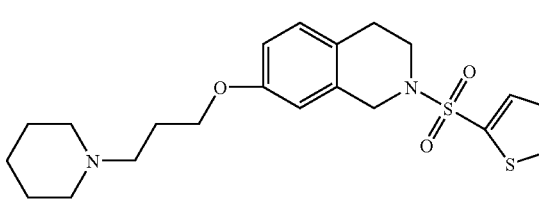 | 317.1 |

-continued
| Example Number | Structure | Observed Mass |
|---|---|---|
| 276 | 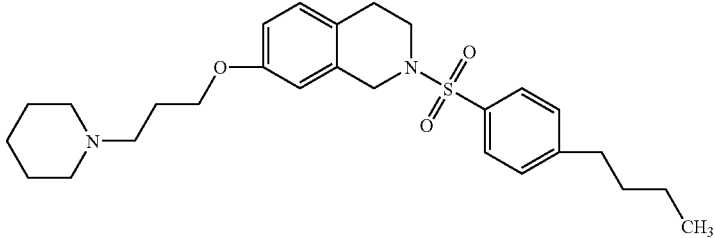 | 471.1 |
| 277 | 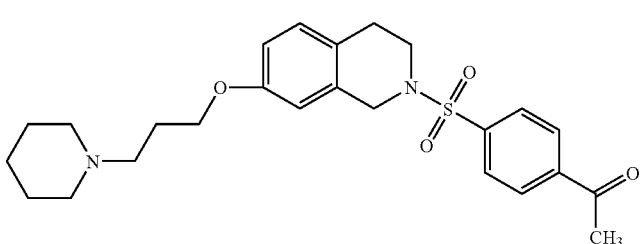 | 457.1 |
| 278 | 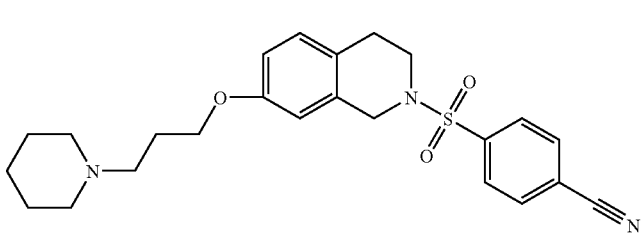 | 440.1 |
| 279 | 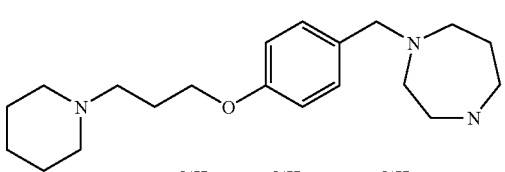 | |
| 280 | 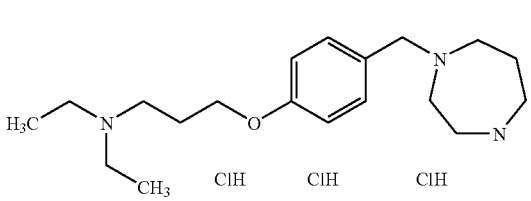 | |
| 281 | 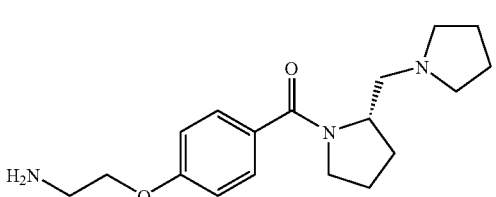 | 318 |
| 282 | 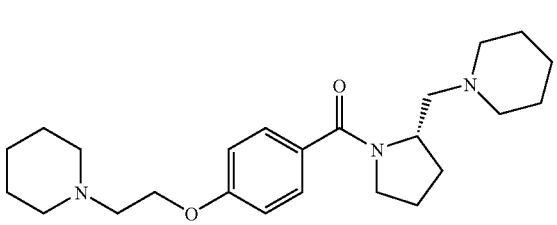 | 400 |

-continued
| Example Number | Structure | Observed Mass |
|---|---|---|
| 283 | 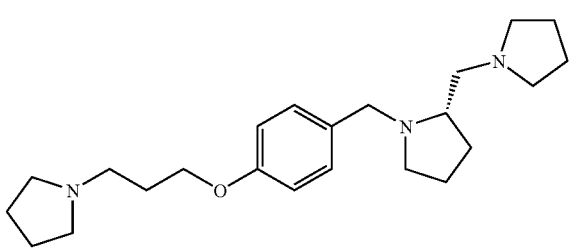 | 372 |
| 284 | 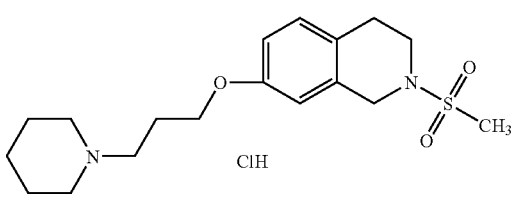 | 353.2 |
| 285 | 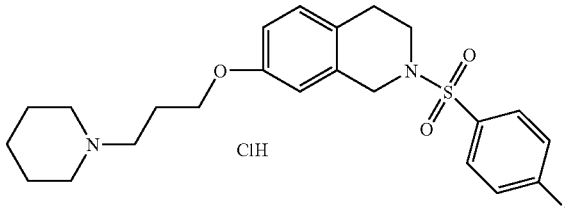 | 433.2 |
| 286 | 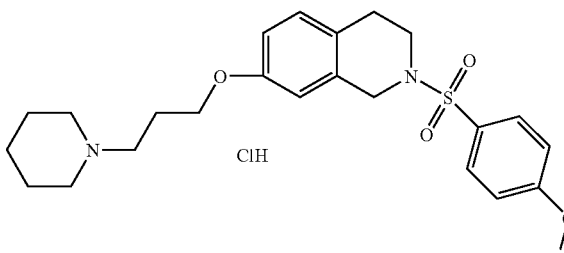 | 445.2 |
| 287 | 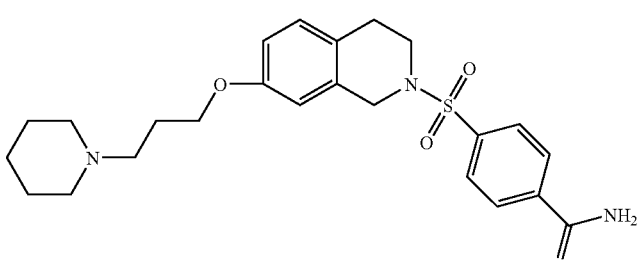 | 458.2 |
| 288 | 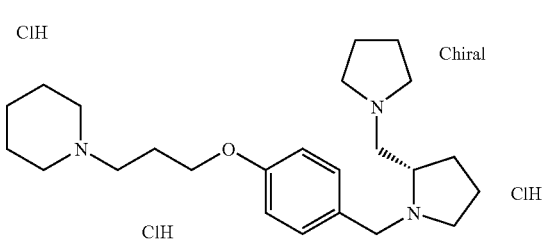 | 386 |

| Example Number | Structure | Observed Mass |
|---|---|---|
| 289 | 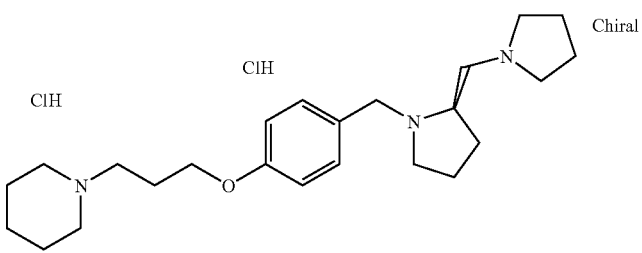 | 386 |
| 290 | 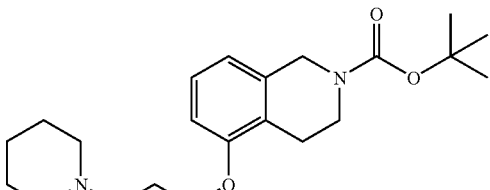 | 375.3 |
| 291 | 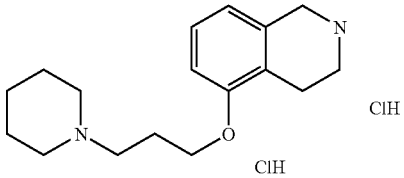 | 275.2 |
| 292 | 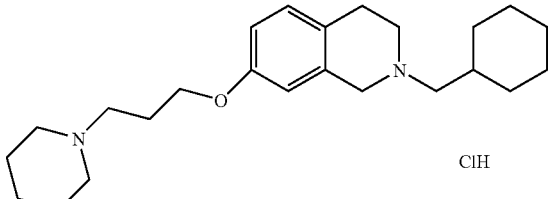 | 371.4 |
| 293 | 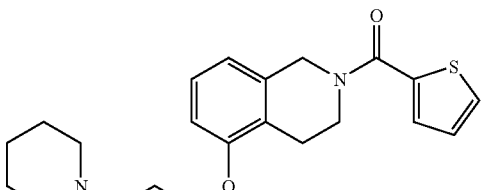 | 415.2 |
| 294 | 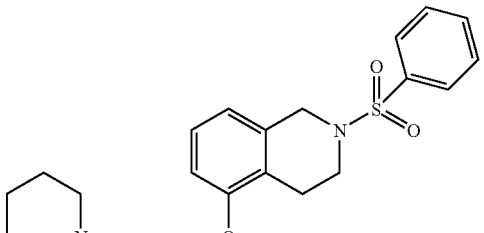 | 385.2 |

-continued

| Example Number | Structure | Observed Mass |
|---|---|---|
| 295 | 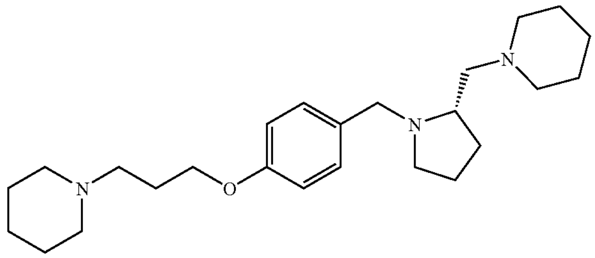 | 400 |
| 296 | 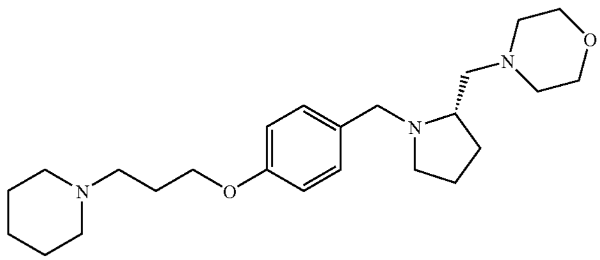 | 402 |
| 297 | 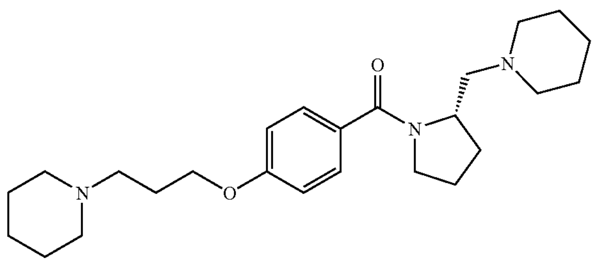 | 414 |
| 298 | 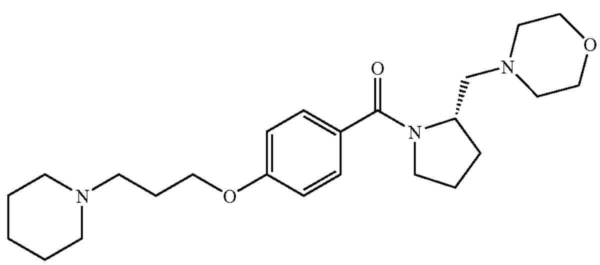 | 416 |
| 299 | 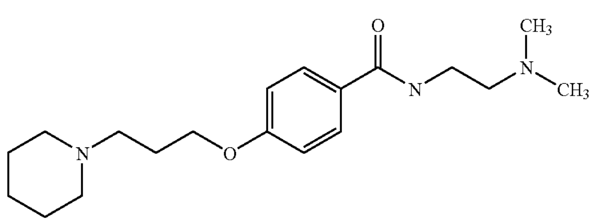 | 334 |
| 300 | 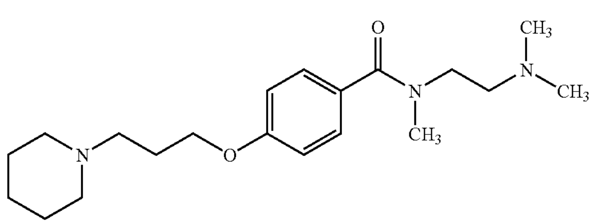 | 348 |

-continued
| Example Number | Structure | Observed Mass |
|---|---|---|
| 301 | 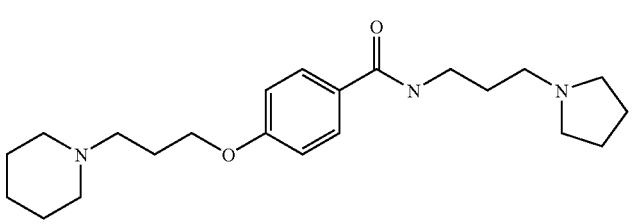 | 374 |
| 302 | 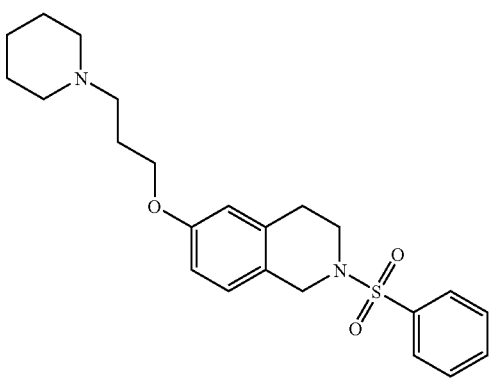 | 415.3 |
| 303 | 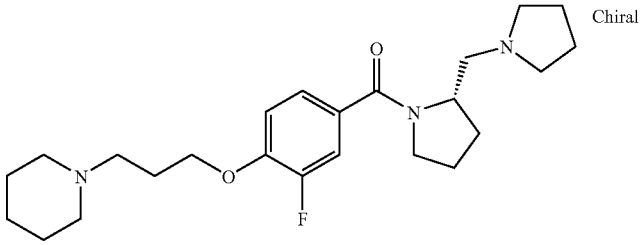 Chiral | 418.4 |
| 304 | 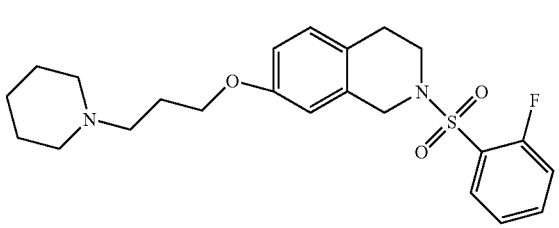 | 433.2 |
| 305 | 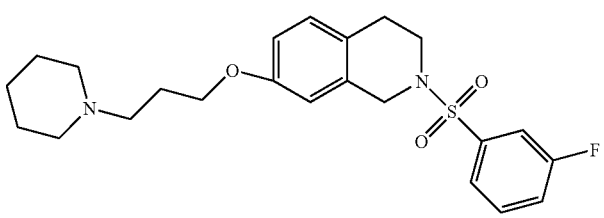 | 433.2 |
| 306 | 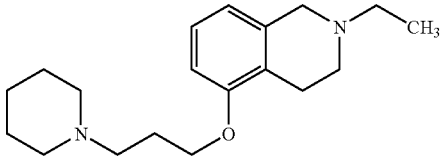 | 303.3 |

-continued
| Example Number | Structure | Observed Mass |
|---|---|---|
| 307 | 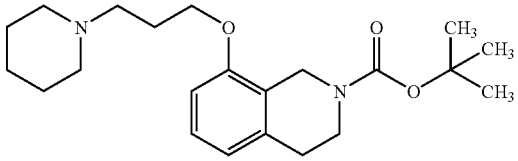 | 375.3 |
| 308 | 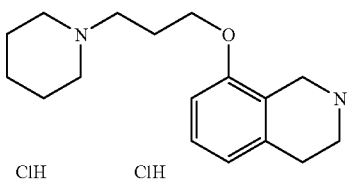 | 275.3 |
| 309 | 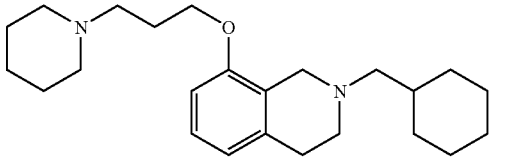 | 371.4 |
| 310 | 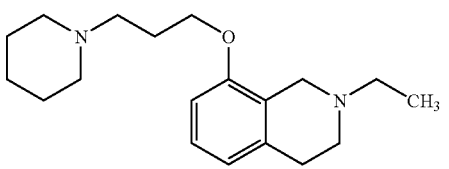 | 303.3 |
| 311 | 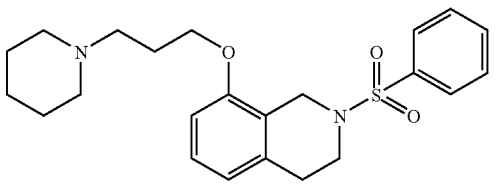 | 415.3 |
| 312 | 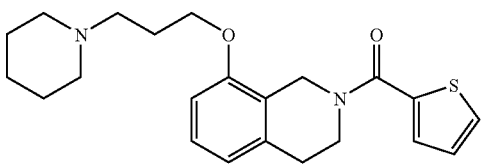 | 385.3 |
| 313 | 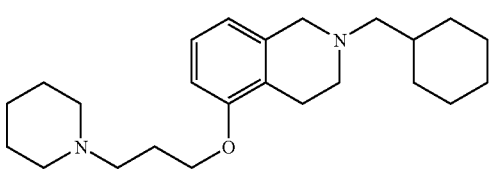 | 371.4 |
| 314 | 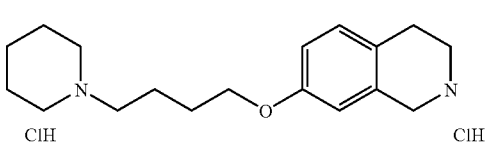 | 389.3 |
| 315 | 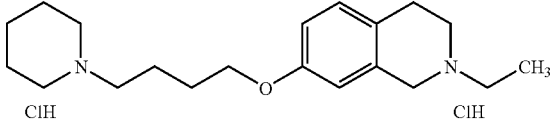 | 317.2 |

-continued

| Example Number | Structure | Observed Mass |
|---|---|---|
| 316 | 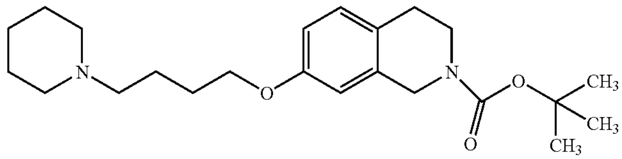 | 389.3 |
| 317 | 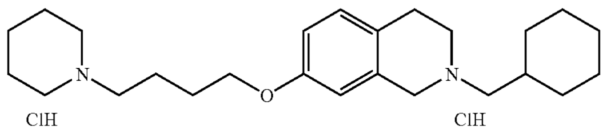 | 385.3 |
| 318 | 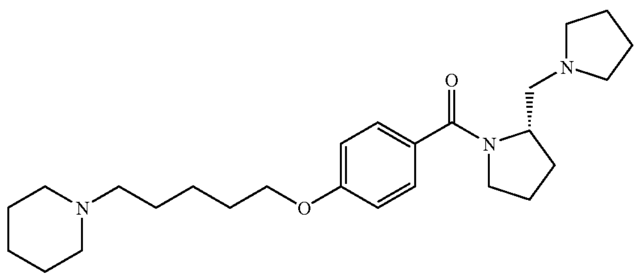 | 428 |
| 319 | 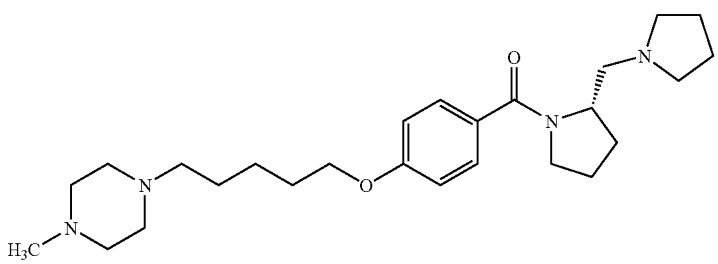 | 443 |
| 320 | 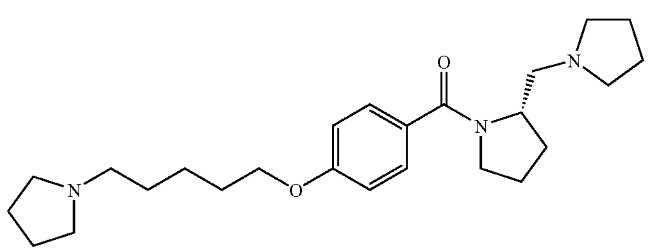 | 414 |
| 321 | 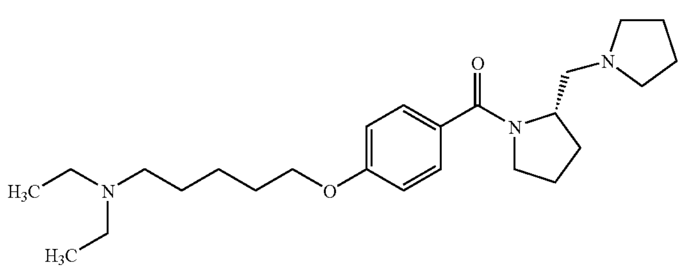 | 416 |

-continued

| Example Number | Structure | Observed Mass |
|---|---|---|
| 322 | 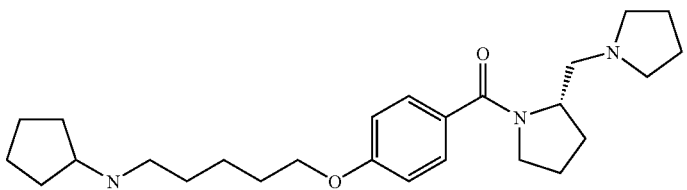 | 428 |
| 323 | 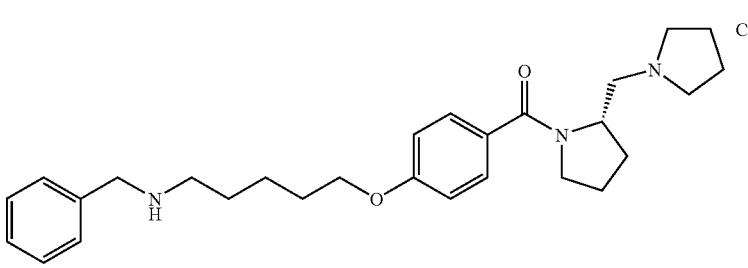 | 450 |
| 324 | 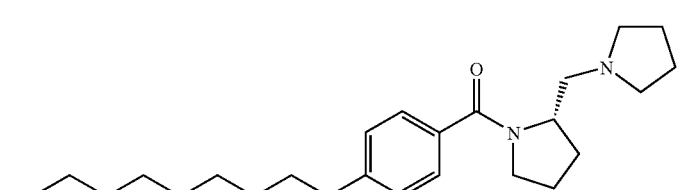 | 388 |

The compound of Formula I is preferably formulated in a unit dosage form prior to administration. Therefore, yet another embodiment of the present invention is a pharmaceutical composition comprising a compound of Formula I and one or more pharmaceutically acceptable carriers, diluents or excipients.

The present pharmaceutical compositions are prepared by known procedures using well-known and readily available ingredients. In making the formulations of the present invention, the active ingredient (Formula I compound) will usually be mixed with a carrier, or diluted by a carrier, or enclosed within a carrier which may be in the form of a capsule, sachet, paper or other container. When the carrier serves as a diluent, it may be a solid, semisolid or liquid material that acts as a vehicle, excipient, or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions of the present invention may be formulated in sustained release form to provide the rate controlled release of any one or more of the components or active ingredients to optimize the therapeutic effects, i.e., antihistaminic activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration, Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as a re conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 0.01 milligrams to about 1,000 milligrams, preferably from about 0.01 to about 950 milligrams, more preferably from about 0.01 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art. Generally, the human oral dosage form containing the active ingredients can be administered 1 or 2 times per day.

Utility

Compounds of Formula I are effective as histamine H3 receptor antagonists. More particularly, these compounds are selective histamine H3 receptor antagonists that have little or no affinity for histamine receptor GPRv53(H4R). As selective antagonists, the compounds of Formula I are useful in the treatment of diseases, disorders, or conditions responsive to the inactivation of the histamine H3 receptor, including but not limited to obesity and other eating-related disorders. It is postulated that selective antagonists of H3R will raise brain histamine levels and possibly that of other monoamines resulting in inhibition of food consumption while minimizing peripheral consequences. Although a number of H3R antagonists are known in the art, none have proven to be satisfactory obesity drugs. There is increasing evidence that histamine plays an important role in energy homeostasis. Histamine, acting as a neurotransmitter in the hypothalamus, suppressed appetite. Histamine is an almost ubiquitous amine found in many cell types and it binds to a family of G protein-coupled receptors (GPCRs). This family provides a mechanism by which histamine can elicit distinct cellular responses based on receptor distribution. Both the H1R and H2R are widely distributed. H3R is primarily expressed in the brain, notably in the thalamus and caudate nucleus. High density of expression of H3R was found in feeding center of the brain. A novel histamine receptor GPRv53 has been recently identified. GPRv53 is found in high levels in peripheral white blood cells; only low levels have been identified in the brain by some investigators while others cannot detect it in the brain. However, any drug discovery effort initiated around H3R must consider GPRv53 as well as the other subtypes.

The inventive compounds can readily be evaluated by using a competitive inhibition Scintillation Proximity Assay (SPA) based on a H3R binding assay using [3H] a methylhistamine as ligand. Stable cell lines, including but not limited to HEK can be transfected with cDNA coding for H3R to prepare membranes used for the binding assay. The technique is illustrated below (Example 3) for the histamine receptor subtypes.

Membranes isolated as described in Example 3 were used in a [$^{35}$S]GTP$\chi$S functional assay. Binding of [$^{35}$S]GTP$\chi$S to membranes indicates agonist activity. Compounds of the invention of Formula I were tested for their ability to inhibit binding in the presence of agonists. Alternately, the same transfected cell lines were used for a cAMP assay wherein H3R agonists inhibited forskolin-activated synthesis of cAMP. Compounds of Formula I were tested for their ability to permit forskolin-stimulated cAMP synthesis in the presence of agonist.

Preparation of Histamine Receptor Subtype Membranes

A. Preparation H1R Membranes cDNA for the human histamine 1 receptor (H1R) was cloned into a mammalian expression vector containing the CMV promoter (pcDNA3.1 (+), Invitogen) and transfected into HEK293 cells using the FuGENE Tranfection Reagent (Roche Diagnostics Corporation). Transfected cells were selected using G418 (500 µ/ml). Colonies that survived selection were grown and tested for histamine binding to cells grown in 96-well dishes using a scintillation proximity assay (SPA) based radioligand binding assay. Briefly, cells, representing individual selected clones, were grown as confluent monolayers in 96-well dishes (Costar Clear Bottom Plates, #3632) by seeding wells with 25,000 cells and growing for 48 hours (37° C., 5% $CO_2$). Growth media was removed and wells were rinsed two times with PBS (minus $Ca^{2+}$ or $Mg^{2+}$). For total binding, cells were assayed in a SPA reaction containing 50 mM Tris-HCL (assay buffer), pH 7.6, 1 mg wheat germ agglutinin SPA beads (Amersham Pharmacia Biotech, #RPNQ0001), and 0.8 nM $^3$H-pyrilamine (Net-594, NEN) (total volume per well=200 µl). Astemizole (10 µM, Sigma #A6424) was added to appropriate wells to determine non-specific binding. Plates were covered with FasCal and incubated at room temperature for 120 minutes. Following incubation, plates were centrifuged at 1,000 rpm (~800 g) for 10 minutes at room temperature. Plates were counted in a Wallac Trilux 1450 Microbeta scintillation counter. Several clones were selected as positive for binding, and a single clone (H1R40) was used to prepare membranes for binding studies. Cell pellets, representing ~10 grams, were resuspended in 30 ml assay buffer, mixed by vortexing, and centrifuged (40,000 g at 4° C.) for 10 minutes. The pellet resuspension, vortexing, and centrifugation was repeated 2 more times. The final cell pellet was reusupened in 30 ml and homogenized with a Polytron Tissue Homogenizer. Protein determinations were done using the Coomassie Plus Protein Assay Reagent (Pierce). Five micrograms of protein was used per well in the SPA receptor-binding assay.

B. Preparation H2R Membranes cDNA for the human histamine 2 receptor was cloned, expressed and transfected into HEK 293 cells as described above. Histamine binding to cells was assayed by SPA described above. For total binding, cells were assayed in a SPA reaction containing 50 mM Tris-HCl (assay buffer), pH 7.6, 1 mg wheat germ agglutinin SPA beads (Amersham Pharmacia Biotech, #RPNQ0001), and 6.2 nM $^3$H-tiotidine (Net-688, NEN) (total volume per well=200 µl). Cimetidine (10 µM, Sigma #C4522) was added to appropriate wells to determine non-specific binding.

Several clones were selected as positive for binding, and a single clone (H2R10) was used to prepare membranes for binding studies. Five micrograms of protein was used per well in the SPA receptor-binding assay.

C. Preparation of H3R Membranes cDNA for the human histamine 3 receptor was cloned and expressed as described in Example 1, above. Transfected cells were selected using G418 (500 µ/ml), grown, and tested for histamine binding by the SPA described above. For total binding, cells were assayed in a SPA reaction described above containing 50 mM Tris-HCL (assay buffer), pH 7.6, 1 mg wheat germ agglutinin SPA beads (Amersham Pharmacia Biotech, #RPNQ0001), and 1 nM ($^3$H)-n-alpha-methylhistamine (NEN, NET1027) (total volume per well=200 µl). Thioperimide was added to determine non-specific binding. Several clones were selected as positive for binding, and a single clone (H3R8) was used to prepare membranes for binding studies described above. Five micrograms of protein was used per well in the SPA receptor-binding assay.

All compounds set forth in examples 1 to 322 exhibited affinity for the H3 receptor greater than 1 uM. Preferred compounds of the invention exhibited affinity for the H3 receptor greater than 200 nM. Most preferred compounds of the invention exhibit affinity for the H3 receptor greater than 20 nM.

D. Preparation of GPRv53 Membranes cDNA for the human GPRv53 receptor was cloned and expressed as described in Example 1, above. Transfected cells were selected, tested for histamine binding, and selected. HEK293 GPRv53 50 cells were grown to confluency in DMEM/F12 (Gibco) supplemented with 5% FBS and 500 ug/ml G418 and washed with Delbecco's PBS (Gibco) and harvested by scraping. Whole cells were homogenized with a Polytron tissuemizer in binding buffer, 50 mM Tris pH 7.5. Cell lysates, 50 ug, were incubated in 96 well dishes with 3 nM (3H) Histamine and compounds in binding buffer for 2 hours at room temperature. Lysates were filtered through glass fiber filters (Perkin Elmer) with a Tomtec cell harverster. Filters were counted with melt-on scintillator sheets (Perkin Elmer) in a Wallac Trilux 1450 Microbeta Scintillation counter for 5 minutes.

Pharmacological Results cAMP ELISA

HEK293H3R8 cells prepared as described above were seeded at a density of 50,000 cells/well and grown overnight in DMEM/F12 (Gibco) supplemented with 5% FBS and 500 ug/ml G418. The next day tissue culture medium was removed and replaced with 50 µl cell culture medium containing 4 mM 3-isobutyl-1-methylxanthine (Sigma) and incubated for 20 minutes at room temperature. Antagonist were added in 50 µl cell culture medium and incubated for 20 minutes at room temperature. Agonist R(-)α methylhistamine (RBI) at a dose response from $1\times10^{-10}$ to $1\times10^{-5}$ M was then added to the wells in 50 µl cell culture medium and incubated for 5 minutes at room temperature. Then 50 µl of cell culture medium containing 20 µM Forskolin (Sigma) was added to each well and incubated for 20 minutes at room temperature. Tissue culture medium was removed and cells were lysed in 0.1M HCl and cAMP was measured by ELISA (Assay Designs, Inc.).

[35S] GTP γ [S] Binding Assay

Antagonist activity of selected compounds was tested for inhibition of [$^{35}$S] GTP γ [S] binding to H3R membranes in the presence of agonists. Assays were run at room temperature in 20 mM HEPES, 100 mM NaCl, 5 mM MgCl$_2$ and 10 uM GDP at pH 7.4 in a final volume of 200 ul in 96-well Costar plates. Membranes isolated from H3R8-expressing HEK293 cell line (20 ug/well) and GDP were added to each well in a volume of 50 µl assay buffer. Antagonist was then added to the wells in a volume of 50 µl assay buffer and incubated for 15 minutes at room temperature. Agonist R(-) alpha methylhistamine (RBI) at either a dose response from $1\times10^{-10}$ to $1\times10^{-5}$ M or fixed concentration of 100 nM were then added to the wells in a volume of 50 µl assay buffer and incubated for 5 minutes at room temperature. GTP γ [$^{35}$S] was added to each well in a volume of 50 µl assay buffer at a final concentration of 200 pM, followed by the addition of 50 µl of 20 mg/ml WGA coated SPA beads (Amersham). Plates were counted in Wallac Trilux 1450 Microbeta scintillation counter for 1 minute. Compounds that inhibited more than 50% of the specific binding of radioactive ligand to the receptor were serially diluted to determine a K[i](nM). The results are given below the indicated compound.

TABLE 1

| Compound | Ki (nM) | Structure |
|---|---|---|
| Example 2 | 1.48, 0.95 | (structure) |
| Example 1 | 1.4 | (structure) |

To investigate the selectivity of the antagonists for the histamine receptors, a competitive binding assay described above was performed. The ability of example 131 and 250 (structures given above) to selectively inhibit binding to H3R, H1R, H2 and H4R was determined. Importantly, the identification of H3R-specific antagonists that do bind the newly identified H4R was demonstrated. Until the present invention, most known H3R antagonists also bound H4R. As demonstrated in Table 2, example 131 and example 250 did not inhibit binding H4R compare to H3R. To our knowledge, the study in Table 2 is the first demonstration of a H3R specific antagonist.

TABLE 2

| Compound | Ki (nM) | | | |
| --- | --- | --- | --- | --- |
| | H3R | H4R | H1R | H2 |
| Example 131 | 1.05 | ≧20,000 | ≧20,000 | ≧20,000 |
| Example 250 | 0.37 | ≧20,000 | 1022 | 1109 |

Non-imidazole containing histamine H3 receptor antagonists disclosed in the literature generally have very poor pharmacokinetic properties (see J. Apelt, et al, J. Med. Chem. 2002,45,1128-1141). Compounds of this invention have markedly and unexpectedly improved pharmacokinetic properties. Male Sprague Dawley Rats (n=3 per dose arm) were separately dosed with 3 mg/kg iv or 10 mg/kg po of compound examples 131 and 271 (vehicle: 5% ethanol/water or water respectively; dose volume: 1 mL/kg iv, 10 mL/kg po). Approximately 0.5 mL of blood was collected in heparin collection tubes at multiple time points over an 8 or 24-hour period for examples 131 and 271 respectively, and the samples were analyzed using LC/MS/MS. In this manner compound example 131 was found to have an oral bioavailability of 58% (AUC 0-24 hr; po/iv ratio) and an oral half-life of 10.4±4.2 hours (±SEM). Compound example 271 was found to have an oral bioavailability of 69% (AUC0-24 hr; po/iv ratio) and an oral half-life of 71.9±3.3 hours (±SEM).

From the above description, one skilled in the art can ascertain the essential characteristics of the present invention, and without departing from the spirit and scope thereof, can make various changes and modifications of the invention to adapt it to various usages and conditions. Thus, other embodiments are also within the claims.

What is claimed is:

1. A compound structurally represented by Formula I

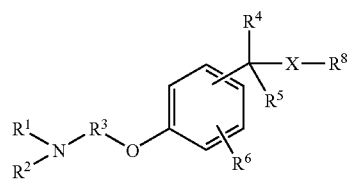

or pharmaceutically acceptable salts thereof wherein:
X is $NR^7$;
$R^1$ is hydrogen,
  $C_1$-$C_8$ alkyl optionally substituted with 1 to 4 halogens,
  $(CHR^5)_n$—$C_3$-$C_7$ cycloalkyl,
  $(CHR^5)_n$ aryl,
  $(CHR^5)_n$ heteroaryl, or
  $(CHR^5)_n$—O$(CHR^5)_n$-aryl;
$R^2$ is independently $R^1$, or $COR^1$, or cyclized with the attached nitrogen atom at the $R^1$ position to form a 4, 5, or 6 member carbon ring, wherein one of said carbons is optionally replaced by one of O, S, $NR^1$ or CO, or wherein the ring formed by $R^1$ and $R^2$ is optionally substituted one to two times with $C_1$-$C_4$ alkyl;
$R^3$ is independently $C_3$-$C_7$ cycloalkylene, or $C_1$-$C_5$ alkylene optionally substituted one or two times with $C_1$-$C_3$ alkyl;
$R^4$ is
  hydrogen, halogen, $C_1$-$C_4$ alkyl, $(CHR^5)_n$—$C_3$-$C_7$ cycloalkyl, $(CHR^5)_n$ aryl,
  $(CHR^5)_n$ heteroaryl, $(CHR^5)_n$—O$(CHR^5)_n$-aryl or CO or cyclized with $R^5$ to from a cyclopropyl ring;
$R^5$ is
  hydrogen, or $C_1$-$C_4$ alkyl;
$R^6$ is
  cyclized with the attached carbon atom at $R^7$ to form, including the fused benzene ring, a substituted tetrahydroisoquinoline ring;
$R^8$ is
  hydrogen, a bond, $C_1$-$C_8$ alkyl, —$SO_2$ $R^9$, —$CO_2$ $R^{10}$, —CO $R^9$, —CONH $R^{10}$;
$R^9$ is
  hydrogen, halogen, $C_1$-$C_8$ alkyl optionally substituted with 1 to 4 halogens, $C_3$-$C_7$ cycloalkyl, aryl, $CH_2$ aryl, heteroaryl, heterocycle, —O$(CHR^5)_n$-aryl, —$COR^1$, —$CONR^1$ $R^2$, —$SO_2R^1$, —$OR^1$, —$N(R^1)_2$, —$NR^1$ $R^2$, —$CH_2NR^1$ $R^2$, —$CONR^1$ $R^2$—$NHSO_2R^1$, —$NO_2$, —$CO_2R^1$, —$SO_2N(R^1)_2$, —$S(O)_nR^1$, —$OCF_3$, —$CH_2SR^5$;
$R^{10}$ is
  hydrogen, halogen, $C_1$-$C_8$ alkyl optionally substituted with 1 to 4 halogens, $C_3$-$C_7$ cycloalkyl, aryl, $CH_2$ aryl, heteroaryl, heterocycle, —$COR^1$, —$CONR^1R^2$, —$SO_2R^1$, —$N(R^1)_2$, —$NR^1$ $R^2$, —$CH_2NR^1$ $R^2$, —$CONR^1$ $R^2$—$CO_2R^1$, —$SO_2N(R^1)_2$, —$S(O)_nR^1$, —$CH_2SR^5$;
and n is 0-4:
provided the compound is not 1,2,3,4-tetrahydro-1-(4-hydroxyphenyl)-6-[2-(1-pyrrolidinyl)ethoxy]-2-(trifluoroacetyl)-isoquinoline, or 1,2,3,4-tetrahydro-5-[3-[4-(2-pyridinyl)-1-piperazinyl]propoxy]-isoquinoline.

2. The compound of claim 1 selected from the group consisting of:

| Example Number | Structure |
| --- | --- |
| 35 | 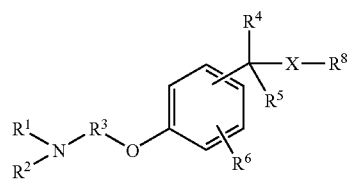 |

-continued

| Example Number | Structure |
|---|---|
| 40 | 6-[3-(dimethylamino)propoxy]-1,2,3,4-tetrahydroisoquinoline dihydrochloride (ClH · ClH salt) |
| 76 | 2-ethyl-6-[3-(dimethylamino)propoxy]-1,2,3,4-tetrahydroisoquinoline |
| 77 | 2-[3-(dimethylamino)propyl]-6-[3-(dimethylamino)propoxy]-1,2,3,4-tetrahydroisoquinoline |
| 78 | 6-[3-(dimethylamino)propoxy]-2-{[1-phenyl-5-(trifluoromethyl)-1H-pyrazol-4-yl]carbonyl}-1,2,3,4-tetrahydroisoquinoline |
| 79 | 6-[3-(dimethylamino)propoxy]-2-(methylsulfonyl)-1,2,3,4-tetrahydroisoquinoline |
| 80 | 2-{6-[3-(dimethylamino)propoxy]-3,4-dihydroisoquinolin-2(1H)-yl}acetamide |
| 81 | 6-[3-(dimethylamino)propoxy]-2-[2-(piperidin-1-yl)ethyl]-1,2,3,4-tetrahydroisoquinoline |
| 82 | 6-[3-(dimethylamino)propoxy]-2-(pyridin-3-ylmethyl)-1,2,3,4-tetrahydroisoquinoline |

-continued
| Example Number | Structure |
|---|---|
| 83 | 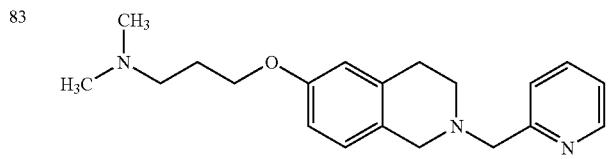 |
| 126 | 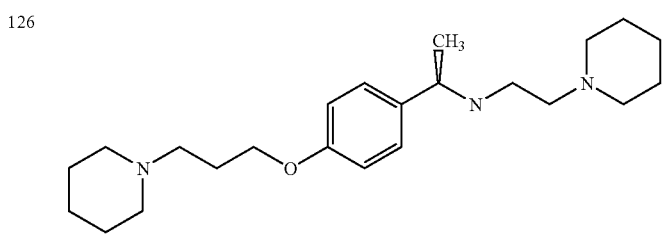 |
| 127 | 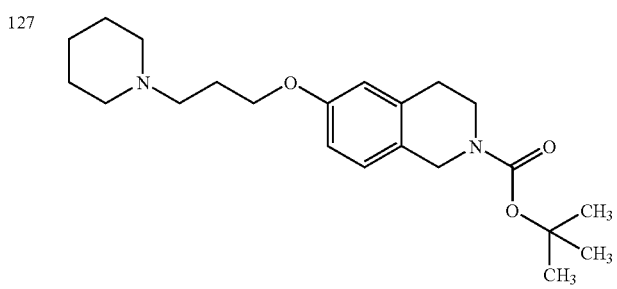 |
| 128 | 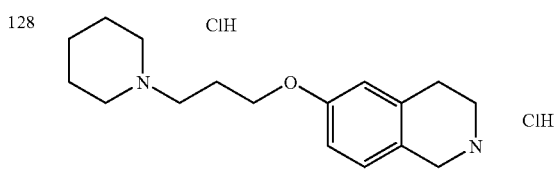 |
| 129 | 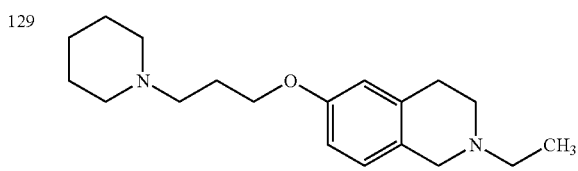 |
| 134 | 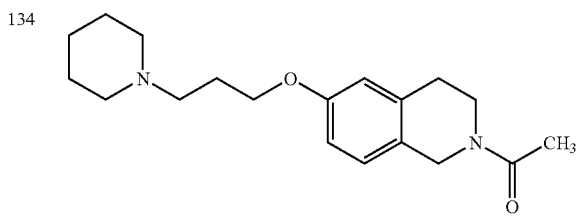 |
| 138 | 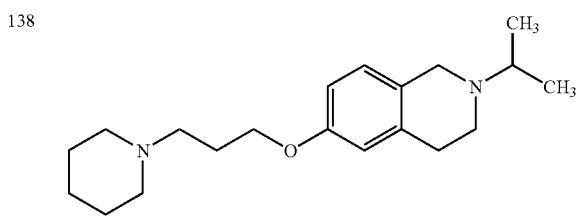 |

-continued
| Example Number | Structure |
|---|---|
| 139 | 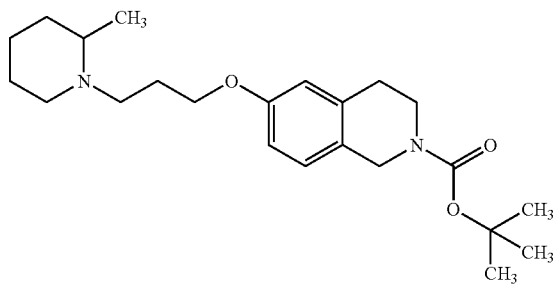 |
| 140 | 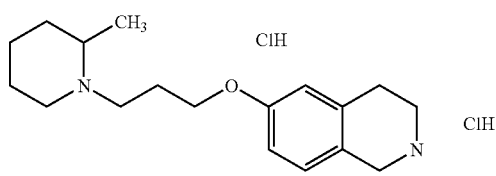 |
| 141 | 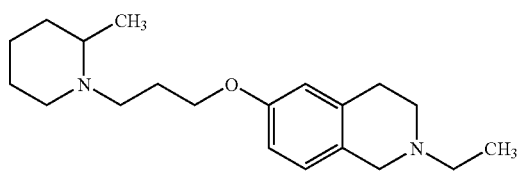 |
| 143 | 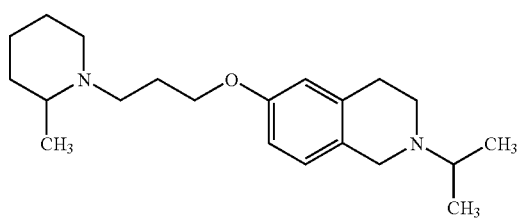 |
| 145 | 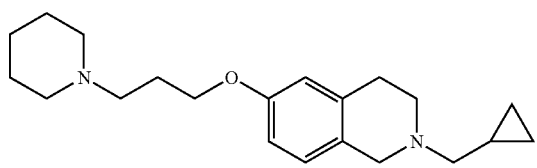 |
| 146 | 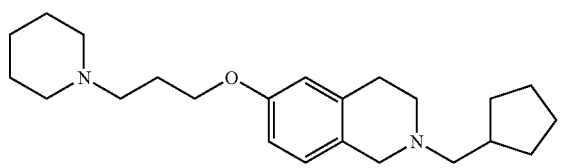 |
| 147 | 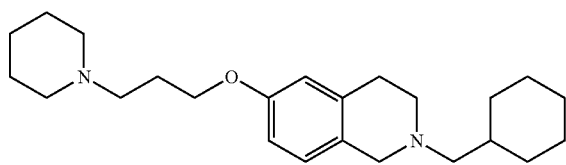 |
| 148 | 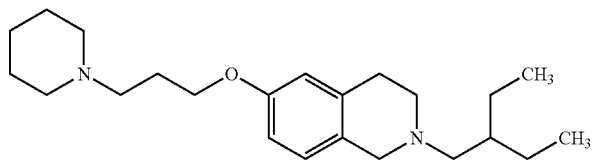 |

| Example Number | Structure |
|---|---|
| 149 | 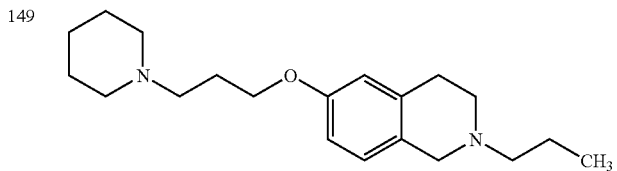 |
| 156 | 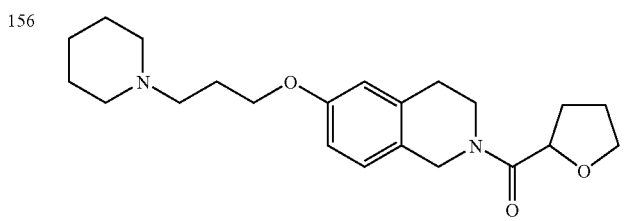 |
| 157 | 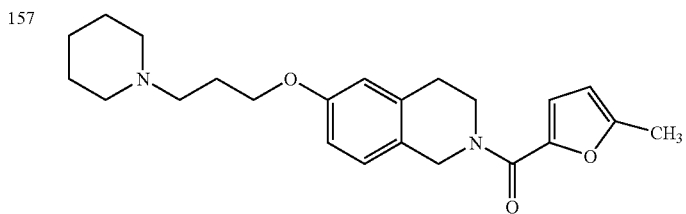 |
| 158 | 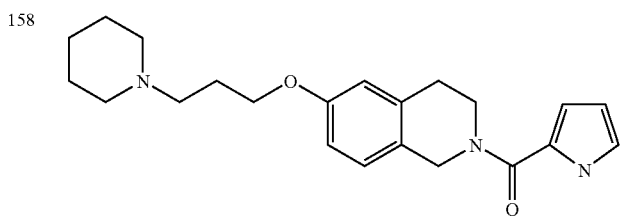 |
| 159 | 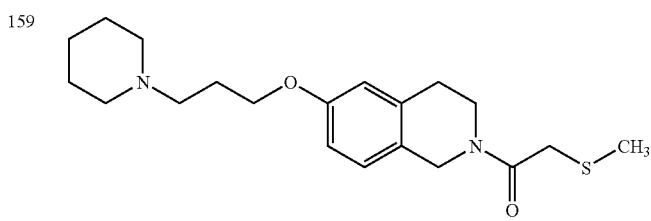 |
| 160 | 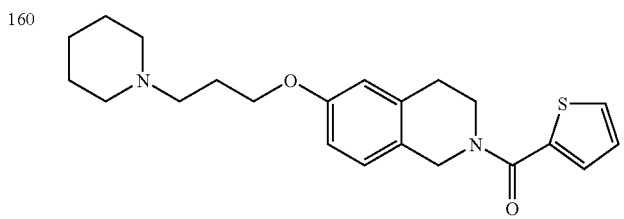 |
| 161 | 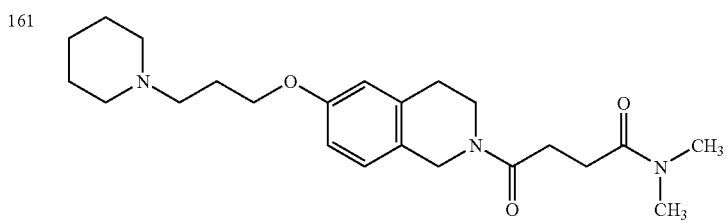 |

-continued
| Example Number | Structure |
|---|---|
| 162 | 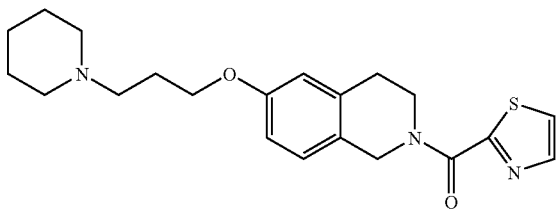 |
| 163 | 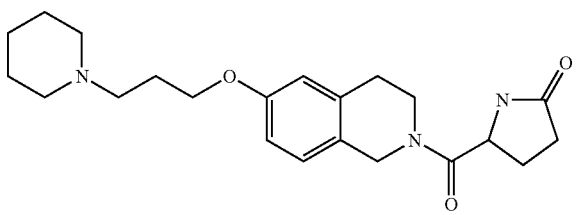 |
| 164 | 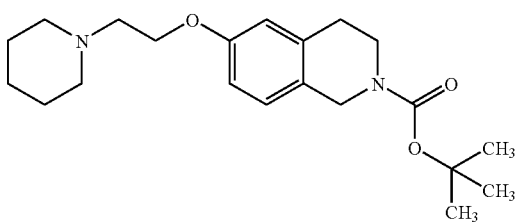 |
| 165 | 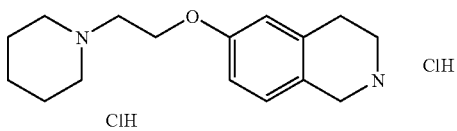 |
| 166 | 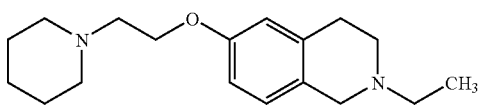 |
| 168 | 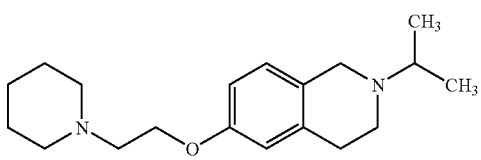 |
| 169 | 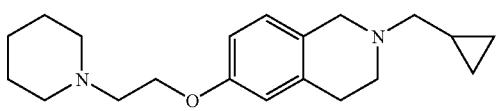 |
| 170 | 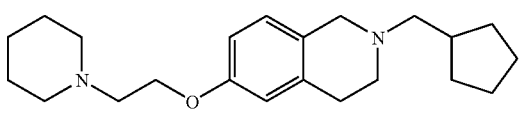 |
| 171 | 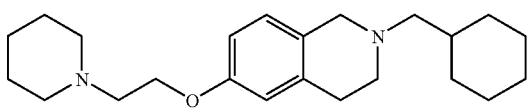 |

-continued
| Example Number | Structure |
|---|---|
| 172 | 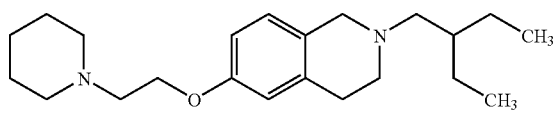 |
| 175 | 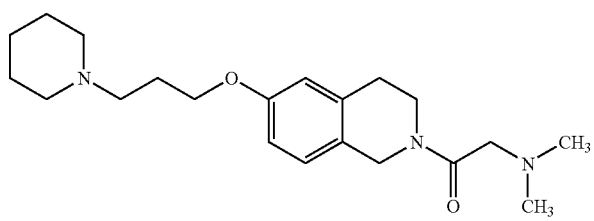 |
| 176 | 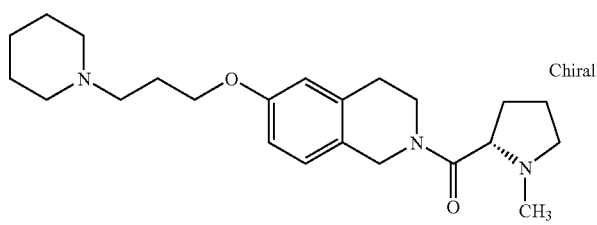 Chiral |
| 177 | 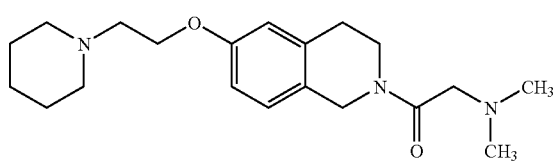 |
| 178 | 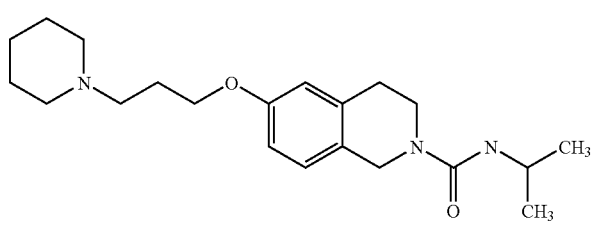 |
| 179 | 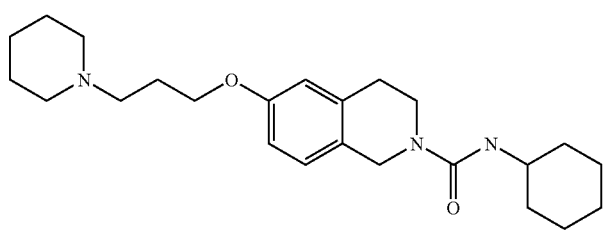 |
| 182 | 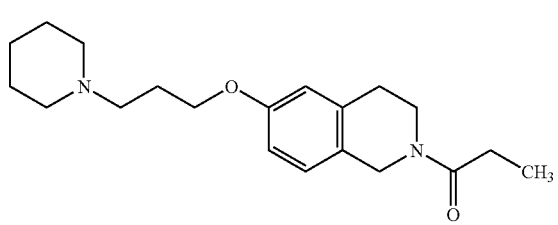 |

| Example Number | Structure |
|---|---|
| 183 | 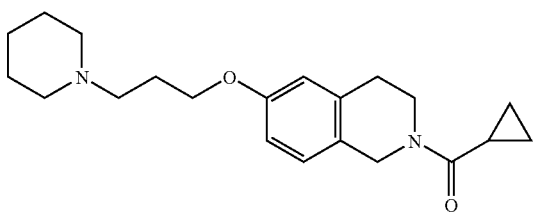 |
| 184 | 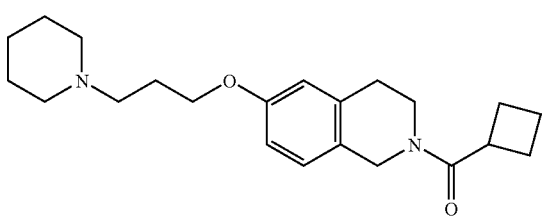 |
| 185 | 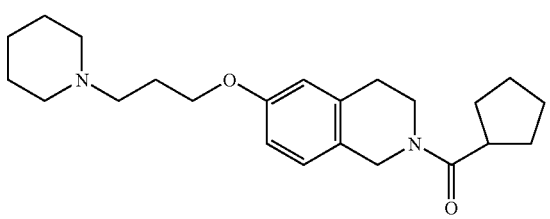 |
| 186 | 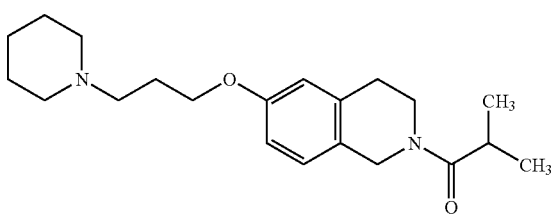 |
| 187 | 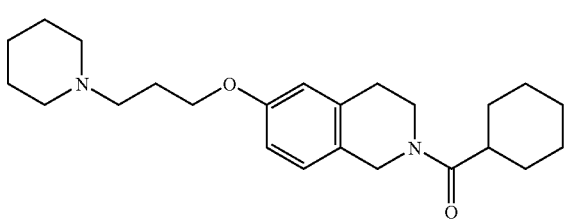 |
| 188 | 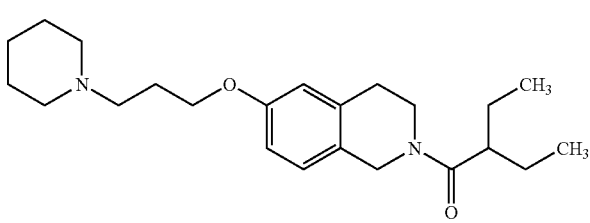 |
| 193 | 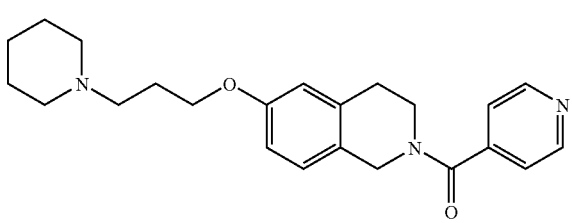 |

-continued
| Example Number | Structure |
|---|---|
| 194 | 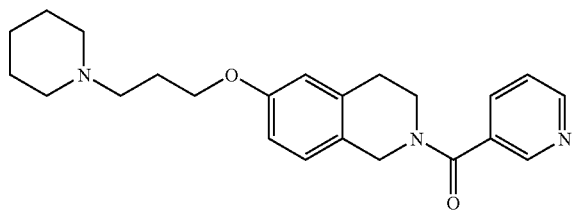 |
| 195 | 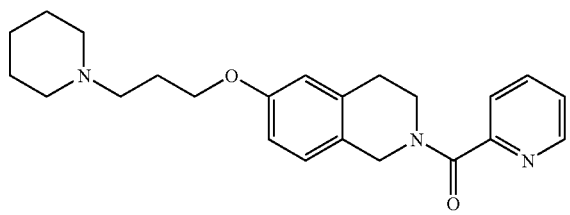 |
| 196 | 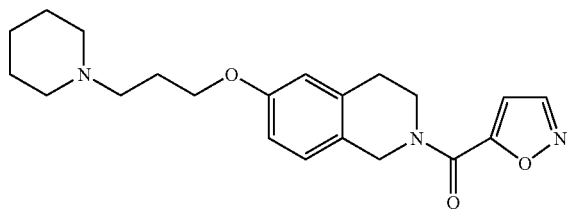 |
| 205 | 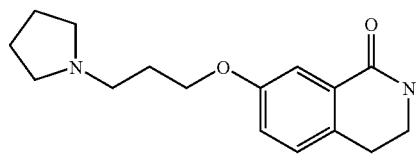 |
| 206 | 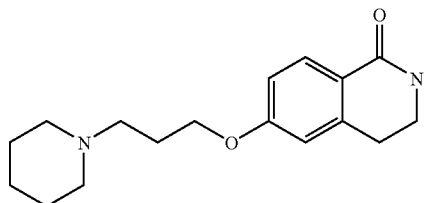 |
| 207 | 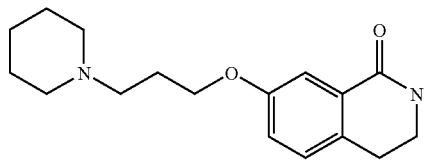 |
| 228 | 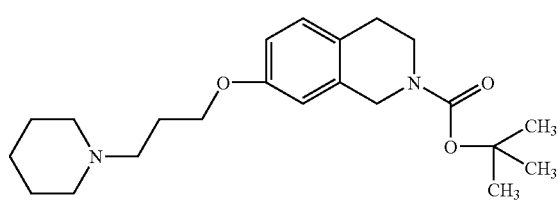 |

-continued
| Example Number | Structure |
|---|---|
| 238 | 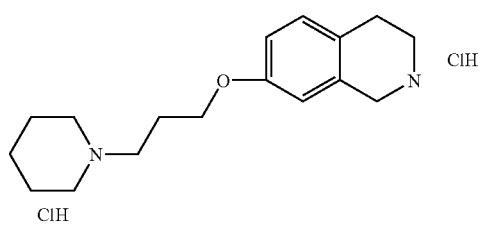 |
| 244 | 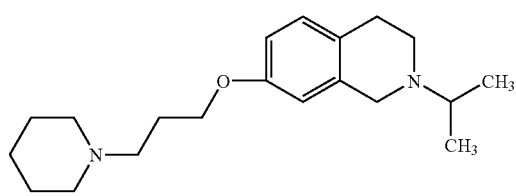 |
| 245 | 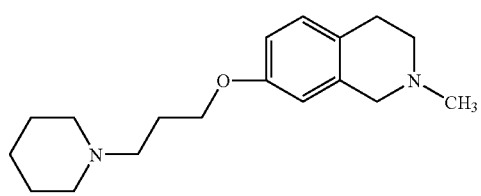 |
| 249 | 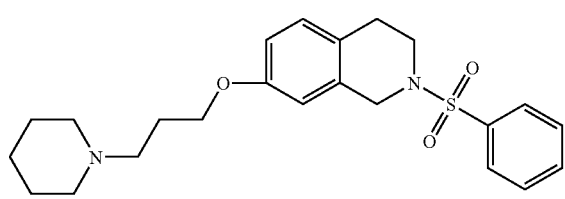 |
| 250 | 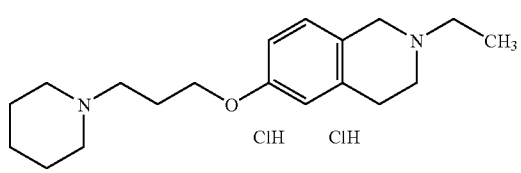 |
| 257 | 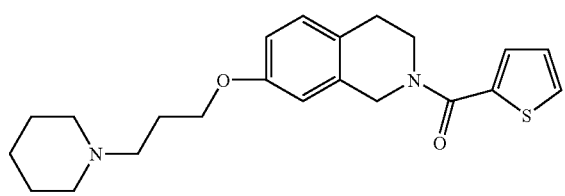 |
| 265 | 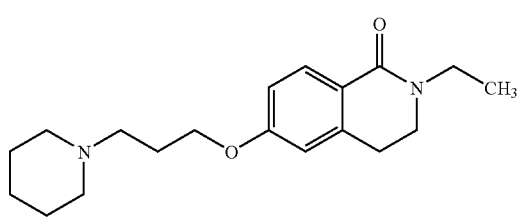 |

-continued
| Example Number | Structure |
|---|---|
| 266 | 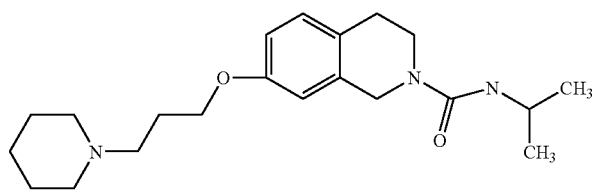 |
| 267 | 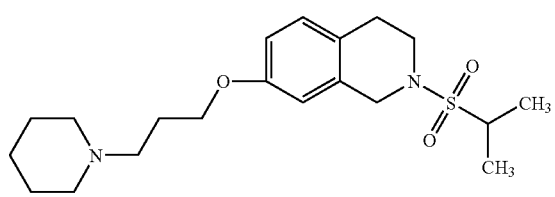 |
| 268 | 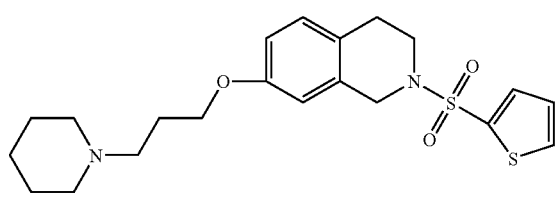 |
| 271 | 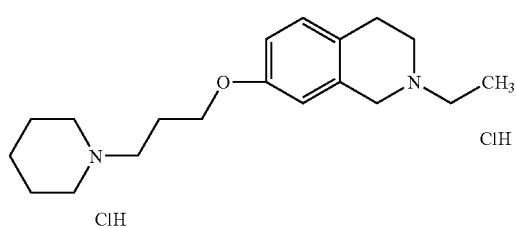 |
| 273 | 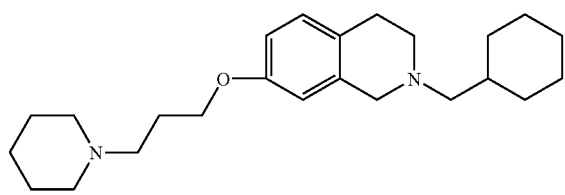 |
| 274 | 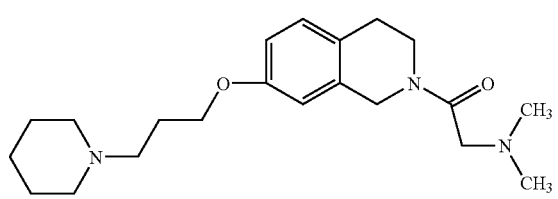 |
| 275 | 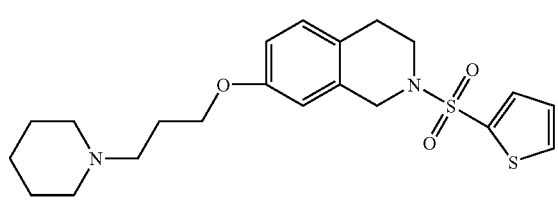 |

-continued
| Example Number | Structure |
|---|---|
| 276 | 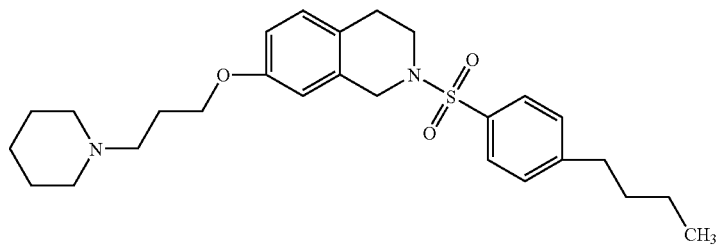 |
| 277 | 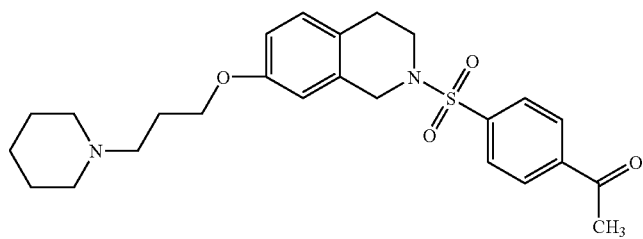 |
| 278 | 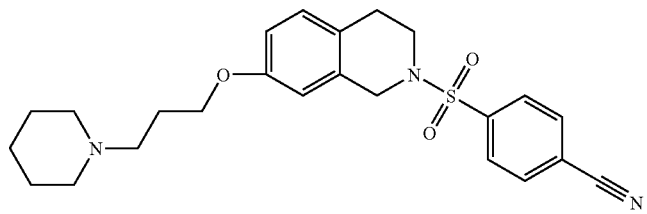 |
| 284 | 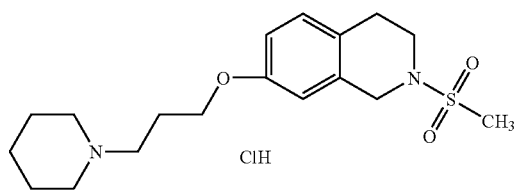 |
| 285 | 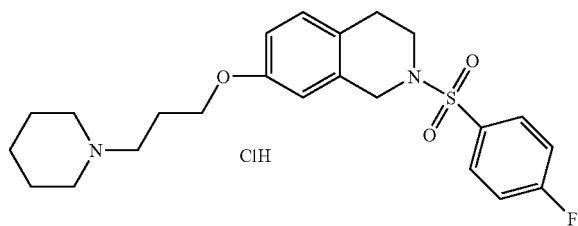 |
| 286 | 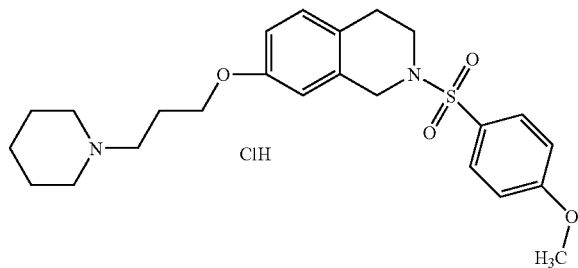 |

-continued
| Example Number | Structure |
|---|---|
| 287 | 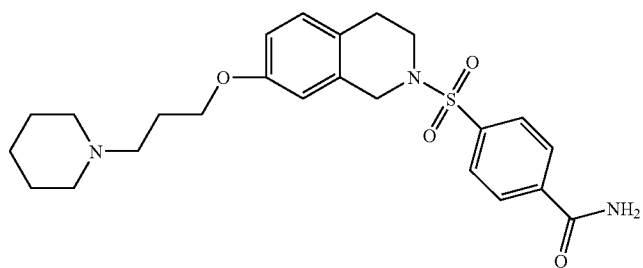 |
| 290 | 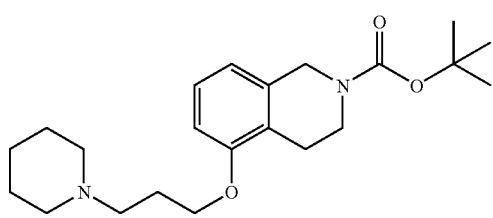 |
| 291 | 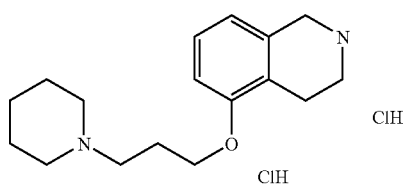 |
| 292 | 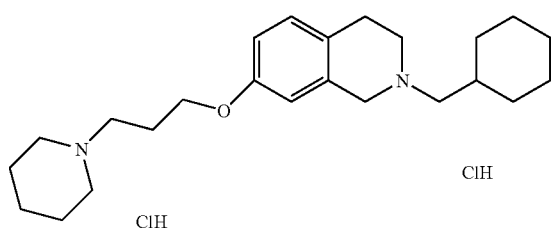 |
| 293 | 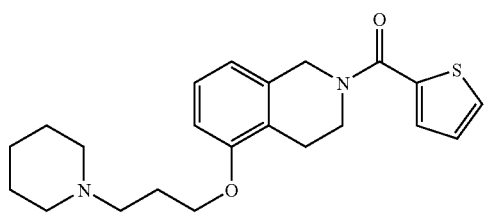 |
| 294 | 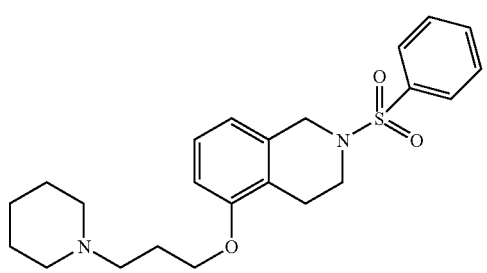 |

-continued
| Example Number | Structure |
|---|---|
| 302 | 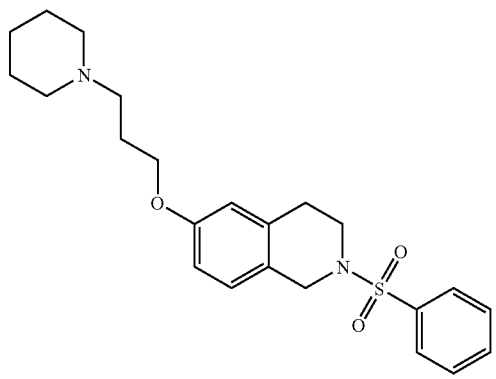 |
| 304 | 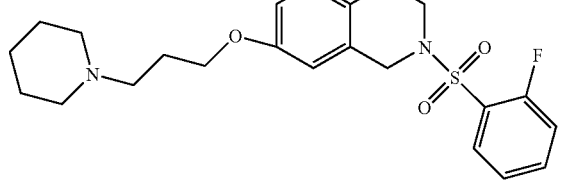 |
| 305 | 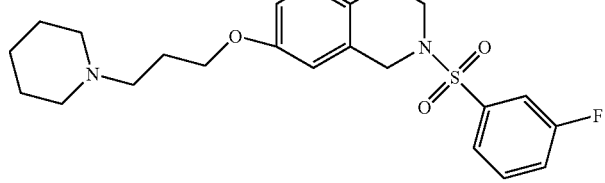 |
| 306 | 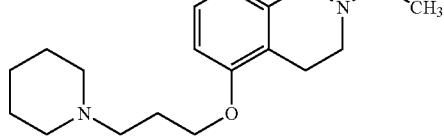 |
| 307 | 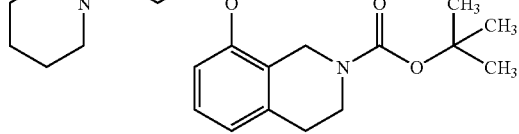 |
| 308 | 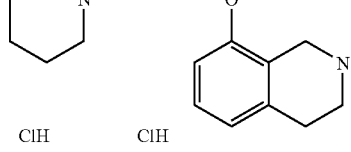<br>ClH  ClH |
| 309 | 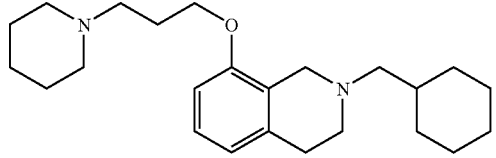 |

-continued
| Example Number | Structure |
|---|---|
| 310 | 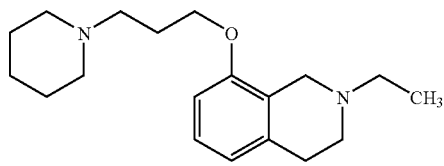 |
| 311 | 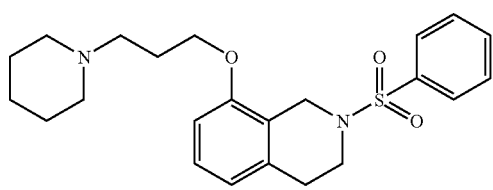 |
| 312 | 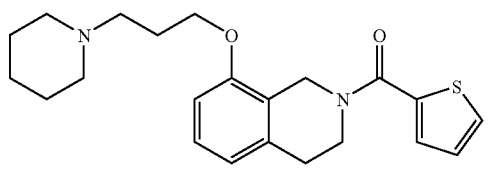 |
| 313 | 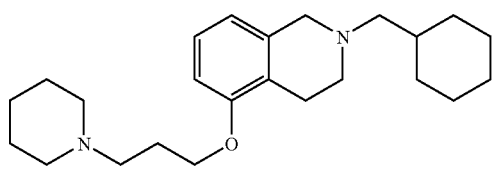 |
| 314 | 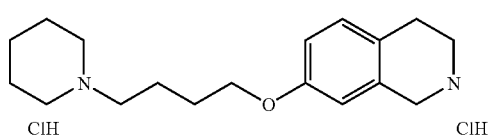 |
| 315 | 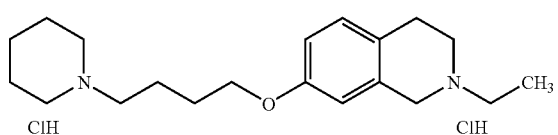 |
| 316 | 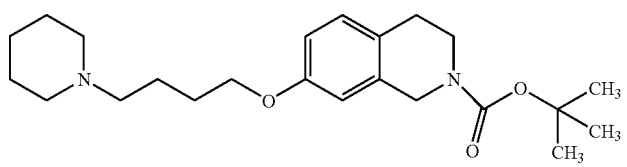 |
| 317 | 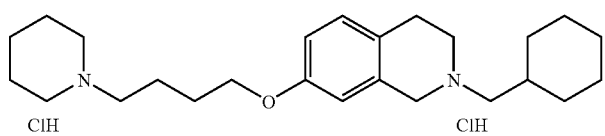 | or a pharmaceutically acceptable salt thereof.

3. A compound of claim 1 wherein the compound has the structure:

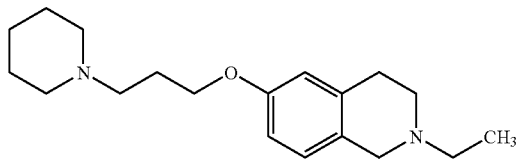

or a pharmaceutically acceptable salt thereof.

4. A compound of claim 1 wherein the compound has the structure:

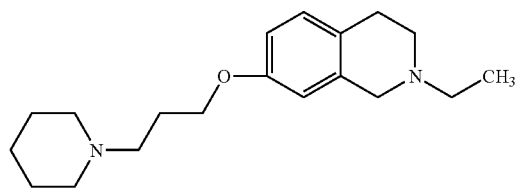

or a pharmaceutically acceptable salt or solvate thereof.

5. A compound of claim 1 wherein the compound has the structure:

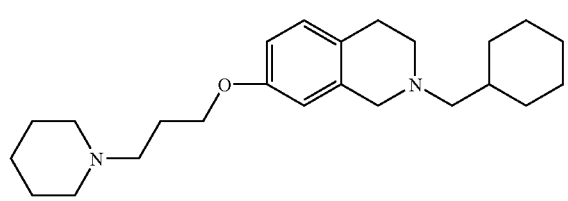

or a pharmaceutically acceptable salt or solvate thereof.

6. A pharmaceutical composition which comprises a compound of claim 1 and a pharmaceutically acceptable carrier.

* * * * *